(12) United States Patent  
Hemmingsen et al.

(10) Patent No.: US 9,642,809 B2  
(45) Date of Patent: *May 9, 2017

(54) CONTROLLED RELEASE PHARMACEUTICAL COMPOSITIONS FOR PROLONGED EFFECT

(71) Applicant: Egalet Ltd., London (GB)

(72) Inventors: Pernille Hoyrup Hemmingsen, Bagsvaerd (DK); Anders Vagno Pedersen, Virum (DK); Daniel Bar-Shalom, Kokkedal (DK)

(73) Assignee: EGALET LTD., London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/446,234

(22) Filed: Jul. 29, 2014

(65) Prior Publication Data

US 2015/0024048 A1    Jan. 22, 2015

Related U.S. Application Data

(63) Continuation of application No. 12/602,953, filed as application No. PCT/EP2008/056910 on Jun. 4, 2008, now Pat. No. 8,821,928.

(60) Provisional application No. 60/941,848, filed on Jun. 4, 2007.

(30) Foreign Application Priority Data

Jun. 4, 2007    (DK) .................................. 2007 00816

(51) Int. Cl.
| | |
|---|---|
| A61K 9/20 | (2006.01) |
| A61K 9/28 | (2006.01) |
| A61K 31/167 | (2006.01) |
| A61K 31/485 | (2006.01) |
| A61K 31/573 | (2006.01) |
| A61K 9/24 | (2006.01) |

(52) U.S. Cl.
CPC ............ *A61K 9/2086* (2013.01); *A61K 9/209* (2013.01); *A61K 9/2072* (2013.01); *A61K 9/2853* (2013.01); *A61K 9/2866* (2013.01); *A61K 31/167* (2013.01); *A61K 31/485* (2013.01); *A61K 31/573* (2013.01)

(58) Field of Classification Search
CPC ..... A61K 9/2086; A61K 9/2072; A61K 9/209
See application file for complete search history.

(56) References Cited

U.S. PATENT DOCUMENTS

| | | | |
|---|---|---|---|
| 2,685,553 | A | 3/1951 | Carroll et al. |
| 3,835,221 | A | 9/1974 | Fulberth et al. |
| 3,957,523 | A | 5/1976 | Ohno et al. |
| 4,034,758 | A | 7/1977 | Theeuwes |
| 4,330,338 | A | 5/1982 | Banker |
| 4,389,393 | A | 6/1983 | Schor et al. |
| 4,404,183 | A | 9/1983 | Kawata et al. |
| 4,449,983 | A | 5/1984 | Cortese et al. |
| 4,503,067 | A | 3/1985 | Wiedemann et al. |
| 4,686,212 | A | 8/1987 | Ducatman et al. |
| 4,769,372 | A | 9/1988 | Kreek |
| 4,824,675 | A | 4/1989 | Wong et al. |
| 4,844,984 | A | 7/1989 | Eckenhoff et al. |
| 4,873,080 | A | 10/1989 | Brickl et al. |
| 4,892,742 | A | 1/1990 | Shah |
| 4,898,733 | A | 2/1990 | De Prince et al. |
| 5,019,396 | A | 5/1991 | Ayer et al. |
| 5,068,112 | A | 11/1991 | Samejima et al. |

(Continued)

FOREIGN PATENT DOCUMENTS

| | | |
|---|---|---|
| EP | 0 435 726 A2 | 7/1991 |
| EP | 0 908 181 | 4/1999 |

(Continued)

OTHER PUBLICATIONS

Krogel et al (Pharmaceutical Research, 1998, vol. 15, pp. 474-481).*
U.S. Appl. No. 13/803,132, filed Aug. 25, 2006, Purdue Pharma C.
U.S. Appl. No. 13/900,933, filed Aug. 25, 2006, Purdue Pharma C.
U.S. Appl. No. 13/949,966, filed Dec. 18, 2002, Pain Therapeutics A.
International Search Report issued on Jul. 8, 2008 in application No. PCT/DK2008/000016 (corresponding to U.S. Pat. No. 8,603,526).
International Search Report issued on Oct. 20, 2009 in application No. PCT/DK2009/000192.
International Search Report issued on Apr. 21, 2010 in application No. PCT/EP2010/00728 (corresponding to US 2010/0204259).
International Search Report issued on May 18, 2010 in application No. PCT/DK2010/00019 (corresponding to U.S. Pat. No. 8,603,526).

(Continued)

*Primary Examiner* — Mark V Stevens
(74) *Attorney, Agent, or Firm* — Foley & Lardner LLP

(57) ABSTRACT

Layered pharmaceutical composition suitable for oral use in the treatment of diseases where absorption takes place over a large part of the gastrointestinal tract. The composition comprising A) a solid inner layer comprising
i) an active substance, and
ii) one or more disintegrants/exploding agents, one or more effervescent agents or a mixture thereof.
The solid inner layer being sandwiched between two outer layers B1) and B2), each outer layer comprising
iii) a substantially water soluble and/or crystalline polymer or a mixture of substantially water soluble and/or crystalline polymers, the polymer being a polyglycol in the form of one of a) a homopolymer having a MW of at least about 100,000 daltons, and b) a copolymer having a MW of at least about 2,000 daltons, or a mixture thereof, and
iv) an active substance, which is the same as in said solid inner layer A), and layer A being different from layer B, the layered composition being coated with a coating C) that has at least one opening exposing at least one surface of said outer layer, the coating being substantially insoluble in and impermeable to fluids and comprising a polymer, and the composition having a cylindrical form optionally with one or more tapered ends, wherein the ratio between the surface area of one end surface of the cylinder and the length of the cylinder is in a range of from 0.02 to 45 mm.

27 Claims, 24 Drawing Sheets

(56) References Cited

U.S. PATENT DOCUMENTS

| | | | |
|---|---|---|---|
| 5,102,668 A | 4/1992 | Eichel et al. | |
| 5,213,808 A * | 5/1993 | Bar-Shalom | A61K 9/2086 424/473 |
| 5,266,331 A | 11/1993 | Oshlack et al. | |
| 5,281,420 A | 1/1994 | Kelm et al. | |
| 5,352,455 A | 10/1994 | Robertson | |
| 5,411,745 A | 5/1995 | Oshlack et al. | |
| 5,419,917 A | 5/1995 | Chen et al. | |
| 5,422,123 A | 6/1995 | Conte et al. | |
| 5,460,826 A | 10/1995 | Merrill et al. | |
| 5,478,577 A | 12/1995 | Sackler et al. | |
| 5,508,042 A | 4/1996 | Oshlack et al. | |
| 5,520,931 A | 5/1996 | Persson et al. | |
| 5,549,912 A | 8/1996 | Oshlack et al. | |
| 5,593,695 A | 1/1997 | Merrill et al. | |
| 5,609,885 A | 3/1997 | Rivera et al. | |
| 5,614,218 A | 3/1997 | Olsson et al. | |
| 5,618,560 A | 4/1997 | Bar Shalom et al. | |
| 5,656,291 A | 8/1997 | Olsson et al. | |
| 5,656,295 A | 8/1997 | Oshlack et al. | |
| 5,667,805 A | 9/1997 | Merrill et al. | |
| 5,672,360 A | 9/1997 | Sackler et al. | |
| 5,741,524 A | 4/1998 | Staniforth et al. | |
| 5,866,161 A | 2/1999 | Childers et al. | |
| 5,866,164 A | 2/1999 | Kuczynski et al. | |
| 5,869,097 A | 2/1999 | Wong et al. | |
| 5,879,705 A | 3/1999 | Heafield et al. | |
| 5,882,682 A | 3/1999 | Rork et al. | |
| 5,914,131 A | 6/1999 | Merrill et al. | |
| 5,948,787 A | 9/1999 | Merrill et al. | |
| 5,952,005 A | 9/1999 | Olsson et al. | |
| 5,968,551 A | 10/1999 | Oshlack et al. | |
| 6,046,177 A | 4/2000 | Stella et al. | |
| 6,066,339 A | 5/2000 | Stark et al. | |
| 6,077,533 A | 6/2000 | Oshlack et al. | |
| 6,077,538 A | 6/2000 | Merrill et al. | |
| 6,103,261 A | 8/2000 | Chasin et al. | |
| 6,117,453 A | 9/2000 | Seth et al. | |
| 6,143,328 A | 11/2000 | Heafield et al. | |
| 6,183,778 B1 | 2/2001 | Conte et al. | |
| 6,225,343 B1 | 5/2001 | Behl et al. | |
| 6,245,351 B1 | 6/2001 | Nara et al. | |
| 6,245,357 B1 | 6/2001 | Edgren et al. | |
| 6,267,981 B1 | 7/2001 | Okamoto et al. | |
| 6,267,985 B1 | 7/2001 | Chen et al. | |
| 6,277,384 B1 | 8/2001 | Kaiko et al. | |
| 6,284,274 B1 | 9/2001 | Merrill et al. | |
| 6,294,195 B1 | 9/2001 | Oshlack et al. | |
| 6,348,216 B1 | 2/2002 | Kushla et al. | |
| 6,375,957 B1 | 4/2002 | Kaiko et al. | |
| 6,383,471 B1 | 5/2002 | Chen et al. | |
| 6,395,299 B1 | 5/2002 | Babich et al. | |
| 6,399,096 B1 | 6/2002 | Miller et al. | |
| 6,403,579 B1 | 6/2002 | Heller | |
| 6,451,848 B1 | 9/2002 | Behl et al. | |
| 6,458,772 B1 | 10/2002 | Zhou et al. | |
| 6,458,824 B1 | 10/2002 | Iwata et al. | |
| 6,475,494 B2 | 11/2002 | Kaiko et al. | |
| 6,482,437 B2 | 11/2002 | Debregeas et al. | |
| 6,488,962 B1 | 12/2002 | Berner et al. | |
| 6,488,963 B1 | 12/2002 | McGinty et al. | |
| 6,491,945 B1 | 12/2002 | Childers et al. | |
| 6,517,866 B1 | 2/2003 | Am Ende et al. | |
| 6,534,085 B1 | 3/2003 | Zeligs | |
| 6,543,085 B2 | 4/2003 | Holsten et al. | |
| 6,562,375 B1 | 5/2003 | Sako et al. | |
| 6,572,885 B2 | 6/2003 | Oshlack et al. | |
| 6,599,531 B2 | 7/2003 | Kushla et al. | |
| 6,607,751 B1 | 8/2003 | Odidi et al. | |
| 6,632,832 B1 | 10/2003 | Burman et al. | |
| 6,673,816 B1 | 1/2004 | Esswein et al. | |
| 6,685,964 B1 | 2/2004 | Bartholomaeus et al. | |
| 6,696,066 B2 | 2/2004 | Kaiko et al. | |
| 6,709,678 B2 | 3/2004 | Gruber | |
| 6,730,326 B2 | 5/2004 | Beyer et al. | |
| 6,733,783 B2 | 5/2004 | Oshlack et al. | |
| 6,757,558 B2 | 6/2004 | Lange et al. | |
| 6,787,156 B1 | 9/2004 | Bar-Shalom | |
| 6,800,668 B1 | 10/2004 | Odidi et al. | |
| 6,837,696 B2 | 1/2005 | Sowden et al. | |
| 6,852,337 B2 | 2/2005 | Gabel et al. | |
| 6,960,357 B2 | 11/2005 | Chopra | |
| 7,060,293 B1 | 6/2006 | Oshlack et al. | |
| 7,063,864 B1 | 6/2006 | Marechal et al. | |
| 7,090,867 B2 | 8/2006 | Odidi et al. | |
| 7,144,587 B2 | 12/2006 | Oshlack et al. | |
| 7,172,767 B2 | 2/2007 | Kaiko et al. | |
| 7,201,920 B2 | 4/2007 | Kumar et al. | |
| 7,270,831 B2 | 9/2007 | Oshlack et al. | |
| 7,332,182 B2 | 2/2008 | Sackler | |
| 7,399,488 B2 | 7/2008 | Hirsh et al. | |
| 7,419,686 B2 | 9/2008 | Kaiko et al. | |
| 7,476,402 B2 | 1/2009 | Kumar et al. | |
| 7,510,726 B2 | 3/2009 | Kumar et al. | |
| 7,510,727 B2 | 3/2009 | Oshlack et al. | |
| 7,514,100 B2 | 4/2009 | Oshlack et al. | |
| 7,666,337 B2 | 2/2010 | Yang et al. | |
| 7,749,542 B2 | 7/2010 | Kaiko et al. | |
| 7,771,707 B2 | 8/2010 | Hirsh et al. | |
| 7,776,314 B2 | 8/2010 | Bartholomaus et al. | |
| 7,790,215 B2 | 9/2010 | Sackler et al. | |
| 7,842,307 B2 | 11/2010 | Oshlack et al. | |
| 7,846,476 B2 | 12/2010 | Oshlack et al. | |
| 7,883,722 B2 | 2/2011 | Bar-Shalom | |
| 7,883,772 B2 | 2/2011 | Pourdeyhimi et al. | |
| 7,897,080 B2 | 3/2011 | Yang et al. | |
| 7,906,143 B1 | 3/2011 | Odidi et al. | |
| 7,943,174 B2 | 5/2011 | Oshlack et al. | |
| 7,968,120 B2 | 6/2011 | Li et al. | |
| 7,972,624 B2 | 7/2011 | Li et al. | |
| 7,981,439 B2 | 7/2011 | Kumar et al. | |
| 8,017,148 B2 | 9/2011 | Sackler | |
| 8,017,150 B2 | 9/2011 | Yang et al. | |
| 8,029,822 B2 | 10/2011 | Faour et al. | |
| 8,075,872 B2 | 12/2011 | Arkenau-Marie et al. | |
| 8,101,630 B2 | 1/2012 | Kumar et al. | |
| 8,105,631 B2 | 1/2012 | Kaiko et al. | |
| 8,114,383 B2 | 2/2012 | Bartholomaus et al. | |
| 8,114,384 B2 | 2/2012 | Arkenau et al. | |
| 8,133,507 B2 | 3/2012 | Yum et al. | |
| 8,142,811 B2 | 3/2012 | Oshlack et al. | |
| 8,147,870 B2 | 4/2012 | Yum et al. | |
| 8,153,152 B2 | 4/2012 | Yum et al. | |
| 8,168,217 B2 | 5/2012 | Yum et al. | |
| 8,173,152 B2 | 5/2012 | Crowley et al. | |
| 8,182,836 B2 | 5/2012 | Mehta | |
| 8,192,722 B2 | 6/2012 | Arkenau-Maric et al. | |
| 8,231,898 B2 | 7/2012 | Oshlack et al. | |
| 8,246,986 B2 | 8/2012 | Cruz et al. | |
| 8,309,060 B2 | 11/2012 | Bartholomaus et al. | |
| 8,323,889 B2 | 12/2012 | Arkenou-Maric et al. | |
| 8,329,720 B1 | 12/2012 | King et al. | |
| 8,337,888 B2 | 12/2012 | Wright et al. | |
| 8,338,444 B1 | 12/2012 | King et al. | |
| 8,354,124 B2 | 1/2013 | Yum et al. | |
| 8,361,499 B2 | 1/2013 | Oshlack et al. | |
| 8,367,693 B1 | 2/2013 | King et al. | |
| 8,372,432 B2 | 2/2013 | Han et al. | |
| 8,377,453 B2 | 2/2013 | Han et al. | |
| 8,383,152 B2 | 2/2013 | Jans et al. | |
| 8,383,154 B2 | 2/2013 | Bar-Shalom | |
| 8,383,155 B2 | 2/2013 | Bar-Shalom | |
| 8,389,007 B2 | 3/2013 | Wright et al. | |
| 8,394,407 B2 | 3/2013 | Vergnault et al. | |
| 8,394,408 B2 | 3/2013 | Han et al. | |
| 8,409,616 B2 | 4/2013 | Kumar et al. | |
| 8,415,401 B2 | 4/2013 | Yum et al. | |
| 8,420,056 B2 | 4/2013 | Arkenau-Maric et al. | |
| 8,420,120 B2 | 4/2013 | Yum et al. | |
| 8,425,933 B2 | 4/2013 | Mehta | |
| 8,445,018 B2 | 5/2013 | Habib et al. | |
| 8,449,909 B2 | 5/2013 | Hirsch et al. | |
| 8,449,914 B2 | 5/2013 | Fischer et al. | |
| 8,460,640 B2 | 6/2013 | Vinson et al. | |

(56) References Cited

U.S. PATENT DOCUMENTS

| | | |
|---|---|---|
| 8,465,776 B2 | 6/2013 | Hoarau |
| 8,470,361 B2 | 6/2013 | Pettersson |
| 8,476,291 B1 | 7/2013 | King et al. |
| 8,486,423 B2 | 7/2013 | Brough et al. |
| 8,486,448 B2 | 7/2013 | Rahmouni et al. |
| 8,486,449 B2 | 7/2013 | Rahmouni et al. |
| 8,491,935 B2 | 7/2013 | Mehta et al. |
| 8,501,160 B2 | 8/2013 | Cailly-Dufestel et al. |
| 8,506,998 B2 | 8/2013 | Miller et al. |
| 8,524,275 B2 | 9/2013 | Oshlack et al. |
| 8,524,277 B2 | 9/2013 | Edgren et al. |
| 8,529,848 B2 | 9/2013 | Danehy et al. |
| 8,541,026 B2 | 9/2013 | Qiu et al. |
| 8,603,526 B2 | 12/2013 | Tygesen et al. |
| 8,609,143 B2 | 12/2013 | Fischer et al. |
| 8,609,683 B2 | 12/2013 | Wright et al. |
| 8,617,605 B2 | 12/2013 | Fischer et al. |
| 8,637,540 B2 | 1/2014 | Kumar et al. |
| 8,703,189 B2 | 4/2014 | Tomohira et al. |
| 8,765,178 B2 | 7/2014 | Parikh et al. |
| 8,808,745 B2 | 8/2014 | Fischer et al. |
| 8,821,928 B2 | 9/2014 | Hemmingsen |
| 8,877,241 B2 | 11/2014 | Fischer et al. |
| 9,005,660 B2 | 4/2015 | Tygesen et al. |
| 9,023,394 B2 | 5/2015 | Andersen et al. |
| 9,044,402 B2 | 6/2015 | Tygesen et al. |
| 9,168,228 B2 | 10/2015 | Tygesen et al. |
| 9,358,295 B2 | 6/2016 | Tygesen et al. |
| 9,375,428 B2 | 6/2016 | Fischer et al. |
| 2001/0036959 A1 | 11/2001 | Gabel et al. |
| 2001/0036960 A1 | 11/2001 | Decker et al. |
| 2001/0053791 A1 | 12/2001 | Babcock et al. |
| 2002/0054911 A1 | 5/2002 | Oh |
| 2002/0107434 A1 | 8/2002 | Lange et al. |
| 2002/0119197 A1 | 8/2002 | Dyar et al. |
| 2003/0035836 A1 | 2/2003 | Shanghvi et al. |
| 2003/0068375 A1 | 4/2003 | Wright et al. |
| 2003/0077320 A1 | 4/2003 | Childers et al. |
| 2003/0091635 A1 | 5/2003 | Baichwal et al. |
| 2003/0118641 A1 | 6/2003 | Maloney et al. |
| 2003/0133976 A1 | 7/2003 | Pather et al. |
| 2003/0203055 A1 | 10/2003 | Rao et al. |
| 2003/0224051 A1 | 12/2003 | Fink et al. |
| 2004/0010000 A1 | 1/2004 | Ayer et al. |
| 2004/0028733 A1 | 2/2004 | Tracy et al. |
| 2004/0091529 A1 | 5/2004 | Edgren et al. |
| 2004/0102476 A1 | 5/2004 | Chan et al. |
| 2004/0115262 A1 | 6/2004 | Jao et al. |
| 2004/0151772 A1 | 8/2004 | Andersen et al. |
| 2004/0202717 A1 | 10/2004 | Mehta |
| 2004/0204474 A1 | 10/2004 | Decker et al. |
| 2004/0213849 A1 | 10/2004 | Sowden et al. |
| 2004/0220250 A1 | 11/2004 | Oh et al. |
| 2004/0224020 A1 | 11/2004 | Schoenhard |
| 2004/0234602 A1 | 11/2004 | Fischer et al. |
| 2004/0253310 A1 | 12/2004 | Fischer et al. |
| 2005/0019399 A1 | 1/2005 | Fischer et al. |
| 2005/0019405 A1 | 1/2005 | Bar-Shalom |
| 2005/0020613 A1 | 1/2005 | Boehm et al. |
| 2005/0053655 A1 | 3/2005 | Yang et al. |
| 2005/0074493 A1 | 4/2005 | Mehta et al. |
| 2005/0089569 A1 | 4/2005 | Bar-Shalom |
| 2005/0089570 A1 | 4/2005 | Cruz et al. |
| 2005/0095295 A1 | 5/2005 | Maggi et al. |
| 2005/0106249 A1 | 5/2005 | Hwang et al. |
| 2005/0158382 A1 | 7/2005 | Cruz et al. |
| 2005/0163837 A1 | 7/2005 | Boehm et al. |
| 2005/0169992 A1 | 8/2005 | Jao et al. |
| 2005/0236741 A1 | 10/2005 | Arkenaou et al. |
| 2006/0002860 A1 | 1/2006 | Bartholomous et al. |
| 2006/0039864 A1 | 2/2006 | Barthlomaus et al. |
| 2006/0110327 A1 | 5/2006 | Emigh et al. |
| 2006/0165790 A1 | 7/2006 | Walden et al. |
| 2006/0177380 A1 | 8/2006 | Emigh et al. |
| 2006/0177507 A1 | 8/2006 | Faour et al. |
| 2006/0188447 A1 | 8/2006 | Arkenau-Maric et al. |
| 2006/0193782 A1 | 8/2006 | Bartholomaus et al. |
| 2006/0193912 A1 | 8/2006 | Ketsela et al. |
| 2006/0193914 A1 | 8/2006 | Ashworth et al. |
| 2007/0003616 A1 | 1/2007 | Arkenau-Maric et al. |
| 2007/0003617 A1 | 1/2007 | Fischer et al. |
| 2007/0003620 A1 | 1/2007 | Marechal et al. |
| 2007/0004797 A1 | 1/2007 | Weyers et al. |
| 2007/0020331 A1 | 1/2007 | Gold et al. |
| 2007/0042044 A1 | 2/2007 | Fischer et al. |
| 2007/0048228 A1 | 3/2007 | Arkenau-Maric et al. |
| 2007/0065364 A1 | 3/2007 | Oshlack et al. |
| 2007/0065510 A1 | 3/2007 | Odidi et al. |
| 2007/0122455 A1 | 5/2007 | Myers et al. |
| 2007/0183980 A1 | 8/2007 | Arkenau-Maric et al. |
| 2007/0190142 A1 | 8/2007 | Breitenbach et al. |
| 2007/0224129 A1 | 9/2007 | Guimberteau et al. |
| 2007/0231268 A1 | 10/2007 | Emigh et al. |
| 2007/0259033 A1 | 11/2007 | Cruz et al. |
| 2007/0259045 A1 | 11/2007 | Mannion et al. |
| 2007/0264326 A1 | 11/2007 | Guimberteau et al. |
| 2007/0264346 A1 | 11/2007 | Guimberteau et al. |
| 2007/0275062 A1 | 11/2007 | Oshlack et al. |
| 2007/0281003 A1 | 12/2007 | Fuisz et al. |
| 2007/0281007 A1 | 12/2007 | Jacob et al. |
| 2008/0026052 A1 | 1/2008 | Schoenhard |
| 2008/0031901 A1 | 2/2008 | Qiu et al. |
| 2008/0044454 A1 | 2/2008 | Yang et al. |
| 2008/0063725 A1 | 3/2008 | Guimberteau et al. |
| 2008/0069891 A1 | 3/2008 | Habib et al. |
| 2008/0075771 A1 | 3/2008 | Vaughn et al. |
| 2008/0102121 A1 | 5/2008 | Devane et al. |
| 2008/0113025 A1 | 5/2008 | Devane et al. |
| 2008/0152595 A1 | 6/2008 | Emigh et al. |
| 2008/0166405 A1 | 7/2008 | Mehta |
| 2008/0166407 A1 | 7/2008 | Shalaby et al. |
| 2008/0193540 A1 | 8/2008 | Soula et al. |
| 2008/0200493 A1 | 8/2008 | Drewes et al. |
| 2008/0234352 A1 | 9/2008 | Fischer et al. |
| 2008/0247959 A1 | 10/2008 | Barthlomaus et al. |
| 2008/0248110 A1 | 10/2008 | Pettersson et al. |
| 2008/0248113 A1 | 10/2008 | Barthlomaus et al. |
| 2008/0254122 A1 | 10/2008 | Fischer et al. |
| 2008/0254123 A1 | 10/2008 | Fischer et al. |
| 2008/0254124 A1 | 10/2008 | Bar-Shalom |
| 2008/0268057 A1 | 10/2008 | Andersen et al. |
| 2008/0311187 A1 | 12/2008 | Ashworth et al. |
| 2008/0311197 A1 | 12/2008 | Arkenau-Maric et al. |
| 2008/0311205 A1 | 12/2008 | Habib et al. |
| 2008/0317854 A1 | 12/2008 | Arkenau et al. |
| 2009/0004267 A1 | 1/2009 | Arkenau-Maric et al. |
| 2009/0005408 A1 | 1/2009 | Arkenau-Maric et al. |
| 2009/0011016 A1 | 1/2009 | Cailly-Dufestel et al. |
| 2009/0022790 A1 | 1/2009 | Flath et al. |
| 2009/0022798 A1 | 1/2009 | Rosenberg et al. |
| 2009/0041838 A1 | 2/2009 | Guimberteau et al. |
| 2009/0081290 A1 | 3/2009 | McKenna et al. |
| 2009/0099151 A1 | 4/2009 | Jain et al. |
| 2009/0123386 A1 | 5/2009 | Young |
| 2009/0155357 A1 | 6/2009 | Muhuri |
| 2009/0169631 A1 | 7/2009 | Zamloot et al. |
| 2009/0202634 A1 | 8/2009 | Jans et al. |
| 2009/0221621 A1 | 9/2009 | Sathyan et al. |
| 2009/0232887 A1 | 9/2009 | Odidi et al. |
| 2009/0274759 A1 | 11/2009 | Bar-Shalom et al. |
| 2009/0298862 A1 | 12/2009 | Yum et al. |
| 2009/0317355 A1 | 12/2009 | Roth et al. |
| 2010/0099696 A1 | 4/2010 | Soscia et al. |
| 2010/0151028 A1 | 6/2010 | Ashworth et al. |
| 2010/0168148 A1 | 7/2010 | Wright et al. |
| 2010/0172989 A1 | 7/2010 | Roth et al. |
| 2010/0203129 A1 | 8/2010 | Andersen et al. |
| 2010/0204259 A1 | 8/2010 | Tygesen et al. |
| 2010/0266701 A1 | 10/2010 | Guimberteau et al. |
| 2010/0291205 A1 | 11/2010 | Downie et al. |
| 2011/0008424 A1 | 1/2011 | Chang et al. |
| 2011/0020451 A1 | 1/2011 | Bartholmaus et al. |
| 2011/0038930 A1 | 2/2011 | Barnscheid et al. |
| 2011/0077238 A1 | 3/2011 | Leech et al. |

(56) References Cited

U.S. PATENT DOCUMENTS

| | | |
|---|---|---|
| 2011/0104214 A1 | 5/2011 | Oshlack et al. |
| 2011/0136847 A1 | 6/2011 | Chan et al. |
| 2011/0142905 A1 | 6/2011 | Naelapaa et al. |
| 2011/0159100 A1 | 6/2011 | Andersen et al. |
| 2011/0165248 A1 | 7/2011 | Machonis |
| 2011/0195989 A1 | 8/2011 | Rudnic et al. |
| 2011/0200681 A1 | 8/2011 | Habib et al. |
| 2011/0200715 A1 | 8/2011 | Fuisz et al. |
| 2011/0229526 A1 | 9/2011 | Rosenberg et al. |
| 2011/0229533 A1 | 9/2011 | Edgren et al. |
| 2011/0287093 A1 | 11/2011 | Schoenhard |
| 2012/0009129 A1 | 1/2012 | Brzeczko |
| 2012/0059065 A1 | 3/2012 | Barnscheid et al. |
| 2012/0065220 A1 | 3/2012 | Barnscheid et al. |
| 2012/0135075 A1 | 5/2012 | Mohammad |
| 2012/0136021 A1 | 5/2012 | Barnscheid et al. |
| 2012/0164220 A1 | 6/2012 | Huang |
| 2012/0201761 A1 | 8/2012 | Sackler |
| 2012/0202838 A1 | 8/2012 | Ghosh et al. |
| 2012/0202839 A1 | 8/2012 | Emigh et al. |
| 2012/0214777 A1 | 8/2012 | Crowley et al. |
| 2012/0225122 A1 | 9/2012 | Hamed et al. |
| 2012/0251637 A1 | 10/2012 | Bartholomaus et al. |
| 2012/0321674 A1 | 12/2012 | Vachon et al. |
| 2012/0321713 A1 | 12/2012 | Han et al. |
| 2012/0321716 A1 | 12/2012 | Vachon et al. |
| 2013/0005823 A1 | 1/2013 | Emigh et al. |
| 2013/0011479 A1 | 1/2013 | Angeli et al. |
| 2013/0012533 A1 | 1/2013 | Oshlack et al. |
| 2013/0022646 A1 | 1/2013 | Rudnic et al. |
| 2013/0028177 A1 | 1/2013 | Koskela et al. |
| 2013/0028970 A1 | 1/2013 | Schwier et al. |
| 2013/0028972 A1 | 1/2013 | Schwier et al. |
| 2013/0030561 A1 | 1/2013 | Imanari et al. |
| 2013/0084333 A1 | 4/2013 | Dick et al. |
| 2013/0090349 A1 | 4/2013 | Geibler et al. |
| 2013/0122087 A1 | 5/2013 | Habib et al. |
| 2013/0122101 A1 | 5/2013 | Habib et al. |
| 2013/0129826 A1 | 5/2013 | Geibler et al. |
| 2013/0171075 A1 | 7/2013 | Arkenau-Maric et al. |
| 2013/0171257 A1 | 7/2013 | Kumar et al. |
| 2013/0195981 A1 | 8/2013 | Pettersson |
| 2013/0195982 A1 | 8/2013 | Pettersson |
| 2013/0209557 A1 | 8/2013 | Barnscheid |
| 2013/0209560 A1 | 8/2013 | Hamed et al. |
| 2013/0217716 A1 | 8/2013 | Wright et al. |
| 2013/0225697 A1 | 8/2013 | Barnscheid et al. |
| 2013/0230596 A1 | 9/2013 | Mehta |
| 2013/0245055 A1 | 9/2013 | Wright et al. |
| 2013/0251759 A1 | 9/2013 | Jans et al. |
| 2013/0251796 A1 | 9/2013 | McKenna et al. |
| 2013/0251797 A1 | 9/2013 | McKenna et al. |
| 2013/0251798 A1 | 9/2013 | McKenna et al. |
| 2013/0251799 A1 | 9/2013 | McKenna et al. |
| 2013/0251801 A1 | 9/2013 | McKenna et al. |
| 2013/0251802 A1 | 9/2013 | McKenna et al. |
| 2013/0251806 A1 | 9/2013 | Andrade de Freitas et al. |
| 2013/0259939 A1 | 10/2013 | McKenna et al. |
| 2013/0259940 A1 | 10/2013 | McKenna et al. |
| 2013/0260015 A1 | 10/2013 | McKenna et al. |
| 2013/0261143 A1 | 10/2013 | Wright et al. |
| 2013/0273162 A1 | 10/2013 | Li et al. |
| 2013/0280176 A1 | 10/2013 | Diezi et al. |
| 2013/0280338 A1 | 10/2013 | Wening et al. |
| 2013/0281480 A1 | 10/2013 | Yum et al. |
| 2013/0287845 A1 | 10/2013 | Yum et al. |
| 2013/0287849 A1 | 10/2013 | Andersen et al. |
| 2013/0295168 A1 | 11/2013 | Yum et al. |
| 2013/0303494 A1 | 11/2013 | Wright et al. |
| 2013/0317049 A1 | 11/2013 | Yum et al. |
| 2013/0317051 A1 | 11/2013 | Oshlack et al. |
| 2013/0320592 A1 | 12/2013 | Arkenau-Maric et al. |
| 2013/0337059 A1 | 12/2013 | Yum et al. |
| 2013/0337060 A1 | 12/2013 | Yum et al. |
| 2013/0344142 A1 | 12/2013 | Rahmouni et al. |
| 2013/0344143 A1 | 12/2013 | Rosenberg et al. |
| 2014/0004191 A1 | 1/2014 | Rahmouni et al. |
| 2014/0030327 A1 | 1/2014 | McKenna et al. |
| 2014/0120164 A1 | 5/2014 | Fischer et al. |
| 2014/0155388 A1 | 6/2014 | Brzeczko et al. |
| 2014/0221416 A1 | 8/2014 | Guido et al. |
| 2014/0271848 A1 | 9/2014 | Guido et al. |
| 2014/0271896 A1 | 9/2014 | Abu Shmeis et al. |
| 2014/0275143 A1 | 9/2014 | Devarakonda et al. |
| 2014/0294947 A1 | 10/2014 | Reilly et al. |
| 2015/0037417 A1 | 2/2015 | Fischer et al. |
| 2015/0079150 A1 | 3/2015 | Fischer et al. |
| 2015/0313997 A1 | 11/2015 | Tygesen et al. |

FOREIGN PATENT DOCUMENTS

| | | |
|---|---|---|
| EP | 1 027 888 | 8/2000 |
| EP | 0 335 560 | 1/2002 |
| EP | 1 213 014 A2 | 6/2002 |
| EP | 1 371 360 | 5/2005 |
| GB | 1430684 | 3/1976 |
| GB | 2170104 | 7/1986 |
| GB | 2182559 | 5/1987 |
| JP | 60/255719 | 12/1985 |
| JP | 07/100191 | 4/1995 |
| WO | WO 86/04817 | 8/1986 |
| WO | WO-89/09066 A | 10/1989 |
| WO | WO 90/08536 | 8/1990 |
| WO | WO-91-04015 A | 4/1991 |
| WO | WO 92/09270 | 6/1992 |
| WO | WO 93/10765 | 6/1993 |
| WO | WO 95/22962 | 8/1995 |
| WO | WO 96/00066 A1 | 1/1996 |
| WO | WO 96/08253 A1 | 3/1996 |
| WO | WO 97/33566 A2 | 9/1997 |
| WO | WO 99/05105 | 2/1999 |
| WO | WO-99/44591 A | 9/1999 |
| WO | WO 99/44591 A1 | 9/1999 |
| WO | WO 01/35958 | 5/2001 |
| WO | WO 01/51035 | 7/2001 |
| WO | WO 01/51036 | 7/2001 |
| WO | WO 01/74357 | 10/2001 |
| WO | WO 02/056861 A2 | 7/2002 |
| WO | WO 02/065834 | 8/2002 |
| WO | WO 02/087512 A1 | 11/2002 |
| WO | WO 02/092078 | 11/2002 |
| WO | WO 03/039521 | 5/2003 |
| WO | WO 03/092648 A1 | 11/2003 |
| WO | WO 03/101384 A2 | 12/2003 |
| WO | WO 2004/002447 A2 | 1/2004 |
| WO | WO 2004/047839 A1 | 6/2004 |
| WO | WO 2004/054542 A2 | 7/2004 |
| WO | WO 2004/056337 A2 | 7/2004 |
| WO | WO 2004/091512 A2 | 10/2004 |
| WO | WO 2005/000310 A1 | 1/2005 |
| WO | WO 2005/007074 | 1/2005 |
| WO | WO 2005/016313 A1 | 2/2005 |
| WO | WO 2005/016314 A1 | 2/2005 |
| WO | WO 2005/027878 | 3/2005 |
| WO | WO 2005/034859 A2 | 4/2005 |
| WO | WO 2005/053587 A1 | 6/2005 |
| WO | WO 2005/063206 A1 | 7/2005 |
| WO | WO 2005/063214 A1 | 7/2005 |
| WO | WO 2005/102286 A1 | 11/2005 |
| WO | WO 2006/002883 A1 | 1/2006 |
| WO | WO 2006/002884 A1 | 1/2006 |
| WO | WO 2006/002886 A1 | 1/2006 |
| WO | WO 2006/026504 | 3/2006 |
| WO | WO 2006/030402 A2 | 3/2006 |
| WO | WO 2006/031209 A1 | 3/2006 |
| WO | WO 2006/058249 A2 | 6/2006 |
| WO | WO 2006/088305 A1 | 8/2006 |
| WO | WO 2006/089843 A2 | 8/2006 |
| WO | WO 2006/103418 A1 | 10/2006 |
| WO | WO 2006/103551 | 10/2006 |
| WO | WO 2007/014061 A2 | 2/2007 |
| WO | WO 2007/030754 A2 | 3/2007 |
| WO | WO 2007/082757 A2 | 7/2007 |
| WO | WO 2007/085024 A2 | 7/2007 |

(56) References Cited

FOREIGN PATENT DOCUMENTS

| | | |
|---|---|---|
| WO | WO 2007/106550 A2 | 9/2007 |
| WO | WO 2007/112285 A2 | 10/2007 |
| WO | WO 2007/112286 A2 | 10/2007 |
| WO | WO 2007/133583 A2 | 11/2007 |
| WO | WO 2007/135193 A2 | 11/2007 |
| WO | WO 2007/150074 A2 | 12/2007 |
| WO | WO 2007/150075 A2 | 12/2007 |
| WO | WO 2008/023261 A1 | 2/2008 |
| WO | WO 2008/027442 A2 | 3/2008 |
| WO | WO 2008/028047 A2 | 3/2008 |
| WO | WO 2008/033523 A1 | 3/2008 |
| WO | WO 2008/068471 A1 | 6/2008 |
| WO | WO 2008/100375 A2 | 8/2008 |
| WO | WO 2008/107149 A2 | 9/2008 |
| WO | WO 2009/035474 A1 | 3/2009 |
| WO | WO 2009/075782 A1 | 6/2009 |
| WO | WO 2009/076236 A2 | 6/2009 |
| WO | WO 2009/076764 A1 | 6/2009 |
| WO | WO 2009/088414 A2 | 7/2009 |
| WO | WO 2009/092601 A1 | 7/2009 |
| WO | WO 2009/104838 A1 | 8/2009 |
| WO | WO 2009/114648 A1 | 9/2009 |
| WO | WO 2010/017821 A1 | 2/2010 |
| WO | WO 2010/032128 A1 | 3/2010 |
| WO | WO 2010/066034 A1 | 6/2010 |
| WO | WO 2010/069050 A1 | 6/2010 |
| WO | WO 2010/083894 A1 | 7/2010 |
| WO | WO 2010/140007 A2 | 12/2010 |
| WO | WO 2010/151741 A1 | 12/2010 |
| WO | WO 2011/009602 A1 | 1/2011 |
| WO | WO 2011/009603 A1 | 1/2011 |
| WO | WO 2011/009604 A1 | 1/2011 |
| WO | WO 2011/041414 A1 | 4/2011 |
| WO | WO 2011/068723 A1 | 6/2011 |
| WO | WO 2011/079248 A1 | 6/2011 |
| WO | WO 2011/106416 A2 | 9/2011 |
| WO | WO 2012/028317 A1 | 3/2012 |
| WO | WO 2012/028318 A1 | 3/2012 |
| WO | WO 2012/028319 A1 | 3/2012 |
| WO | WO 2012/040651 A1 | 3/2012 |
| WO | WO 2012/061779 A1 | 5/2012 |
| WO | WO 2012/076907 A2 | 6/2012 |
| WO | WO 2012/080833 A2 | 6/2012 |
| WO | WO 2012/085656 A2 | 6/2012 |
| WO | WO 2012/085657 A2 | 6/2012 |
| WO | WO 2012/112952 A1 | 8/2012 |
| WO | WO 2012/131463 A2 | 10/2012 |
| WO | WO 2013/017234 A1 | 2/2013 |
| WO | WO 2013/017242 A1 | 2/2013 |
| WO | WO 2013/038267 A1 | 3/2013 |
| WO | WO 2013/038268 A1 | 3/2013 |
| WO | WO 2013/050539 A2 | 4/2013 |
| WO | WO 2013/057570 A2 | 4/2013 |
| WO | WO 2013/072395 A1 | 5/2013 |
| WO | WO 2013/077851 A1 | 5/2013 |
| WO | WO 2013/084059 A1 | 6/2013 |

OTHER PUBLICATIONS

International Search Report issued on Jun. 2, 2010 in application No. PCT/DK2010/050016 (corresponding to US 2010/203129).
International Search Report issued on Jan. 28, 2009 in application No. PCT/EP2008/056910 (corresponding to US 2010/239667).
MiraLAX®, "MiraLAX® Drug Description," Oct. 19, 2011.
Raehal et al., "Mu Opioid 'Receptor' Regulation and Opiate Responsiveness," The AAPS Journal, vol. 7, No. 3, pp. E587-E591, 2005.
Qiu et al., "Design of a core-shelled polymer cylinder for potential programmable drug delivery," International Journal of Pharmaceutics, vol. 219, pp. 151-160, 2001.
Haahr et al., "Drug abuse resistant, controlled release, using Egalet® dosage units," Proceedings of the 34th Annual Meeting Exposition of the Controlled Release Society, Poster, Jul. 7-11, 2007.
Meyer et al., "Awareness Topic: Mitigating the Risks of Ethanol Induced Dose Dumping from Oral Sustained/Controlled Release Dosage Forms," FDA's ACPS meeting, Oct. 2005.
Dahlstrom et al., "Patient-controlled Analgesic Therapy, Part IV: Pharmacokinectics and Analgesic Plasma Concentration of Morphine," Clinical Pharmacokinectics, vol. 7, pp. 266-279, 1982.
Fischer et al., "Nonmedical Use of Prescription Opioids: Furthering a Meaningful Research Agenda," The Journal of Pain, vol. 9, No. 6, pp. 490-493, Jun. 2008.
Camu et al., "Pharmacology of systemic analgesics," Best Practice & Research Clinical Anaesthesiology, vol. 16, No. 4, pp. 475-488, 2002.
Graves et al., "Relationship between plasma morphine concentrations and pharmacologic effects in postoperative patients using patient-controlled analgesia," Clinical Pharmacy, vol. 4, pp. 41-47, Jan.-Feb. 1985.
Roberts et al., "Enterohepatic Circulation: Physiological, Pharmacokinetic and Clinical Implications," Clin. Pharmacokinet., vol. 41, Issue 10, pp. 751-790, 2002.
"Ascorbic acid," Wikipedia, http://en.wikipedia.org/wiki/Ascorbic_acid, accessed Jan. 23, 2014.
National Institute on Drug Abuse, "Prescription Medications," http://www.nida.nih.gov/drugpages/prescription.html, accessed on Jul. 15, 2008.
Brannan et al., "Affine Geometry," Geometry, $2^{nd}$ edition, p. 78, 2012.
Katikaneni et al., "Ethylcellulose matrix controlled release tablets of a water-soluble drug," International Journal of Pharmaceutics, vol. 123, pp. 119-125, 1995.
Bravo et al., "In-vitro studies of diclofenac sodium controlled-release from biopolymeric hydrophilic matrices," J. Pharmaceutical Science, vol. 5, No. 3, pp. 213-219 (2002).
The Condensed Chemical Dictionary, "mixture," 9th edition, p. 584 (1977).
Giunchedi et al., "Hydrophilic matrices for the extended release of a model drug exhibiting pH-dependent solubility," International Journal of Pharmaceutics, vol. 85, pp. 141-147 (1992).
Hoshi et al., Cellulose and its Derivatives, pp. 24-25 (1992).
Miyazaki et al., "In situ-gelling gellan formulations as vehicles for oral drug delivery," J. Control Release, vol. 60, pp. 287-295 (1999).
Rowe et al., "Glycerin," Handbook of Pharmaceutical Excipients, Pharmaceutical Presse, $4^{th}$ edition, pp. 257-258 (2003).
www.wikipedia.org, web page on phosphoric acid, http://en.wikipedia.org/wiki/Phosphoric_acid, May 8, 2007.
Yamakita et al., "In Vitro/in Vivo Evaluation of Two Series of TA5707F Controlled Release Matrix Tablets Prepared with Hydroxypropyl Methyl Cellulose Derivatives with Entero-Soluble or Gel-Formation Properties," Biol. Pharm. Bull, vol. 18, No. 10, pp. 1409-1416 (1995).
Wikipedia, "Phosphoric Acid," http://en.wikipedia.org/wiki/Phosphoric_acid downloaded May 10, 2012.
Packer et al., "Molecular Aspects of a-Tocotrienol Antioxidant Action and Cell Signaling," Journal of Nutrition, vol. 131, No. 2, pp. 369S-373S, 2001.
Marvola et al., "Enteric polymers as binders and coating materials in multiple-unit site-specific drug delivery systems," European Journal of Pharmaceutical Sciences, vol. 7, pp. 259-267, 1999.
Dubbs et al., "Solubility of Vitamin E (α-Tocopherol) and Vitamin $K_3$ (Menadione) in Ethanol-Water Mixture," J. Chem. Eng. Data, vol. 43, pp. 590-591, 1998.
Merck Index ($9^{th}$ ed.) Entry No. 9681 for Vitamin E, p. 1290, 1976.
Varshosaz et al., "Use of enteric polymers for production of microspheres by extrusion-spheronization," Pharmaceutica Acta Helvetiae, vol. 72, pp. 145-152. 1997.
Wanka et al., "Phase Diagrams and Aggregation Behavior of Poly(oxyethylene)-Poly(oxypropylene)-Poly(oxyethylene) Triblock Copolymers in Aqueous Solutions," Macromolecules, vol. 27, pp. 4145-4159, 1994.
National Institute on Drug Abuse, "Monitoring the Future: National Results on Adolescent Drug Use," http://www.samhsa.gov, May 2009.
Notice of Allowance issued on May 2, 2014 in U.S. Appl. No. 12/602,953 (U.S. Pat. No. 8,821,928).

(56) References Cited

OTHER PUBLICATIONS

Office Action issued on Dec. 19, 2013 in U.S. Appl. No. 12/602,953 (U.S. Pat. No. 8,821,928).
Office Action issued on Mar. 7, 2013 in U.S. Appl. No. 12/602,953 (U.S. Pat. No. 8,821,928).
Notice of Allowance issued on Jul. 24, 2013 in U.S. Appl. No. 12/701,429 (U.S. Pat. No. 8,603,526).
Office Action issued on Oct. 17, 2012 in U.S. Appl. No. 12/701,429 (U.S. Pat. No. 8,603,526).
Office Action issued on Sep. 9, 2013 in U.S. Appl. No. 12/823,067 (U.S. Pat. No. 8,563,038).
Notice of Allowance issued on Jun. 11, 2013 in U.S. Appl. No. 12/823,067 (U.S. Pat. No. 8,563,038).
European Search Report issued on Apr. 11, 2011 in application No. EP 10 18 1692 (corresponding to US 2007/003617).
Kais Group, "Hydrogentated Palm Kernel Oil," http://kaisgroup.us/our-products/palm-oil-products/hydrogentated-palm-kernel-oil. Published 2011.
Soy Info Center, "A Special Report on the History of Soy Oil, Soybean Meal & Modern Soy Protein Products," http://soyinfocenter.com/HSS/hydrogenation2.php, published 2007.
Polysciences, Inc., "Monomers & Polymers," http://www.polysciences.com/Catalog/Department/Product/98/categoryid-298/productid--422/, published Apr. 3, 2004.
Krogel et al., "Pulsatile Drug Release from an Insoluble Capsule Body Controlled by an Erodible Plug," Pharmaceutical Research, vol. 15, No. 3, pp. 474-481, 1998.
Office Action issued on Jan. 20, 2015 in U.S. Appl. No. 13/933,053 (US 2014/0010873).
Notice of Allowance issued on Jan. 20, 2015 in U.S. Appl. No. 13/928,135 (U.S. Pat. No. 9,023,394).
Notice of Allowance issued on Jan. 23, 2015 in U.S. Appl. No. 12/701,248 (U.S. Pat. No. 9,005,660).
Office Action issued on Feb. 25, 2015 in U.S. Appl. No. 13/974,689 (US 2014/0120164).
Office Action issued on Oct. 29, 2015 in U.S. Appl. No. 14/331,833 (US 2015/0037417).
Office Action issued on Mar. 6, 2015 in U.S. Appl. No. 14/331,833 (US 2015/0037417).
Notice of Allowance issued on Apr. 6, 2015 in U.S. Appl. No. 14/249,965 (U.S. Pat. No. 9,044,402).
Office Action issued on Apr. 24, 2015 in U.S. Appl. No. 11/915,655 (US 2009/0274759).
Office Action issued on Jun. 4, 2015 in U.S. Appl. No. 12/523,045 (US 2010/0291205).
Notice of Allowance issued on Jun. 23, 2015 in U.S. Appl. No. 14/062,719 (U.S. Pat. No. 9,168,228).
Office Action issued on Jul. 29, 2015 in U.S. Appl. No. 14/496,561 (US 2015/0079150).
Office Action issued on Oct. 20, 2015 in U.S. Appl. No. 14/656,016 (US 2015/0313997).
Office Action issued on Dec. 7, 2015 in U.S. Appl. No. 11/915,655 (US 2009/0274759).
Office Action issued on Jun. 23, 2016 in U.S. Appl. No. 13/933,053 (US 2014/0010873).
Office Action issued on Dec. 4, 2015 in U.S. Appl. No. 13/933,053 (US 2014/0010873).
Office Action issued on Jan. 8, 2016 in U.S. Appl. No. 12/523,045 (US 2010/0291205).
Office Action issued on Jun. 22, 2016 in U.S. Appl. No. 14/560,579 (US 2015/0150812).
Office Action issued on Jan. 12, 2016 in U.S. Appl. No. 14/560,579 (US 2015/0150812).
Notice of Allowance issued on Feb. 9, 2016 in U.S. Appl. No. 14/656,016 (U.S. Pat. No. 9,358,295).
Notice of Allowance issued on Feb. 12, 2016 in U.S. Appl. No. 14/496,561 (U.S. Pat. No. 9,375,428).
Dontula et al., "Model Elastic Liquids with Water-Soluble Polymers," AIChE Journal, vol. 44, No. 6, pp. 1247-1255, Jun. 1998.
Office Action issued on Feb. 22, 2016 in U.S. Appl. No. 13/974,689 (US 2014-0120164).
Office Action issued on Jul. 11, 2016 in U.S. Appl. No. 12/523,045 (US 2014/0120164).
Office Action issued on Jul. 22, 2016 in U.S. Appl. No. 14/331,833 (US 2015/0037417).
Notice of Allowance issued on Jul. 15, 2016 in U.S. Appl. No. 14/859,800 (US 2016/0074332).
Office Action issued on Jul. 25, 2016 in U.S. Appl. No. 13/974,689 (US 2014/0120164).

* cited by examiner

- Burst-lag-burst
- Burst: 1 – 100 % in less than 1 h
- Lag: less than 10 % (5 %) in a duration of 1 to 10 h
- Burst: 1 – 100 % in less than 1 h

- Burst-controlled-burst
- Burst: 1 – 100 % in less than 1 h
- controlled: 0.1 %/h – 30 %/h (50 %/h) in a duration of 1 to 10 h
- Burst: 1 – 100 % in less than 1 h

•Burst-controlled
•Burst: 1 – 99 % in less than 1 h
•controlled: 0.1 %/h – 30 %/h (50 %/h) in a duration of 1 to 10 h

- Controlled-burst
- Controlled: 0.1 %/h – 30 %/h (50 %/h) in a duration of 1 to 10 h
- Burst: 1 – 100 % in less than 1 h

Lag-burst
• Lag: less than 10 % (5 %) in a duration of 1 to 10 h
• Burst: 1 – 100 % in less than 1 h

• Lag-burst-lag-burst etc

- Controlled-controlled
- Controlled: 0.1 %/h – 30 %/h (50 %/h) in a duration of 1 to 10 h
- Controlled: 0.1 %/h – 30 %/h (50 %/h) in a duration of 1 to 10 h

- Controlled-controlled
- Controlled: 0.1 %/h – 30 %/h (50 %/h) in a duration of 1 to 10 h
- Controlled: 0.1 %/h – 30 %/h (50 %/h) in a duration of 1 to 10 h

US 9,642,809 B2

CONTROLLED RELEASE PHARMACEUTICAL COMPOSITIONS FOR PROLONGED EFFECT

CROSS-REFERENCE TO RELATED APPLICATIONS

This application is a continuation of U.S. patent application Ser. No. 12/602,953, filed Jun. 7, 2010, which is a National Stage of International Application No. PCT/EP2002/056910, filed Jun. 4, 2008, which claims the benefit under 35 U.S.C. §119(e) of U.S. Provisional Patent Application No. 60/941,848, filed Jun. 4, 2007, these applications are incorporated herein by reference in their entireties.

INTRODUCTION

The present invention relates to a technology that is especially suitable for designing oral pharmaceutical compositions that are useful in the treatment of diseases where absorption e.g. takes place over a large part of the gastrointestinal tract (e.g. in stomach, the small intestine as well as in the colon). Accordingly, the present invention provides a composition that enables a first release of the active substance (e.g. a burst or a controlled release) followed by a second release of the same active substance (e.g. a burst or a controlled release). The design of the composition takes into account the fact that different conditions are present in different parts of the gastrointestinal system. Thus, e.g. in the colon, the surface area of the mucosal surface through which the active substance must be absorbed is much smaller than in the small intestine and, moreover, the amount of body liquid present is also much smaller. The compositions of the present invention may also be suitable in the treatment of diseases in which circadian rhythm or biorhythm effects can influence the condition being treated or when an effective therapy is desired e.g. in the early morning before awakening or when the active substance have a narrow absorption window or the absorption is poor e.g. in the colon or for local effect/treatment. Some physiologically active substances are periodically produced in vivo at certain time intervals and it may accordingly be desirable to administer such substances in a controlled release formulation which periodically releases the active substance at predetermined time intervals to obtain certain fluctuation in the drug level which may be desirable in connection with the treatment of various diseases. The present technology provides a means for designing such compositions and moreover, such compositions may be combined with an initiated burst release and/or zero order controlled release of the active substance.

BACKGROUND OF THE INVENTION

In the past decades many controlled release technologies have appeared. However, for drug substances that can be absorbed through many segments of the gastrointestinal (GI) tract, there is still a need for developing compositions that enable sufficient absorption of the drug substance over broader range of segment of the gastrointestinal (GI) tract in order to enable a less frequent dosage of the drug and/or in order to avoid excretion of unabsorbed drug via the faeces.

Pharmacodynamics and pharmacokinetics challenges might enforce the need for special release patters (such as paracetamol in which the first pass metabolism makes it difficult to make a constant release unit work). Furthermore, the passage of material through the gastrointestinal tract is carefully controlled by several mechanisms. This "housekeeping" (intestinal peristalsis) might lead to anomalies in the effect of solid oral dosage forms which might be compensated by the formulation.

Furthermore, the active substance may exert its effect locally in the colon or other parts of the gastrointestinal system, such as for treatment of cancer, inflammation, gastrointestinal diseases and treatment with anthelmintic agents.

DETAILED DESCRIPTION OF THE INVENTION

Figure 1:
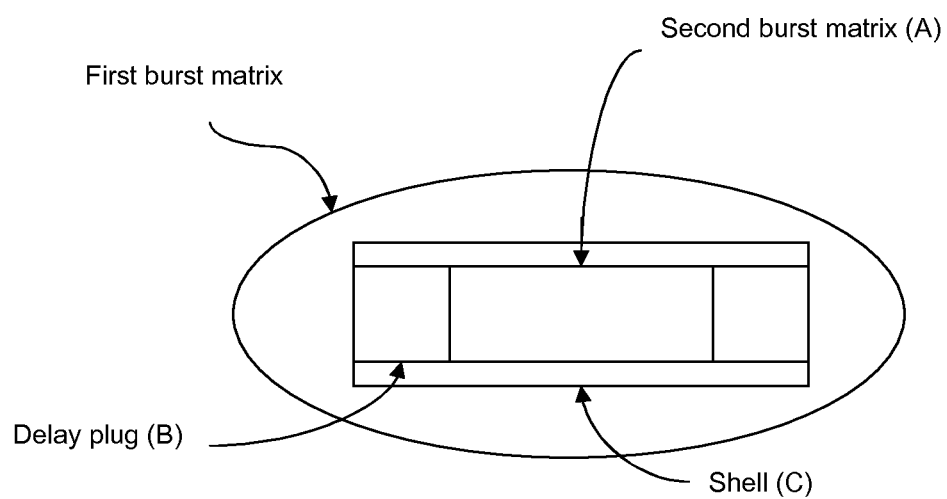
FIG. 1, illustrate double burst unit, with a delay between the two bursts.

However, to the best of our knowledge there is still a need to develop a technology that enables preparation of pharmaceutical compositions useful for the above-mentioned therapies (including chronotherapy) in a relatively simple manner, preferably in a procedure involving relatively few steps and relatively simple equipment, and in an economical feasible manner. Moreover, it is desired to obtain a technology that is suitable for use for many different drug substances, i.e. a technology that is relatively flexible with respect to how to obtain a desired release pattern of the active substance. Thus, a relatively simple technology is desired that enables combination of e.g. delayed release followed by controlled (extended) release, delayed release followed by immediate release, burst release followed by delayed release followed by either controlled or immediate release, burst release followed by controlled release, controlled release followed by controlled release or immediate release. A further advantage could be a technology that enables variation in the design in a relatively easy manner such that the composition also includes e.g. a burst dose or controlled release dose (of different active substance).

The present invention provides such a technology. The technology is a further development of the Applicant's proprietary technology described in WO 99/51208, WO 03/24426, WO 03/24429, WO 03/24430, WO 2004/41252, WO 2004/84869, WO 2005/107713, WO2006/128471 that is based on matrix compositions comprising a substantially water soluble and/or crystalline polymer. Moreover it is a further development of the technology described in WO 2006/128471 that relates to a composition having an inner part of a composition that liquefies at body temperature sandwiched between two matrix compositions. In this manner a delay is obtained with respect to release of the active substance contained in the inner part and once, the matrix compositions are eroded away, the liquefied inner part is designed to flow out of the shell that surrounds the cylindrical part of a cylindrical shaped composition (i.e. the shell (or coating) covers the cylindrical surface, but not the end surfaces). In this manner the active substance in the inner part should be immediately released once the matrix parts are eroded. However, in some situations the present inventors have observed that the outflow of the liquefied inner part is not that easy, e.g. in situations where the composition reaches the large intestine or the colon. In these situations, a limited amount of water is present and, accordingly, the flow is limited and moreover, in the colon lumps of faeces may block the open ends of the shell leading to limited release of the active substance. Accordingly, the present inventors have developed compositions that substantially overcome the above-mentioned problems.

The present invention provides an extended release composition for prolonged effect and a way to ensure prolonged effect e.g. once daily administration is to ensure optimal absorption of the active substance though the gastrointestinal tract i.e. from the stomach to rectum.

When absorption of the active substance is limited or do not proceed substantially good in the distal part of the small intestine and/or in colon a relatively fast release of the active substance is an advantage when the controlled release composition enter this part of the tract and especially in those cases where the active substance is poorly absorbed in the distal part of the small intestine or in ascending and first part of the transverse colon. A release composition having controlled release follow by immediate release behavior is desirable for optimal absorption and effect.

A composition having controlled release follow by immediate release of the active substance is also an advantage when the active substance is poorly soluble and therefore requires a substantial amount of water/fluid to dissolve in the distal part of the small intestine before it enters colon for absorption.

If absorption of the active substance is unchanged through the gastrointestinal tract a better absorption of the active substance in the colon can be achieved if a relatively fast release of controlled release multiple units is released from the controlled release composition in the distal part of the small intestine to prevent limited absorption of the active substance due to block of the open ends of the shell in the colon lumps of faeces. A composition having controlled release follow by controlled release behavior in the shape of controlled release multiple units is desirable.

The opposite is the case (i.e. a composition having burst release follow by delay and/or controlled release behavior) if there is absorption problem in the first part of the gastrointestinal tract e.g. the stomach. It is also the case if fast effect follow by maintenance of the effect is desirable.

Controlling the release of the active substance from the composition and thereby the absorption of the active substance, makes it possible to control the blood level of the active substance and maintain the concentration within the therapeutic range over an extended period of time without high peak trough fluctuation which improve the therapeutic effect and reduced incidence of side effects.

It is an object of certain embodiments of the present invention to provide bioavailable formulations suitable for once daily administration which substantially improve efficiency and quality of the treatment.

It is an object of certain embodiments of the present invention to provide oral controlled release composition suitable for once daily administration which provide an early onset of therapeutic effect and which, after rising to a maximum concentration during the dosage interval, provide a relatively flat plasma profile, meaning that the plasma level pf the active substance provides a peak trough ratio of about 0.5 to about 1.0, and which provides effective treatment.

Another advantage relating to the present invention is the possibility of administering the two active substances at the same time and advantageous in the same pharmaceutical composition. However, as such a combination treatment is expected to have optimized effect with respect to each of the two substances at different points in time it is important to incorporate the two active substances in the composition in such a manner that i) it is possible to incorporate a suitable amount of each active substance (notably an amount corresponding to a daily dose and should be present in a specific weight ratio that is optimized with respect to therapeutic effect), ii) it is possible to avoid any negative interaction of the two active substances in the composition, iii) it is possible to avoid an excessive degree of oxidation of the active substances (however, levels corresponding to normally accepted levels are acceptable), iii) it is possible to obtain release patterns of both substances that are optimized with respect to therapeutic effect (see iv)-vi) for more specific details), iv) it is possible to control the release pattern of the two active substances from the composition in such a manner that the release of S1 is independent of the release of S2; this applies for the release mechanism as well as the release rate and time for 80-100% w/w release, v) it is possible to e.g. obtain a zero order release for one or both of the active substance, zero order release for one of the active substances and another order of release for the other active substance or the like, vi) it is possible to obtain e.g. a relatively slow release followed by a faster release of one of the active substance without impact on the release of the other active substance, and/or vii) it is possible to use a formulation technique that potentially may improve the bioavailability of at least one of the active substances and, preferably, of both of the active substance (due to the fact that both active substances generally have a low bioavailability).

In one aspect, the present invention relates to a layered pharmaceutical composition comprising A) a solid inner layer comprising
i) an active substance, and
ii) one or more disintegrants/exploding agents, one of more effervescent agents or a mixture thereof.

The solid inner layer being sandwiched between two outer layers B1) and B2), each outer layer comprising
iii) a substantially water soluble and/or crystalline polymer or a mixture of substantially water soluble and/or crystalline polymers, the polymer being a polyglycol in the form of one of a) a homopolymer having a MW of at least about 100,000 daltons, and b) a copolymer having a MW of at least about 2,000 daltons, or a mixture thereof, and
iv) an active substance, which is the same as in said solid inner layer A), and layer A being different from layer B, the layered composition being coated with a coating C) that has at least one opening exposing at least one surface of said outer layer, the coating being substantially insoluble in and impermeable to fluids and comprising a polymer, and the composition having a cylindrical form optionally with one or more tapered ends, wherein the ratio between the surface area of one end surface of the cylinder and the length of the cylinder is in a range of from 0.02 to 45 mm.

In a specific embodiment of the present invention, layer A) comprises
v) a substantially water soluble and/or crystalline polymer or a mixture of substantially water soluble and/or crystalline polymers, the polymer being a polyglycol in the from of one of c) a homopolymer having a MW of at the most about 16,000 daltons, and d) a copolymer having a MW of at the most about 30,000 daltons.

As mentioned above, the present invention is a further development of the Applicant's proprietary technology, namely preparation of pharmaceutical compositions based on a water soluble and/or crystalline polymer or mixture of such polymers involving a step of melting or softening the polymer by means of injection moulding, extrusion or the like. The injection moulding technique has the advantage of simultaneous mixing and heating the components during increased pressure in a one step procedure without exposure to air and moisture because the injection moulding is performed in a single closed compartment from the time a blend of the components has entered the machine to the final pharmaceutical units are ejected ready for packaging. More details regarding the preparation method are given below and in the experimental section.

As appears from the above, the invention concerns a layered pharmaceutical composition having an inner layer with the active substance sandwiched between two lag-time providing layers, i.e. layers that enable a delay in the release of the active substance contained in the inner layer. The layered composition is coated in such a manner that only a surface layer from the outer layer(s) is free of coating material. In a preferred embodiment, the composition has a cylindrical shape and then the cylindrical surface is coated leaving one or two of the end surfaces without any coating (normally both end surfaces are without coating). In order to ensure a sufficient release of the active substance contained in layer A) of the composition, the present inventor's have found that the following two properties are important, namely the geometry and dimensions of the composition and the present of a disintegrant and/or an effervescent agent (or couple). The first parameter ensures that the distance to travel for the inner layer is not too big compared with the size of the opening (i.e. the end surface) and the other one ensures that a driving force activates the mobility of the active substance in layer A) when it comes into contact with a body liquid. Moreover, as will be explained below, a further parameter has also a positive influence in order to enable a release of the active substance from layer A), namely the incorporation of the active substance in readily flowable multiple units.

Geometry

The lag-time mechanisms (and the release mechanics of any active substance contained in the outer layers) described above depends on the geometry of the composition. For example erosion based release from a matrix depends on the exposed area of the matrix. In this case the area may be manipulated by employment of a coat that is not subject to erosion and thus covering the areas of the matrix that hence will not be a releasing site. In particular, a cylindrical composition with the two ends exposing the eroding matrix will give rise to zero order release because the releasing area is constant.

The geometric form of the composition is very important for the obtainment of the above-mentioned controlled release. Thus, in one embodiment of the invention, the pharmaceutical composition has a geometric shape, which enables a substantially constant surface area to become exposed during erosion of the matrix. As explained above, the present inventors have found that the proportions between the surface area of the end surface and the length of the cylinder are important in order to ensure that the active substance (or, if relevant, of the multiple unit formulation containing the active substance) can be released from the inner part. Specific examples appear from the examples herein. In general, the following ratio between the surface area of one end surface and the length of the cylinder has been found to be suitable in order to ensure a proper release: from about 0.02 to about 45 mm such as, e.g., from about 0.1 to about 10 mm or from about 0.5 to about 8 mm. In most cases, the composition of the invention has two end surfaces, and, if the ratio is calculated on the total surface area of the end surfaces, then the ratio is from about 0.02 to about 85 mm such as, e.g., from about 0.1 to about 10 mm or from about 1.3 to about 14 mm.

In a specific example, the compositions employed are coated in such a manner that the surface has a substantially constant or controlled surface area during release or erosion. In the present context controlled surface area relates to a predetermined surface area typically predicted from the shape of the coat of the unit dosage system. It may have a simple uniform cylindrical shape or the cylindrical form can have one or more tapered ends in order to decrease (or increase) the initial release period.

As another example, in diffusion based systems the release will furthermore depend on the thickness of the diffusion layer and in this case the release will depend both on the diffusion area and thickness of the diffusion system.

As yet another example the release mechanism of dissolving/solubilization also depend on the releasing area and the release rate may be controlled by covering parts of the releasing matrix by a coat. Controlling the coverage of the matrix by the coat hence refers to covering from 0 to 100% of the matrix by a coat.

Inner Layer A)

The object of the present invention is to design a composition comprising an active substance that is released after a certain period of time (e.g. burst release followed by controlled release, controlled release followed by burst release, controlled release followed by controlled release, burst release followed by burst release). However, as explained above one of the problems the inventors were faced with was how to ensure that the inner layer exits the shell (coating) once the outer layers have disappeared. As explained above, two parameters are of importance. Firstly, incorporation of a pharmaceutically acceptable excipient that aids in disintegrating the inner layer seems to be of relevance. Accordingly, the inner layer may also contain one or more disintegration/exploding agents, one of more effervescent agents or a mixture thereof.

It is important to note that once the inner layer is "released" from the shell and brought into direct contact with an aqueous medium (e.g. the gastrointestinal fluids after oral administration) then various types of release of the active substance can be obtained ranging from immediate release (e.g. the active substance is readily available for release such as e.g. present in dissolved form in a form that is easily dissolvable) to controlled release (e.g. in the form of pellets designed to controlled release or other well-known types of formulations including beads, flakes, mini-tablets, granules, microspheres, nanoparticles, crystals or the like).

As the shell (coating) has properties that ensure exposure of a well-defined (normally constant or substantially constant) surface area of the composition to the surrounding medium so that the outer layer(s) can be eroded with a constant rate until the layer(s) are eroded away, it is important that the shell remains intact until the outer layer(s) have eroded. This normally means that the shell is left when the inner layer is the only layer left of the composition. Accordingly, the difficulty of the problem is to ensure a "release" of the inner layer from the shell or, in other words, a delivery of the inner layer material from the inside of the shell to the outside.

Disintegrants, Swelling Agents, Exploding Agents, Effervescent Agents

The inner layer may be formulated such that it disintegrates upon contact with water. The disintegration may be by a mechanism of exploding, by effervescence, by swelling, by rapid erosion or combinations thereof. The disintegration by exploding may be governed by rapid water influx into- and swelling of one or several of the matrix components leading to a collapse of the inner layer structure (normally a matrix structure) such that the active substance may be released or such that e.g. multiple units, crystals etc. containing the active substance may be released. The multiple units may be designed as quick release (/burst release/immediate release) multiple units or controlled release multiple units for release of the active substance in the small intestine and/or colon.

The disintegration may be by means of swelling. The inner layer comprises an excipient (here a disintegrant), which swells rapidly upon contact with aqueous media makes it possible to push the active substance or active multiple units out of the shell. Preferably, the detachment of the active matrix should be in smaller lumps with a large area-to-volume ratio.

As mentioned above, the "release" of the inner layer (or delivery of the inner layer material to the outside of the shell) may be aided by incorporation of e.g. a disintegrant also called swelling and/or exploding agent. A disintegrant typically swells upon contact with water and enable disruption of the inner layer to agglomerates or particle. Examples of suitable disintegrants include Sodium starch glycolate, Povidone, Sodium alginate, Alginic acid, Calcium alginate, Carboxymethylcellulose calcium, Carboxymethylcellulose sodium, Powdered cellulose, Chitosan, Croscarmellose sodium, Crospovidone, Hydroxypropyl starch, Hydroxypropyl cellulose low-substituted, Magnesium aluminium silicate, Methylcellulose, Microcrystalline cellulose, pregelatinized starch, Docusae sodium, Guar gum, Polacrilin potassium.

The disintegration may also be due to an effervescent effect, whereby gas such as $CO_2$ is released from the inner layer upon contact with water and a rapid dissolving system is formed. The formation of gas bubbles will push the inner layer out in small lumps and thereby manifold increase the exposed area of the inner layer (e.g. containing active substance, active multiple units or the like) to the medium. For example sodium bicarbonate releases $CO_2$ by reaction with water in an acidic environment. It is possible to develop a more pH-robust formulation by adding an acidic excipient to the formulation. The rate of which the gas formation occurs depends on the rate of hydration and diffusion of water into the matrix.

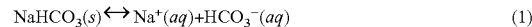

$$NaHCO_3(s) \leftrightarrow Na^+(aq) + HCO_3^-(aq) \quad (1)$$

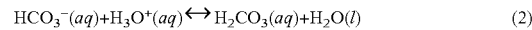

$$HCO_3^-(aq) + H_3O^+(aq) \leftrightarrow H_2CO_3(aq) + H_2O(l) \quad (2)$$

$$H_2CO_3(aq) \leftrightarrow CO_2(g) + H_2O(l) \quad (3)$$

"Release" of the inner layer may also take place by means of gas formation using effervescent substances or effervescent couples. Examples of suitable effervescent agent include Effer-Soda, Citric acid, monohydrate, Dextrates, Fumaric acid, Potassium bicarbonate, Sodium bicarbonate, Sodium citrate dehydrate, Tartaric acid.

Disintegration may also take place by rapid erosion, which can be obtained by employing for example short chained polymers in the matrix, such that the matrix is readily wetted and dissolved exposing either the active multiple units or the matrix component(s) containing the active substance.

Furthermore, disintegration might be facilitated by facilitating water transport through the matrix by for example open pores.

In order to ensure suitable properties of the inner layer A, the inner layer A) without B) and C) disintegrates within at the most 60 min such as, e.g., at the most about 30 min or at the most about 15 min, when subjected to a disintegration test according to Ph. Eur.

Normally, the concentration of the one or more disintegrants, exploding agent and/or effervescent agent in the inner layer is from about 5% w/w to about 80% w/w such as, e.g., from about 10% w/w to about 70% w/w, from about 15% w/w to about 60% w/w or from about 20% w/w to about 50% w/w.

One or more pharmaceutically acceptable excipients or additives may also be present in inner layer A) (see the section "Pharmaceutically acceptable excipients")

The inner layer A) may also contain a polymer. The same applies to the outer layers B) and in the following is given a general description of suitable polymers for the two (three) layers A) and B). It is important to note that in those cases where the active substance in layer A) is present in the form of multiple units, then the multiple units may be in the form of e.g. pellets, beads or the like, and in such cases one or more polymer may be employed in the preparation of the multiple units. In such cases, the polymers mentioned in the following are suitable and such polymers may appropriately be of the same nature as the polymers employed in the B) layers. In contrast hereto, the layer A may also contain a polymeric substance (as a dispersion medium for the active substance), but in this case, it is important that the polymeric substance has different properties from that used in layer B). To differentiate between the individual polymers, the notation "matrix polymer" is used to indicate that the polymer is suitable for use in layer B) and in multiple units, whereas the notation "layer A polymer" is used to indicate that the polymer is suitable for use as a dispersion medium or excipient in layer A.

Suitable polymers for use according to the invention typically comprises a polyglycol, e.g. in the form of a homopolymer and/or a copolymer. In a specific embodiment the polymer is substantially water soluble, thermoplastic, crystalline, semi-crystalline or amorphous or a mixture of substantially water soluble, crystalline, semi-crystalline or amorphous polymers. Suitable polymers for use in a composition according to the invention are polyethylene glycols, including derivatives such as mono and dimethoxypolyethylene glycols (mPEGs) polyethylene oxides and/or block copolymers of ethylene oxide and propylene oxide.

Polyethylene glycols (PEGs) are linear polydisperse polymers composed of repeating units of ethylene glycol. Their chemical formula is $HOCH_2[CH_2OCH_2]_mCH_2OH$ where m represents the average number of repeating units. Alternatively, the general formula $H[OCH_2CH_2]_nOH$ may be used to represent polyethylene glycol, where n is a number m in the previous formula+1. See the structural presentations of polyethylene glycol below. n is the average number of oxyethylene groups. n equals m+1.

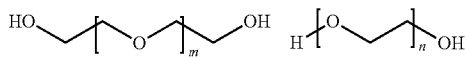

Polyethylene oxides (PEOs) are linear polydisperse non-ionic polymers composed of repeating units of ethylene oxide. Their chemical formula is $HO[CH_2CH_2O]_nH$ where n represents the average number of oxyethylene groups. See the structural presentation of polyethylene oxide below. n is the average number of oxyethylene groups. Depending on preparation method high molecular weigh PEO may have one terminal methyl group.

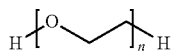

Polyethylene glycols are mixtures of addition of ethylene glycol. In general PEG refers to polymers chains with molecular weights below 20,000, while PEO refers to higher molecular weights polymers. However, because of the similarities between PEO and PEG, the terms are often used interchangeably for the same compound.

Poloxamers are copolymers or block copolymers and are a range of non-ionic surfactants of polyethylene glycol (PEG) and polypropylene glycol (PPG).

In chemical abstracts Diol EO/PO block copolymers are described under the scientific name—hydroxy-hydroxypoly(oxyethylene)poly(oxypropylene)-poly(oxyethylene)-block copolymer in combination with the CAS register number.

In specific embodiments a suitable poloxamer for use in a composition of the invention has a HLB value of at least about 18 such as, e.g., at least about 20. The mean molecular weight of a suitable poloxamer is typically at least about 2,000.

Mixtures of PEO with different average molecular weights can be used in order to obtain a PEO with a desirable average molecular weight. The same applies to PEG.

The polymer has a melting point higher than the body temperature of the human in which the composition is to be used. Thus, the polymer(s) employed in the matrix composition will suitably have a melting point of about 20-120° C. such as, e.g. from about 30 to about 100° C. or from about 40 to about 80° C.

In addition to a polymer of a polyglycol type as described above other polymers may be suitable for use in a pharmaceutical composition provided that the solubility and/or release rate of the active substance from the composition in water is higher than or equal to the solubility of the matrix in 40% w/w ethanol in water. Thus, in other embodiments of the invention, the polymer or an additional polymer to the polyglycol may be selected from one or more of the following polymers: modified or unmodified water soluble natural polymers such as glucomannan, galactan, glucan, polygalacturonic acid, polyxylane, polygalactomannans, rhamnogalacturonan, polyxyloglycan, arabinogalactan, and starch, cellulose, chitosan, alginate, fibrin, collagen, gelatin, hyaluronic acid, amylopectin, pectin including low methylated or methoxylated pectins, dextran and fatty acids and alcohols; synthetic polymers such as polyvinylpyrrolidone (PVP), PVA, PVB, Eudragit L methyl ester, Eudragit L, Eudragit RL, Eudragit E, Eudragit S, PHPV, PHA, PCL, PLGA and PLA; and hydrogels made from the polymers or combined polymers mentioned above and or from polymers originated from: HEMA, HEEMA, MEMA, MEEMA, EDGMA, NVP, VAc, AA, acrylamide, MAA, HPMA, PEGA, PEGMA, PEGDMA, PEGDA, and PEGDMA.

Polymers in Layer A)

In one embodiment of the invention, layer A) comprises v) a substantially water soluble and/or crystalline polymer or a mixture of substantially water soluble and/or crystalline polymers, the polymer being a polyglycol in the from of one of c) a homopolymer having a MW of at the most about 16,000 daltons, and d) a copolymer having a MW of at the most about 30,000 daltons.

In specific embodiments, the polymer comprises a homopolymer having a MW of at least about 1,000 daltons such as, e.g., a homopolymer having a MW in a range from about 1,000 to about 15,000 daltons, from about 1,000 to about 12,000 daltons, from about 1,500 to about 10,000 daltons, from about 1,500 to about 8,000 daltons.

The polymer may also comprise a co-polymer having a MW of at the most about 25,000 daltons such as, e.g., at the most about 20,000 daltons, at the most about 15,000 daltons, at the most about 10,000 daltons, at the most about 5,000 daltons, at the most about 2,000 daltons.

Polymers in Layers B) or Used in Multiple Units Containing the Active Substance and Incorporated in Layer A)

Polyethylene glycols and/or polyethylene oxides, which are suitable for use in the matrix composition are those having a molecular weights of from about 20,000 daltons, such as, e.g., from about 20,000 to about 700,000 daltons, from about 20,000 to about 600,000 daltons, from about 35,000 to about 500,000 daltons, from about 35,000 to about 400,000 daltons, from about 35,000 to about 300,000 daltons, from about 50,000 to about 300,000 daltons, such as, e.g. about 35,000 daltons, about 50,000 daltons, about 75,000 daltons, about 100,000 daltons, about 150,000 daltons, about 200,000 daltons, about 250,000 daltons, about 300,000 daltons or about 400,000 daltons.

In a specific embodiment the matrix polymer is a polyethylene oxide or a polyethylene glycol that has a molecular weight of about 20,000 daltons, about 35,000 daltons, about 50,000 daltons, about 100,000 daltons, about 200,000 daltons, about 300,000 daltons and about 400,000 daltons. PEG is commercially available with average molecular weights up to 35 000. PEO is commercially available with average molecular weights up to 8,000,000. In specific embodiment, the polymer is a PEO having a molecular weight of at least about 100,000 such as, e.g., from about 100,000 to about 8,000,000, from about 100,000 to about 7,000,000, from about 100,000 to about 5,000,000, from about 100,000 to about 4,000,000, from about 100,000 to about 2,000,000, from about 100,000 to about 1,000,000, form about 100,000 to about 900,000. When PEO is employed with a molecular weight in the lower end, the PEO typically has a molecular weight as mentioned in the preceding paragraph. Commercially available PEOs with a molecular weight in the higher end have typically the following molecular weights: about 900,000, about 1,000,000, about 2,000,000, about 4,000,000, about 5,000,000, about 7,000,000, about 8,000,000. It should be noted that when PEO with a molecular weight of up to about 700,000 is used, it is possible to obtain a matrix composition (prepared e.g. by injection molding) that releases the active substance contained in the matrix with a zero order release (erosion of a constant surface area). However, the applicant has indications that employment of PEO with a molecular weight of 1,000,000 or higher leads to a slower release and a different release pattern. However, zero order release may not always be required from the layer B), but a slow release may be important. In such cases, the high molecular weight PEOs are suitable for use in a composition of the invention.

Typical block copolymers of ethylene oxide and propylene oxide have a molecular weight of from about 2,000 daltons, typically about 3,000 to about 30,000 daltons such as, e.g. from about 4,000 to about 15,000 daltons. If the copolymer is the sole thermoplastic polymer present in the composition it must not bee too brittle in order to avoid abuse by crushing of the composition, i.e. it must have an HLB value of about 18 to about 24.

Concentration of Polymers in Layer A and/or B

The polymer may also be a mixture of the above-mentioned polymers. Normally, the concentration of the polymer(s) in layer A) when applied is from about 1 to about 99.9% w/w dependent on the desired release properties relating to the release of the active substance from the inner layer. In those cases where a relative fast release of the active substance (or multiple units e.g. a pellet composition or the like containing the active substance) is desired or there is a relatively high concentration of active substance in layer A), a relative low concentration of the polymer may be of interest such as, e.g. from about 1 to about 30% w/w such as, e.g., from about 5 to about 25% w/w, from about 5 to about 20% w/w or from about 10 to about 20% w/w. In other cases, the concentration of the polymer in layer A) may be such as from about 10 to about 95% w/w, from about 15% to about 90% w/w, such as from 20 to 85%, such as from 30% to 85% from about 30 to about 99% w/w such as, e.g., from about 35 to about 95% w/w, from about 35 to about 90% w/w, from about 35 to about 85% w/w, from about 35 to about 80% w/w, from about 40 to about 75% w/w, from about 45 to about 70% w/w, from about 45 to about 65% w/w. from about 55 to about 85% w/w or from about 60 to about 85% w/w.

One or more polymers are typically present in a composition of the invention in a concentration amount of from 5 to 99.9% w/w such as from 10 to 95% such as from 15% to 90%, such as from 20 to 85%, such as from 30% to 85% calculated as w/w % of the composition.

In those cases, where mixture of polymers are present in the composition, the concentration of an individual polymer in the composition may typically be from about 0% to about 95% w/w such as, e.g., from about 0.5% to about 90% w/w, from about 1% to about 90% w/w, from about 5% to about 90% w/w, from about 10% to about 90% w/w, from about 10% to about 80% w/w, from about 10% to about 70% w/w, from about 10% to about 60%, from about 10% to about 50%, from about 15% to about 50% w/w, from about 15% to about 45% w/w, from about 15% to about 40% w/w, from about 20% to about 40% w/w, from about 20% to about 35% w/w or from about 20% to about 30% w/w. In specific embodiments, the concentration is even lower such as from about 1% to about 15% w/w or from about 5% to about 15% w/w.

The total concentration of the polymers (notably the sum of homo- and copolymers of the polyglycol type) in the composition is typically from about 5 to about 99.9% w/w such as from about 10 to about 95% w/w, from about 15% to about 90% w/w, such as from 20 to 85%, such as from 30% to 85% from about 30 to about 99% w/w such as, e.g., from about 35 to about 95% w/w, from about 35 to about 90% w/w, from about 35 to about 85% w/w, from about 35 to about 80% w/w, from about 40 to about 75% w/w, from about 45 to about 70% w/w, from about 45 to about 65% w/w. from about 55 to about 85% w/w or from about 60 to about 85% w/w. In specific embodiments (e.g. for burst layer (may be layer A) and/or layer B)), the concentration is even lower such as from about 5% to about 40% w/w or from about 5% to about 35% w/w.

The concentration of the polyglycol homopolymer is typically from about 0.5 to about 99.9% w/w such as from 5 to about 99.9% w/w, from about 0.5% to about 90% w/w, from about 1% to about 90% w/w, from about 5% to about 90% w/w, from about 20 to about 90% w/w, from about to about 90% w/w, and, in those cases where the homopolymer is the only thermoplastic polymer present in the composition, then the concentration is normally from about 50 to about 95% w/w such as, e.g. from about 55 to about 90% w/w, from about 60 to about 90%, from about 65 to about 90%, from about 70% to about 90% or from about 70 to about 85% w/w. In specific embodiments, the concentration is even lower such as from about 1% to about 15% w/w or from about 5% to about 15% w/w.

The concentration of the polyglycol copolymer, if present in combination with a polyglycol homopolymer, is typically from about 1 to about 60% w/w such as, e.g. from about 2.5 to about 50% w/w, from about 5 to about 45% w/w. If the copolymer is the sole thermoplastic polymer in the composition the concentration may be from about 5 to about 99.5% w/w such as those ranges described above and described for the homopolymer. In specific embodiments, the concentration is even lower such as from about 1% to about 15% w/w or from about 5% to about 15% w/w.

In embodiments where the outer layer matrix composition comprises a PEO and a poloxamer the weight ratio (PEO/poloxamer) is normally in a range from about 10:0.1 to about 0.1:10 such as, e.g., from about 10:1 to about 1:10, from about 5:1 to about 1:5 or from about 3:1 to about 1:3.

The one or more, the same or different active substance in the inner layer may be designed to various types of release once the inner layer is "released" from the shell.

In one embodiment of the invention, the inner layer contains the active substance incorporated into a multiple unit formulation or it may be present in the form of relatively large crystals (i.e. 100 µm or more).

Inner Layer—Active Substance in Multiple Units

As mentioned above, the active substance may be present in many forms in the inner layer. Thus, it may be present in dissolved form, e.g. dissolved in the ingredients of the inner layer such as in the form of a solid dispersion or solid solution. It may also be present in solid form e.g. in the form of particles or crystals of the active substance. Moreover, the active substance may be incorporated into a formulation before it is incorporation into the inner layer. Such formulations are described in the following including multiple units. In such a formulation, the active substance may be present in solid or dissolved form as well. The multiple units for use according to the invention may be crystals of an active substance, inert cores coated with active substance—inert cores like e.g. calcium alginate beads, cellulose spheres, charged resin spheres, glass beads, polystyrene spheres, sand silica beads or units, sodium hydroxide beads, sucrose spheres. Cores containing active substance like e.g. beads, pellets, flake, pieces, granules, granulates (also denoted agglomerates), spheres, tablets, especially minitablets etc.

The shape of the multiple units may be any suitable shape including a rounded or oval shape as well as a polygonal or rod-like or flake-like shape.

The mean particle size of the multiple units is at the most about 1400 μm. In particular embodiments, the particle size of the multiple units is at the most about 1200 μm such as, e.g., at the most about 1100 μm, at the most about 1000 μm, at the most about 900 μm, at the most about 800 μm, at the most about 750 μm, at the most about 700 μm, at the most about 650 μm, at the most about 600 μm, at the most about 550 μm or at the most about 500 μm; such as, e.g., from about 150 μm to about 1200 μm, from about 200 μm to about 1200 μm, from about 200 μm to about 1000 μm, from about 250 μm to about 800 μm or from about 300 μm to about 750 μm. In a specific embodiment of the invention the particle size of the multiple units is at the most about 500 μm to about 1000 μm, or from about 350 μm to about 500 μm. In some cases, the particle size of the multiple units may be even higher. Thus, in some cases the particle size may be at the most about 2 mm.

The release of the active substance may take place by diffusion by which the rate of release depends on several mechanisms, for example: the concentration difference between the matrix active substance concentration and the bulk concentration, the release surface area and the diffusion constant of the drug substance in the matrix. In special cases diffusion controlled release may be zero order.

Once the inner layer is exposed to the gastrointestinal fluids (or another aqueous medium) the release of the active substance may take place. In contrast to a release from a matrix that erodes (i.e. a matrix like the one of the outer layer), the release of the active substance from the inner layer may follow a kinetic that is different from a zero order release. The present formulation principle is designed to delay the release not necessarily to enable a zero order release or other types of release kinetics that are relevant when designing controlled or modified release compositions. However, the basic formulation principle of the present invention may be combined with known formulation principles e.g. if an active substance also is included in the matrix of the outer layer B), then this active substance can be released by zero order kinetics, i.e. in a controlled manner, and the active substance contained in the first fraction is released once exposed to the gastrointestinal fluids (or another aqueous medium) or in a controlled manner, but once the release of active substance or active multiple units from the first fraction starts it may be relatively fast.

Outer Layers B1) and B2)

The outer layers of a composition according to the invention are typically based on the matrix principle disclosed in WO 99/51208, WO 03/24426, WO 03/24429, WO 03/24430, WO 2004/41252, WO 2004/84869, WO 2005/107713, WO2006/128471 (to the same applicant). Such matrices have unique properties in that they erode, i.e. it does not disintegrate into smaller particles or conglomerates of particles upon exposure to the gastrointestinal fluid. Simplified, erosion means that a layer is eroded from the composition into the surrounding medium almost as if a slice of the matrix is cut off. Only the outer surface is exposed to erosion and from this outer layer the active substance will be released and/or dissolved provided that an active substance is present in the matrix. This means that if it is possible to control the size of the surface area by maintaining a constant size, it is possible to control the size of the release rate and, furthermore, a zero order release rate can be obtained.

The outer layers contain the same active substance as the inner layer A) to ensure optimal absorption of the active substance though the gastrointestinal tract a way to prolong the effect of e.g. a once-daily dosage form.

As mentioned above, each of the outer layers B1) and B2) comprises iii) a substantially water soluble and/or crystalline polymer or a mixture of substantially water soluble and/or crystalline polymers, the polymer being a polyglycol in the from of one of a) a homopolymer having a MW of at least about 100,000 daltons, and b) a copolymer having a MW of at least about 2,000 daltons, The layers B1) and B2) may have the same or different composition and in a cylindrical shaped composition they may have the same or different size. In a preferred embodiment, the composition and size of the two B) layers are the same.

Suitable polymers for use in the outer layers are described in detail in the section above. However, with respect to the outer layer, it is important to ensure a control of the rate with which the outer layer disappears from the composition once it is exposed to an aqueous medium. As described above, the outer layers are composed in such a manner that the outer layer leaves the composition with a constant rate (corresponding to a zero order release rate in the event that a drug substance was present in the layer). Such a constant rate can be achieved by use of one or more polyglycols, but in contrast to the polymers suitable for used in the inner layer A), the homopolymer should preferably have a much higher molecular weight in order to ensure a constant erosion rate of the outer layer. Moreover, it is contemplated that when a co-polymer is employed preferably one or more of another polymer is included in the outer layer in order to obtain a suitable constant erosion rate.

As the function of the outer layers is different from the function of the inner layer, the polymer composition of the outer layer(s) B is different from the polymer composition of the inner layer A).

One or more pharmaceutically acceptable excipients or additives may also be incorporated into the outer layer(s), see the section herein. However, it is important that such excipients or additives do not significantly change the manner in which the outer layer disappears from the composition, i.e. it is important that this disappearance still is by a substantially constant rate e.g. by erosion or diffusion; addition of such substances may have impact on the rate (e.g. slow down or increase the rate), but it must not significantly change the properties of the outer layer B) so that the function as a "controlled lag-time layer provider" is destroyed.

In some embodiments of the invention, the outer layer B) may also contain one or more second active substances. Normally, such a second active substance in layer B) will be a different substance from that contained in layer A) in order to achieve a suitable combination treatment with two of more different active substance, one of which with a desired controlled release following a zero order release (the one contained in the outer layer B)) and the other one contained in the inner layer and designed for immediate release (or, alternatively, as detailed described under the section "Inner layer", as a controlled release composition e.g. with zero or 1st order release).

In the section "Other embodiments of the invention" examples of various combinations are described.

Coating

As described above, the layered composition is provided with a coating C) that has at least one opening exposing at least one surface of said outer layer (layer B), the coating being substantially insoluble in and impermeable to fluids and comprising a polymer.

A composition according to the invention may be provided with a coating that can be applied in such a manner that it leaves a well-defined surface area free of coating while the remaining surface is covered and at the same time ensuring that the coating fulfils the requirement that no transport of water into the matrix (or other parts of the composition) takes place through the coating (or, if any water should enter, then it does not result in a transport of dissolved active substance out through the coating). In other words, it has been the object to develop a coating that does not leave an uncontrollable surface area of the matrix exposed to the aqueous environment and that has suitable properties compared to the matrix, i.e. if the coating dissolves or otherwise disappears then it should only take place after the matrix has eroded or dissolved away (during the release period, the coating may of course also partly dissolve or disappear provided that the part it concerns covered a part of the matrix that has already been subject to erosion or diffusion, thus, leaving the remaining composition "intact" with a matrix that is surrounded by the coating apart from the open end from which erosion or diffusion of the matrix takes place).

The composition may be partly or fully covered by a coat with specific properties in such a way that the exposed area of the matrix may be controlled by the use of a coat. In a specific example the coat is substantially insoluble, non-erodible and non-permeable to water leaving only the exposed areas of the composition for release. Such a coat may be composed of a polymer that has thermoplastic properties. Examples of such materials are mentioned below including cellulose derivative which has thermoplastic properties, plasticizer or plasticizers and/other functional excipients.

The coating may also be a coating, which is substantially soluble in and permeable to fluids such as body fluids during the intended release period provided that the coating dissolves so much slower than the matrix composition that the coating remains intact until the matrix has eroded and/or released the inner layer containing an active substance. Examples of suitable polymers include polyglycols as described herein.

The coating may further comprise any of the mentioned matrix materials (i.e. polymeric material suitable for use in the outer layers B) in a form, which erodes at a substantially slower rate than the rest of the matrix. The coating may thus comprise a matrix of one or more substantially water soluble crystalline polymers and, optionally, a non-ionic emulsifier, the coating being one which is eroded in the aqueous phase at a substantially slower rate than the outer layer B, whereby a substantially controlled area of the outer layer B matrix composition (in some cases also comprising a second active substance) is exposed during erosion of the matrix composition and/or during release of the active substance, and whereby the coating is substantially eroded upon erosion of the matrix composition and/or during release of the active substance. Such a coating will be designed so that its longitudinal erosion rate is substantially the same as the longitudinal erosion rate of the matrix, whereby the matrix and the coating will erode longitudinally towards the centre of the composition at substantially the same rate. Thus, when the outer layer matrix composition has been completely eroded and/or dissolved by the aqueous medium and the inner layer has been released from the shell (i.e. the coating), the coating will also be substantially completely eroded. A matrix composition having such a coating has the obvious advantage of being completely biodegraded upon release of the active substance.

The coating may impart delayed properties for releasing the active substance or it may be a film-coating or a coating containing the active substance for immediate release prior to the controlled release or other kinds of coatings that does not delay the release but e.g. make it easier to swallow the composition or it may e.g. mask a bad taste. Materials suitable for such coatings are well-known for a person skilled in the art and information can be found e.g. in the latest editions of handbooks like Handbook of Pharmaceutical Excipients or in Remington's Pharmaceutical Sciences.

In an embodiment of the invention, the coating is one, which biodegrades, disintegrates crumbles or dissolves after erosion of the matrix and/or during the release of the active substance. A coating applied for an erosion matrix will remain intact as long as it is supported by the matrix containing the active substance, but it lacks the ability to remain intact after erosion of the matrix, because it then biodegrades, disintegrates or crumbles, so that it will not remain in e.g. a human for any significant amount of time after the complete erosion of the outer matrix layer B and the release of the inner layer A.

In an interesting embodiment, the composition of the invention further comprises a coating having at least one opening exposing at least one surface of the matrix, the coating being one which crumbles and/or erodes upon exposure to the aqueous medium at a rate which is equal to or slower than the rate at which the matrix erodes in the aqueous medium, allowing exposure of said surface of the matrix to the aqueous medium to be controlled.

Polymers useful as coatings are such as e.g. cellulose derivative e.g. ethylcellulose, cellulose acetate, cellulose propionate, cellulose nitrate, cellulose derivative selected from the group consisting of methylcellulose, carboxymethylcellulose and salts thereof, cellulose acetate phthalate, microcrystalline cellulose, ethylhydroxyethylcellulose, ethylmethylcellulose, hydroxyethylcellulose, hydroxyethylmethylcellulose, hydroxypropylcellulose, hydroxypropylmethylcellulose, hydroxymethylcellulose and hydroxymethylpropylcellulose, cellulose acetate, Eudragit L methyl ester, Eudragit RL, Eudragit E, polyamide, polyethylene, polyethylene terephthalate, polypropylene polyurethane, polyvinyl acetate, polyvinyl chloride, silicone rubber, latex, polyhydroxybutyrate, polyhydroxyvalerate, polytetrafluoroethylene, polylactic acid or polyglycolic acid and copolymers thereof, copolymers such as ethylene vinyl acetate (EVA), styrene-butadienestyrene (SBS) and styrene-isoprene-styrene (SIS). The coating may also be copolymers of polylactic acid and polyglycolic acid. The coating may also be an enteric coating employing methacrylates Eudragit L, Eudragit S, Eudragit FS, a co-polymer of methacrylate-galactomannan etc.

In one embodiment, the controlled release composition of the invention further comprises a coating having at least one opening exposing at least one surface of the matrix, the coating being one which crumbles and/or erodes upon exposure to the aqueous medium at a rate which is equal to or slower than the rate at which the matrix erodes in the aqueous medium, allowing exposure of said surface of the matrix to the aqueous medium to be controlled. Coatings of this type are described in WO 95/22962, to which reference is made and which is incorporated herein by reference. These coatings comprise:

(a) a first cellulose derivative which has thermoplastic properties and which is substantially insoluble in the aqueous medium in which the composition is to be used, e.g. an ethylcellulose such as ethylcellulose having an ethoxyl content in the range of 44.5-52.5%, or cellulose acetate, cellulose propionate or cellulose nitrate;

and at least one of:

(b) a second cellulose derivative which is soluble or dispersible in water, e.g. a cellulose derivative selected from the group consisting of methylcellulose, carboxymethylcellulose and salts thereof, cellulose acetate phthalate, microcrystalline cellulose, ethylhydroxyethylcellulose, ethylmethylcellulose, hydroxyethylcellulose, hydroxyethylmethylcellulose, hydroxypropylcellulose, hydroxypropylmethylcellulose, hydroxymethylcellulose and hydroxymethylpropylcellulose;

(c) a plasticizer, e.g. selected from the group consisting of phosphate esters; phthalate esters; amides; mineral oils; fatty acids and esters thereof; polyethylene glycol, glycerin or sugars; fatty alcohols and ethers thereof; vegetable oils; or a non-ionic surfactant; and (d) a filler, e.g. selected from conventional tablet or capsule excipients such as diluents, binders, lubricants and disintegrants.

The first cellulose derivative (a) such as, e.g., ethylcellulose is typically contained in the coating in a concentration of from about 10 to about 99% w/w such as, e.g., from about 20 to about 95% w/w, from about 30 to about 90% w/w, from about 40 to about 90% w/w, from about 45 to about 90% w/w, from about 50 to about 85% w/w or from about 50 to about 80% w/w.

In general, the concentration of the polymer in the coating is from about 60% w/w to about 100% w/w. 0-40% w/w of one or more of a plasticizer, a colouring agent, a stabilizer, a glidants or the like may also be present in the coating.

Moreover, in some embodiments of the invention a further active substance may be incorporated in the coating or the composition may be provided with a second coating comprising the further active substance. Such a coating may be designed to release the active substance from the coating immediately after oral administration or a composition of the invention may be subject to enteric coating such that release will be pH dependent.

Such compositions wherein a coating contains an active substance may be of interest in those situations where a fast onset of action is desired, i.e. a fast release of an active substance is desired in order to quickly obtain a therapeutically effective plasma concentration of the active substance. Such an active substance may be the same or different from that contained in layer B and/or the inner layer A dependent on the particular disease or condition to be treated.

In such cases where a second coating is provided on the composition such a coating is generally a film-coating and it is normally applied in a separate manufacturing step (e.g. not by injection moulding, but using processes generally applicable for film-coating of tablets such as, e.g., pan coating, fluid bed coating, spray coating, dip coating etc.).

Dose Dumping

In one aspect, the invention is based on controlled release compositions comprising polymer or a mixture of polymers, more specifically a polyglycol, an active substance and optionally one or more pharmaceutically acceptable excipients in layer B. Polymers and pharmaceutically acceptable excipients suitable for use in such a composition as well as relevant active substances are described herein. Such compositions have proved to mitigate the risk of alcohol induced dose dumping. "Dose dumping" is unintended, rapid drug release in a short period of time of the entire amount or a significant fraction of the active substance retained in a controlled release dosage.

In a specific embodiment of the invention the release mechanism is primarily erosion or diffusion from layer B composed of a polymer matrix, an active substance and if necessary one or more excipients. The mechanism of erosion enables the composition to release with a rate depending on the exposed area. Inner layer A of the invention contains active substance or active multiple units (e.g. pellets or mini tablets) in such a form that the active substance or individual active units will be made available upon disintegration of the composition in the stomach, small intestine and/or colon after erosion of layer B. The individual units are of a size, which allows them to be incorporated into such a composition.

The matrix composition of layer B and active multiple units according to the invention has (in total) a lower (or equal) solubility and/or release rate in alcohol containing media (e.g. ethanol) than in aqueous media (e.g. water, buffer).

The active substance in the above mention matrix composition optionally comprising chosen polymers and excipients in a suitable ratio attains an unchanged or lower dissolution rate when tested in alcohol containing media as compared to aqueous media.

In principle, the use of a composition to avoid alcohol dose dumping can be of relevance for any active substance. An easy manner to investigate whether a composition potentially will be subject to alcohol induced dose dumping is to subject the composition to an dissolution test using a dissolution medium with and without alcohol and investigate whether there are any differences in the release pattern under the two different conditions. The harshest conditions are in a dissolution medium containing 40% (v/v) ethanol. If the dissolution rate of the composition is substantially unaffected or slower, then it is likely to assume that no alcohol induced dose dumping will take place in vivo.

Active Substances for Use in a Composition of the Invention

A composition according to the invention comprises one or more active substances. At least one active substance is included in the inner layer and outer layer(s) of the composition, which are the same, but the outer layer(s) may also contain one or more active substances that is different from the active substance contained in the inner layer.

Typically, the amount of each active substance in the composition if the same active substance is present in the inner layer and/or outer layer and/or in the coating) corresponds to a daily or part of a daily therapeutic dose.

A pharmaceutical composition according to the invention is suitable for use for both water soluble as well as slightly soluble or insoluble active substances.

Thus, a pharmaceutical composition according to the invention may comprise one or more active substances, i.e. substances, which are therapeutically, prophylactically, diagnostically and/or biologically active substance. The term "active substance" as used herein broadly includes any compound, or mixture thereof, that can be delivered from the composition to produce a beneficial result.

The active substance or substances included in a pharmaceutical composition of the invention may be selected from many therapeutic categories, in particular from substances which may advantageously be administered orally, rectally, vaginally, or administered to a body cavity (e.g. the urinary bladder, kidney pelvis, the gall bladder, the uterus, a central nervous system cavity, infectious/malignant/post-operative cavities, etc.).

Examples of specific active substances suitable for use in a composition of the invention are: Stomatological active substances; Epinephrine, Benzydamine, Acetylsalicylic acid, Adrenalone, Amlexanox, Sodium fluoride, Sodium monofluorophosphate, Olaflur, Stannous fluoride, Sodium fluoride, Hydrogen peroxide, Chlorhexidine, Amphotericin B, Polynoxylin, Domiphen, Oxyquinoline, Neomycin, Miconazole, Natamycin, Hexetidine, Tetracycline, Benzoxonium chloride, Tibezonium iodide, Mepartricin, Metronidazole, Clotrimazole, Sodium perborate, Chlortetracycline, Doxycycline, Minocycline, Triamcinolone, Dexamethasone, Hydrocortisone, Prednisolone. Active substances for acid related disorders; Magnesium carbonate, Magnesium oxide, Magnesium peroxide, Magnesium hydroxide, Magnesium silicate, Aluminium hydroxide, Algeldrate, Aluminium phosphate, Dihydroxialumini sodium carbonate, Aluminium acetoacetate, Aloglutamol, Aluminium glycinate, Calcium carbonate, Calcium silicate, Ordinary salt combinations, Magaldrate, Almagate, Hydrotalcite, Almasilate, Magaldrate, Cimetidine, Ranitidine, Famotidine, Nizatidine, Niperotidine, Roxatidine, Ranitidine bismuth citrate, Lafutidine, Cimetidine, Famotidine, Misoprostol, Enprostil, Omeprazole, Pantoprazole, Lansoprazole, Rabeprazole, Esomeprazole, Carbenoxolone, Sucralfate, Pirenzepine, Methiosulfonium chloride, Bismuth subcitrate, Proglumide, Gefarnate, Sulglicotide, Acetoxolone, Zolimidine, Troxipide, Bismuth subnitrate, Alginic acid. Active substances for functional gastrointestinal disorders; Oxyphencyclimine, Camylofin, Mebeverine, Trimebutine, Rociverine, Dicycloverine, Dihexyverine, Difemerine, Piperidolate, Metoclopramide, Cisapride, Domperidone, Bromopride, Alizapride, Clebopride. Antiemetic and antinauseant active substances; Serotonin (5HT3) antagonists, Ondansetron, Granisetron, Tropisetron, Dolasetron, Palonosetron, Scopolamine, Cerium oxalate, Chlorobutanol, Metopimazine, Dronabinol, Nabilone, Aprepitant. Active substances for bile and liver therapy; Bile acid preparations, Chenodeoxycholic acid, Ursodeoxycholic acid, Nicotinyl methylamide, Piprozolin, Hymecromone, Cyclobutyrol, Arginine glutamate, Silymarin, Citiolone, Epomediol, Ornithine oxoglurate, Tidiacic arginine. Laxative active substances; Softeners, Emollients, Liquid paraffin, Docusate sodium, Liquid paraffin, Contact laxatives, Oxyphenisatine, Bisacodyl, Dantron, Phenolphthalein, Castor oil, *Senna* glycosides, Cascara, Sodium picosulfate, Bisoxatin, *Belladonna* alkaloids, Bisacodyl, Dantron, *Senna* glycosides, Cascara, Sodium picosulfate, Ispaghula (*psylla* seeds), Ethulose, Sterculia, Linseed, Methylcellulose, *Triticum* (wheat fibre), Polycarbophil calcium, Magnesium carbonate, Magnesium oxide, Magnesium peroxide, Magnesium sulfate, Lactulose, Lactitol, Sodium sulfate, Pentaerithrityl, Macrogol, Mannitol, Sodium phosphate, Sorbitol, Magnesium citrate, Sodium tartrate, Enemas, Sodium phosphate, Bisacodyl, Glycerol, Oil, Laurilsulfate, Carbon dioxide producing drugs. Antidiarrheal, intestinal, anti-inflammatory/antiinfective active substances; Antibiotics, Neomycin, Nystatin, Natamycin, Streptomycin, Polymyxin B, Paromomycin, Amphotericin B, Kanamycin, Vancomycin, Colistin, Rifaximin, Sulfonamides, Phthalylsulfathiazole, Sulfaguanidine, Succinylsulfathiazole, Imidazole derivatives, Miconazole, Broxyquinoline, Acetarsol, Nifuroxazide, Nifurzide, Medicinal charcoal, Bismuth, Pectin, Kaolin, Crospovidone, Attapulgite, Diosmectite, Diphenoxylate, Opium, Loperamide, Difenoxin, Loperamide oxide, Morphine, Prednisolone, Hydrocortisone, Prednisone, Betamethasone, Tixocortol, Budesonide, Beclometasone, Antiallergic agents, excl. corticosteroids, Cromoglicic acid, Aminosalicylic acid and similar agents, Sulfasalazine, Mesalazine, Olsalazine, Balsalazide, Antidiarrheal microorganisms, Lactic acid producing organisms, *Saccharomyces boulardii*, Lactic acid producing organisms, Albumin tannate, *Ceratonia*, Calcium compounds, Racecadotril. Antiobesity active substances; Phentermine, Fenfluramine, Amfepramone, Dexfenfluramine, Mazindol, Etilamfetamine, Cathine, Clobenzorex, Mefenorex, Sibutramine, Ephedrine, Orlistat, Rimonabant. Digestiveactive substances; Enzyme preparations, Diastase, Multienzymes (lipase, protease etc.), Pepsin, Tilactase, Acid preparations, Glutamic acid hydrochloride, Betaine hydrochloride, Hydrochloric acid, Citric acid. Diabetes active substances; Insulins and analogues, Biguanides, Phenformin, Metformin, Buformin, Sulfonamides, urea derivatives, Glibenclamide, Chlorpropamide, Tolbutamide, Glibornuride, Tolazamide, Carbutamide, Glipizide, Gliquidone, Gliclazide, Metahexamide, Glisoxepide, Glimepiride, Acetohexamide, Sulfonamides (heterocyclic), Glymidine, Combinations of oral blood glucose lowering drugs, Alpha glucosidase inhibitors, Acarbose, Miglitol, Voglibose, Thiazolidinediones, Troglitazone, Rosiglitazone, Pioglitazone, Dipeptidyl peptidase 4 (DPP-4) inhibitors, Sitagliptin, Vildagliptin, Guar gum, Repaglinide, Nateglinide, Exenatide, Aldose reductase inhibitors, Tolrestat. Anabolic active substances; Androstan derivatives, Androstanolone, Stanozolol, Metandienone, Metenolone, Oxymetholone, Quinbolone, Prasterone, Oxandrolone, Norethandrolone, Estren derivatives, Nandrolone, Ethylestrenol, Oxabolone cipionate. Metabolism active substances; Amino acids and derivatives, Levocarnitine, Ademetionine, Glutamine, Mercaptamine, Carglumic acid, Betaine, Enzymes, Alglucerase, Imiglucerase, Agalsidase alfa, Agalsidase beta, Laronidase, Sacrosidase, Alglucosidase alfa, Galsulfase, Idursulfase, Tioctic acid, Anethole trithione, Sodium phenylbutyrate, Nitisinone, Zinc acetate, Miglustat, Sapropterin.

Antithrombotic active substances; Vitamin K antagonists, Dicoumarol, Phenindione, Warfarin, Phenprocoumon, Acenocoumarol, Ethyl biscoumacetate, Clorindione, Diphenadione, Tioclomarol, Heparin, Antithrombin III, Dalteparin, Enoxaparin, Nadroparin, Parnaparin, Reviparin, Danaparoid, Tinzaparin, Sulodexide, Bemiparin, Platelet aggregation inhibitors excl. heparin, Ditazole, Cloricromen, Picotamide, Clopidogrel, Ticlopidine, Acetylsalicylic acid, Dipyridamole, Carbasalate calcium, Epoprostenol, Indobufen, Iloprost, Abciximab, Aloxiprin, Eptifibatide, Tirofiban, Triflusal, Beraprost, Treprostinil, Enzymes, Streptokinase, Alteplase, Anistreplase, Urokinase, Fibrinolysin, Brinase, Reteplase, Saruplase, Ancrod, Drotrecogin alfa (activated), Tenecteplase, Protein C, Direct thrombin inhibitors, Desirudin, Lepirudin, Argatroban, Melagatran, Ximelagatran, Bivalirudin, Dabigatran etexilate, Defibrotide, Dermatan sulfate, Fondaparinux. Antihemorrhagics active substances; Amino acids, Aminocaproic acid, Tranexamic acid, Aminomethylbenzoic acid, Proteinase inhibitors, Aprotinin, Alfa1 antitrypsin, C1-inhibitor, Camostat, Vitamin K, Phytomenadione, Menadione, Fibrinogen, Local hemostatics, Absorbable gelatin sponge, Oxidized cellulose, Tetragalacturonic acid hydroxymethylester, Adrenalone, Thrombin, Collagen, Calcium alginate, Epinephrine, Blood coagulation factors, Coagulation factor IX, II, VII and X in combination, Coagulation factor VIII, Factor VIII inhibitor bypassing activity, Coagulation factor IX, Coagulation factor VII, Von Willebrand factor and coagulation factor VIII in combination, Coagulation factor XIII, Eptacog alfa (activated), Nonacog alfa, Thrombin, Etamsylate, Carbazochrome, Batroxobin. Antianemic active substances; Ferrous glycine sulfate, Ferrous fumarate, Ferrous gluconate, Ferrous carbonate, Ferrous chloride, Ferrous succinate, Ferrous sulfate, Ferrous tartrate, Ferrous aspartate, Ferrous ascorbate, Ferrous iodine, Ferric sodium citrate, Saccharated iron oxide, Sodium feredetate, Ferric hydroxide, Dextriferron, Ferric citrate, Chondroitin sulfate-iron complex, Ferric acetyl transferrin, Ferric proteinsuccinylate, Dextriferron, Vitamin B12 (cyanocobalamin and analogues), Cyanocobalamin, Cyanocobalamin tannin complex, Hydroxocobalamin, Cobamamide, Mecobalamin, Folic acid and derivatives, Erythropoietin, Darbepoetin alfa, Methoxy polyethylene glycol-epoetin beta. Hematological active subtances; Fibrinolysin and desoxyribonuclease, Hyaluronidase, Chymotrypsin, Trypsin, Desoxyribonuclease, Bromelains, Streptokinase, combinations, Hematin.

Cardiac stimulant active substances; Cardiac glycosides, *Digitalis* glycosides, Acetyldigitoxin, Acetyldigoxin, *Digitalis* leaves, Digitoxin, Digoxin, Lanatoside C, Deslanoside, Metildigoxin, Gitoformate, Scilla glycosides, Proscillaridin, Strophantus glycosides, G-strophanthin, Cymarin, Peruvoside, Adrenergic and dopaminergic agents, Etilefrine, Isoprenaline, Norepinephrine, Dopamine, Norfenefrine, Phenylephrine, Dobutamine, Oxedrine, Metaraminol, Methoxamine, Mephentermine, Dimetofrine, Prenalterol, Dopexamine, Gepefrine, Ibopamine, Midodrine, Octopamine, Fenoldopam, Cafedrine, Arbutamine, Theodrenaline, Epinephrine, Phosphodiesterase inhibitors, Amrinone, Milrinone, Enoximone, Bucladesine, Other cardiac stimulants, Angiotensinamide, Xamoterol, Levosimendan. Antiarrhythmics active subtances; class Ia, Quinidine, Procainamide, Disopyramide, Sparteine, Ajmaline, Prajmaline, Lorajmine, Antiarrhythmics, class Ib, Lidocaine, Mexiletine, Tocainide, Aprindine, Antiarrhythmics, class Ic, Propafenone, Flecainide, Lorcainide, Encainide, Antiarrhythmics, class III, Amiodarone, Bretylium tosilate, Bunaftine, Dofetilide, Ibutilide, Other class I antiarrhythmics, Moracizine, Cibenzoline. Active substances for vasodilation; Organic nitrates, Glyceryl trinitrate, Methylpropylpropanediol dinitrate, Pentaerithrityl tetranitrate, Propatylnitrate, Isosorbide dinitrate, Trolnitrate, Eritrityl tetranitrate, Isosorbide mononitrate, Tenitramine, Flosequinan, Itramin tosilate, Prenylamine, Oxyfedrine, Benziodarone, Carbocromen, Hexobendine, Etafenone, Heptaminol, Imolamine, Dilazep, Trapidil, Molsidomine, Efloxate, Cinepazet, Cloridarol, Nicorandil, Linsidomine, Nesiritide. Cardiac active substances; Prostaglandins, Alprostadil, Other cardiac preparations, *Camphora*, Indometacin, *Crataegus* glycosides, Creatinolfosfate, Fosfocreatine, Fructose 1,6-diphosphate, Ubidecarenone, Adenosine, Tiracizine, Tedisamil, Acadesine, Trimetazidine, Ibuprofen, Ivabradine, Ranolazine. Antihypertensive active substances; Rauwolfia alkaloids, Rescinnamine, Reserpine, Deserpidine, Methoserpidine, Bietaserpine, Methyldopa, Imidazoline receptor agonists, Clonidine, Guanfacine, Tolonidine, Moxonidine, Rilmenidine, Sulfonium derivatives, Trimetaphan, Secondary and tertiary amines, Mecamylamine, Bisquaternary ammonium compounds, Alpha-adrenoreceptor antagonists, Prazosin, Indoramin, Trimazosin, Doxazosin, Urapidil, Guanidine derivatives, Betanidine, Guanethidine, Guanoxan, Debrisoquine, Guanoclor, Guanazodine, Guanoxabenz, Thiazide derivatives, Diazoxide, Hydrazinophthalazine derivatives, Dihydralazine, Hydralazine, Endralazine, Cadralazine, Pyrimidine derivatives, Minoxidil, Nitroferricyanide derivatives, Nitroprusside, Guanidine derivatives, Pinacidil, Veratrum, Tyrosine hydroxylase inhibitors, Metirosine, MAO inhibitors, Pargyline, Serotonin antagonists, Ketanserin, http://www.whocc.no/atcddd/indexdatabase/index.php?query=C02KX Bosentan, Ambrisentan, Sitaxentan. Diuretic active substances; Thiazides, Bendroflumethiazide, Hydroflumethiazide, Hydrochlorothiazide, Chlorothiazide, Polythiazide, Trichlormethiazide, Cyclopenthiazide, Methyclothiazide, Cyclothiazide, Mebutizide, Sulfonamides, Quinethazone, Clopamide, Chlortalidone, Mefruside, Clofenamide, Metolazone, Meticrane, Xipamide, Indapamide, Clorexolone, Fenquizone, Mercurial diuretics, Mersalyl, Xanthine derivatives, Theobromine, Cicletanine, Furosemide, Bumetanide, Piretanide, Torasemide, Aryloxyacetic acid derivatives, Etacrynic acid, Tienilic acid, Pyrazolone derivatives, Muzolimine, Etozolin, Aldosterone antagonists, Spironolactone, Potassium canrenoate, Canrenone, Eplerenone, Amiloride, Triamterene. Active substances for peripheral vasodilation; 2-amino-1-phenylethanol derivatives, Isoxsuprine, Buphenine, Bamethan, Imidazoline derivatives, Phentolamine, Tolazoline, Nicotinic acid, Nicotinyl alcohol (pyridylcarbinol), Inositol nicotinate, Ciclonicate, Purine derivatives, Pentifylline, Xantinol nicotinate, Pentoxifylline, Etofylline nicotinate, Ergot alkaloids, Ergoloid mesylates, Nicergoline, Dihydroergocristine, Kallidinogenase, Cyclandelate, Phenoxybenzamine, Vincamine, Moxisylyte, Bencyclane, Vinburnine, Suloctidil, Buflomedil, Naftidrofuryl, Butalamine, Visnadine, Cetiedil, Cinepazide, Ifenprodil, Azapetine, Fasudil. Vasoprotective active substances; Heparinoid, Sodium apolate, Heparin, Pentosan polysulfate sodium, Monoethanolamine oleate, Polidocanol, Invert sugar, Sodium tetradecyl sulfate, Phenol, Glucose, Calcium dobesilate, Bioflavonoids, Rutoside, Monoxerutin, Diosmin, Troxerutin, Hidrosmin, Tribenoside. Beta blocking active substances; Beta blocking agents, non-selective, Alprenolol, Oxprenolol, Pindolol, Propranolol, Timolol, Sotalol, Nadolol, Mepindolol, Carteolol, Tertatolol, Bopindolol, Bupranolol, Penbutolol, Cloranolol, Beta blocking agents, selective, Practolol, Metoprolol, Atenolol, Acebutolol, Betaxolol, Bevantolol, Bisoprolol, Celiprolol, Esmolol, Epanolol, S-atenolol, Nebivolol, Talinolol, Alpha and beta blocking agents, Labetalol, Carvedilol. Calium channel blockers; Dihydropyridine derivatives, Amlodipine, Felodipine, Isradipine, Nicardipine, Nifedipine, Nimodipine, Nisoldipine, Nitrendipine, Lacidipine, Nilvadipine, Manidipine, Barnidipine, Lercanidipine, Cilnidipine, Benidipine, Mibefradil, Phenylalkylamine derivatives, Verapamil, Gallopamil, Benzothiazepine derivatives, Diltiazem, Phenylalkylamine derivatives, Fendiline, Bepridil, Lidoflazine, Perhexiline. Active substances acting on the renin-angiotensin system; ACE inhibitors, Captopril, Enalapril, Lisinopril, Perindopril, Ramipril, Quinapril, Benazepril, Cilazapril, Fosinopril, Trandolapril, Spirapril, Delapril, Moexipril, Temocapril, Zofenopril, Imidapril, Other, Renin-inhibitors, Remikiren, Aliskiren, Angiotensin II antagonists, Losartan, Eprosartan, Valsartan, Irbesartan, Candesartan, Telmisartan, Olmesartan. Lipid modifying active substances; HMG CoA reductase inhibitors, Simvastatin, Lovastatin, Pravastatin, Fluvastatin, Atorvastatin, Cerivastatin, Rosuvastatin, Pitavastatin, Fibrates, Clofibrate, Bezafibrate, Aluminium clofibrate, Gemfibrozil, Fenofibrate, Simfibrate, Ronifibrate, Ciprofibrate, Etofibrate, Clofibride, Bile acid sequestrants, Colestyramine, Colestipol, Colextran, Colesevelam, Nicotinic acid and derivatives, Niceritrol, Nicofuranose, Aluminium nicotinate, Nicotinyl alcohol (pyridylcarbinol), Acipimox, Other lipid modifying agents, Dextrothyroxine, Probucol, Tiadenol, Benfluorex, Meglutol, Omega-3-triglycerides, Magnesium pyridoxal 5-phosphate glutamate, Policosanol, Ezetimibe Dermatological active substances for system use; Antifungals, Griseofulvin, Terbinafine, Protectives against UV-radiation for systemic use, Betacarotene, Antipsoriatics, Psoralens, Trioxysalen, Methoxsalen, Bergapten, Retinoids, Etretinate, Acitretin, Anti-acne, Isotretinoin, Ichtasol. Antiinfective and antiseptic active substances; Antibiotics, Nystatin, Natamycin, Amphotericin B, Candicidin, Chloramphenicol, Azidamfenicol, Hachimycin, Oxytetracycline, Carfecillin, Mepartricin, Clindamycin, Pentamycin, Arsenic compounds, Acetarsol, Quinoline derivatives, Diiodohydroxyquinoline, Clioquinol, Chlorquinaldol, Dequalinium, Broxyquinoline, Oxyquinoline, Organic acids, Lactic acid, Acetic acid, Ascorbic acid, Sulfonamides, Sulfatolamide, Combinations of sulfonamides, Imidazole derivatives, Metronidazole, Clotrimazole, Miconazole, Econazole, Ornidazole, Isoconazole, Tioconazole, Ketoconazole, Fenticonazole, Azanidazole, Propenidazole, Butoconazole, Omoconazole, Oxiconazole, Flutrimazole, Triazole derivatives, Terconazole, Clodantoin, Inosine, Policresulen, Nifuratel, Furazolidone, Methylrosaniline, Povidone-iodine, Ciclopirox, Protiofate, *Lactobacillus fermentum*, Copper usnate, Octenidine Gynecological active substances; Ergot alkaloids, Methylergometrine, Ergot alkaloids, Ergometrine, Oxytocin, Prostaglandins, Dinoprost, Dinoprostone, Gemeprost, Carboprost, Sulprostone, Misoprostol, Ritodrine, Buphenine, Fenoterol, Prolactine inhibitors, Bromocriptine, Lisuride, Cabergoline, Quinagolide, Metergoline. Hormones; Norgestrel, Gestodene, Norgestimate, Drospirenone, Norelgestromin, Progestogens, Norethisterone, Lynestrenol, Levonorgestrel, Quingestanol, Megestrol, Medroxyprogesterone, Norgestrienone, Etonogestrel, Desogestrel, 3-oxoandrosten (4) derivatives, Fluoxymesterone, Methyltestosterone, Testosterone, 5-androstanon (3) derivatives, Mesterolone, Androstanolone, Ethinylestradiol, Estradiol, Estriol, Chlorotrianisene, Estrone, Promestriene, Conjugated estrogens, Dienestrol, Diethylstilbestrol, Methallenestril, Moxestrol, Dienestrol, Methallenestril, Estrone, Diethylstilbestrol, Pregnen (4) derivatives, Gestonorone, Medroxyprogesterone, Hydroxyprogesterone, Progesterone, Pregnadien derivatives, Dydrogesterone, Megestrol, Medrogestone, Nomegestrol, Demegestone, Chlormadinone, Promegestone, Estren derivatives, Allylestrenol, Norethisterone, Lynestrenol, Ethisterone, Tibolone, Etynodiol, Methylestrenolone, Methyltestosterone, Methylnortestosterone, Noretynodrel, Dienogest, Trimegeston, Gonadotropins, Urofollitropin, Follitropin alfa, Follitropin beta, Lutropin alfa, Choriogonadotropin alfa, Cyclofenil, Clomifene, Epimestrol, Cyproterone, Danazol, Gestrinone, Antiprogestogens, Mifepristone, Raloxifene, Corticotropin, Tetracosactide, Thyrotropin, Thyrotropin, Somatropin and somatropin agonists, Somatropin, Somatrem, Mecasermin, Sermorelin, Mecasermin rinfabate, Pegvisomant, Vasopressin and analogues, Vasopressin, Desmopressin, Lypressin, Terlipressin, Ornipressin, Argipressin, Oxytocin and analogues, Demoxytocin, Oxytocin, Carbetocin, Gonadotropin-releasing hormones, Gonadorelin, Nafarelin, Histrelin, Anti-growth hormone, Somatostatin, Octreotide, Lanreotide, Vapreotide, Anti-gonadotropin-releasing hormones, Ganirelix, Cetrorelix, Glycogenolytic hormones, Glucagon, Parathyroid hormones and analogues, Teriparatide, Parathyroid hormone, Calcitonin, http://www.whocc.no/atcddd/indexdatabase/index.php?query=H05BA01 Elcatonin, Cinacalcet.

Urological active substances; Acidifiers, Ammonium chloride, Calcium chloride, Urinary concrement solvents, Urinary antispasmodics, Emepronium, Flavoxate, Meladrazine, Oxybutynin, Terodiline, Propiverine, Tolterodine, Solifenacin, Trospium, Darifenacin, Fesoterodine, Drugs used in erectile dysfunction, Alprostadil, Papaverine, Sildenafil, Yohimbin, Phentolamine, Moxisylyte, Apomorphine, Tadalafil, Vardenafil, Combinations, Papaverine, combinations, Magnesium hydroxide, Acetohydroxamic acid, Phenazopyridine, Succinimide, Collagen, Phenyl salicylate, Dimethyl sulfoxide, Alpha-adrenoreceptor antagonists, Alfuzosin, Tamsulosin, Terazosin, Testosterone-5-alpha reductase inhibitors, Finasteride, Dutasteride, *Pygeum africanum, Serenoa repens*, Mepartricin. Corticosteroids; Mineralocorticoids, Aldosterone, Fludrocortisone, Desoxycortone, Glucocorticoids, Betamethasone, Dexamethasone, Fluocortolone, Methylprednisolone, Paramethasone, Prednisolone, Prednisone, Triamcinolone, Hydrocortisone, Cortisone, Prednylidene, Rimexolone, Deflazacort, Cloprednol, Meprednisone, Cortivazol, Anticorticosteroids, Trilostane. Thyroid and antithyroid active substances; Thyroid hormones, Levothyroxine sodium, Liothyronine sodium, Tiratricol, Thiouracils, Methylthiouracil, Propylthiouracil, Benzylthiouracil, Sulfur-containing imidazole derivatives, Carbimazole, Thiamazole, Perchlorates, Potassium perchlorate, Diiodotyrosine, Dibromotyrosine, Iodine.

Antiinfective active substances; Demeclocycline, Doxycycline, Chlortetracycline, Lymecycline, Metacycline, Oxytetracycline, Tetracycline, Minocycline, Rolitetracycline, Penimepicycline, Clomocycline, Tigecycline, Amphenicols, Chloramphenicol, Thiamphenicol, Ampicillin, Pivampicillin, Carbenicillin, Amoxicillin, Carindacillin, Bacampicillin, Epicillin, Pivmecillinam, Azlocillin, Mezlocillin, Mecillinam, Piperacillin, Ticarcillin, Metampicillin, Talampicillin, Sulbenicillin, Temocillin, Hetacillin, Benzylpenicillin, Phenoxymethylpenicillin, Propicillin, Azidocillin, Pheneticillin, Penamecillin, Clometocillin, Benzathine, benzylpenicillin, Procaine benzylpenicillin, Benzathine phenoxymethylpenicillin, Dicloxacillin, Cloxacillin, Meticillin, Oxacillin, Flucloxacillin, Sulbactam, Tazobactam, Sultamicillin, Cefalexin, Cefaloridine, Cefalotin, Cefazolin, Cefadroxil, Cefazedone, Cefatrizine, Cefapirin, Cefradine, Cefacetrile, Cefroxadine, Ceftezole, Cefoxitin, Cefuroxime, Cefamandole, Cefaclor, Cefotetan, Cefonicide, Cefotiam, Loracarbef, Cefmetazole, Cefprozil, Ceforanide, Cefotaxime, Ceftazidime, Cefsulodin, Ceftriaxone, Cefmenoxime, Latamoxef, Ceftizoxime, Cefixime, Cefodizime, Cefetamet, Cefpiramide, Cefoperazone, Cefpodoxime, Ceftibuten, Cefdinir, Cefditoren, Ceftriaxone, Cefepime, Cefpirome, Monobactams, Aztreonam, Carbapenems, Meropenem, Ertapenem, Imipenem, Trimethoprim, Brodimoprim, Sulfaisodimidine, Sulfamethizole, Sulfadimidine, Sulfapyridine, Sulfafurazole, Sulfanilamide, Sulfathiazole, Sulfathiourea, Sulfamethoxazole, Sulfadiazine, Sulfamoxole, Sulfadimethoxine, Sulfalene, Sulfametomidine, Sulfametoxydiazine, Sulfamethoxypyridazine, Sulfaperin, Sulfamerazine, Sulfaphenazole, Sulfamazone, Macrolides, Erythromycin, Spiramycin, Midecamycin, Oleandomycin, Roxithromycin, Josamycin, Troleandomycin, Clarithromycin, Azithromycin, Miocamycin, Rokitamycin, Dirithromycin, Flurithromycin, Telithromycin, Lincosamides, Clindamycin, Lincomycin, Streptogramins, Pristinamycin, Quinupristin/dalfopristin, Streptomycins, Streptomycin, Streptoduocin, Other aminoglycosides, Tobramycin, Gentamicin, Kanamycin, Azithromycin, Neomycin, Amikacin, Retapamulin, Netilmicin, Sisomicin, Dibekacin, Ribostamycin, Isepamicin, Fluoroquinolones, Ofloxacin, Ciprofloxacin, Pefloxacin, Enoxacin, Temafloxacin, Norfloxacin, Lomefloxacin, Fleroxacin, Sparfloxacin, Rufloxacin, Grepafloxacin, Levofloxacin, Trovafloxacin, Moxifloxacin, Gemifloxacin, Gatifloxacin, Prulifloxacin, Pazufloxacin, Garenoxacin, Other quinolones, Rosoxacin, Nalidixic acid, Piromidic acid, Pipemidic acid, Oxolinic acid, Cinoxacin, Flumequine, Glycopeptide antibacterials, Vancomycin, Teicoplanin, Telavancin, Polymyxins, Colistin, Polymyxin B, Steroid antibacterials, Fusidic acid, Imidazole derivatives, Metronidazole, Tinidazole, Ornidazole, Nitrofuran derivatives, Nitrofurantoin, Nifurtoinol, Fosfomycin, Xibornol, Clofoctol, Spectinomycin, Methenamine, Mandelic acid, Nitroxoline, Linezolid, Daptomycin. Antimycotic active substances; Antibiotics, Amphotericin B, Hachimycin, Imidazole derivatives, Miconazole, Ketoconazole, Triazole derivatives, Fluconazole, Itraconazole, Voriconazole, Posaconazole, Flucytosine, Caspofungin, Micafungin, Anidulafungin. Antimycobacterial active substances; Aminosalicylic acid and derivatives, Sodium aminosalicylate, Calcium aminosalicylate, Antibiotics, Cycloserine, Rifampicin, Rifamycin, Rifabutin, Rifapentine, Capreomycin, Hydrazides, Isoniazid, Isoniazid, Thiocarbamide derivatives, Protionamide, Tiocarlide, Ethionamide, Pyrazinamide, Ethambutol, Terizidone, Morinamide, Clofazimine, Dapsone, Aldesulfone sodium. Antiviral active substances; Thiosemicarbazones, Metisazone, Nucleosides and nucleotides, Aciclovir, Idoxuridine, Vidarabine, Ribavirin, Ganciclovir, Famciclovir, Valaciclovir, Cidofovir, Penciclovir, Valganciclovir, Brivudine, Cyclic amines, Rimantadine, Tromantadine, Phosphonic acid derivatives, Foscarnet, Fosfonet, Protease inhibitors, Saquinavir, Indinavir, Ritonavir, Nelfinavir, Amprenavir, Lopinavir, Fosamprenavir, Atazanavir, Tipranavir, Darunavir, Zidovudine, Didanosine, Zalcitabine, Stavudine, Lamivudine, Abacavir, Tenofovir disoproxil, Adefovir dipivoxil, Emtricitabine, Entecavir, Telbivudine, Nevirapine, Delavirdine, Efavirenz, Zanamivir, Oseltamivir, Moroxydine, Lysozyme, Inosine pranobex, Pleconaril, Enfuvirtide, Raltegravir, Maraviroc. Immune sera and immunoglobulin; Diphtheria antitoxin, Tetanus antitoxin, Snake venom antiserum, Botulinum antitoxin, Gas-gangrene sera, Rabies serum, Immunoglobulins from human, Anti-D (rh) immunoglobulin, Tetanus immunoglobulin, Varicella/zoster immunoglobulin, Hepatitis B immunoglobulin, Rabies immunoglobulin, *Rubella* immunoglobulin, Vaccinia immunoglobulin, *Staphylococcus* immunoglobulin, Cytomegalovirus immunoglobulin, Diphtheria immunoglobulin, Hepatitis A immunoglobulin, Encephalitis, tick borne immunoglobulin, Pertussis immunoglobulin, Measles immunoglobulin, Mumps immunoglobulin, Palivizumab, Nebacumab. Vaccines; Bacterial vaccines, Anthrax vaccines, Anthrax antigen, Brucellosis vaccines, *Brucella* antigen, Cholera vaccines, Diphtheria vaccines, Diphtheria toxoid, Hemophilus *influenzae* B vaccines, Meningococcal vaccines, Meningococcus A, Meningococcus B, Meningococcus C, Pertussis vaccines, Plague vaccines, Pneumococcal vaccines, Pneumococcus, Tetanus vaccines, Tuberculosis vaccines, Typhoid vaccines, Typhus (exanthematicus) vaccines, Other bacterial vaccines, viral vaccines, Encephalitis vaccines, Influenza vaccines, Hepatitis vaccines, Measles vaccines, Mumps vaccines, Poliomyelitis vaccines, Rabies vaccines, Rota virus vaccines, *Rubella* vaccines, Varicella zoster vaccines, Yellow fever vaccines, Papillomavirus vaccines, Other viral vaccines.

Antineoplastic and immunomodulating active substances; Nitrogen mustard analogues, Cyclophosphamide, Chlorambucil, Melphalan, Chlormethine, Ifosfamide, Trofosfamide, Prednimustine, Alkyl sulfonates, Busulfan, Treosulfan, Mannosulfan, Ethylene imines, Thiotepa, Triaziquone, Carboquone, Nitrosoureas, Carmustine, Lomustine, Semustine, Streptozocin, Fotemustine, Nimustine, Ranimustine, Epoxides, Etoglucid, Other alkylating agents, Mitobronitol, Pipobroman, Temozolomide, Dacarbazine. Antimetabolite active substances; Folic acid analogues, Methotrexate, Raltitrexed, Pemetrexed, Purine analogues, Mercaptopurine, Tioguanine, Cladribine, Fludarabine, Clofarabine, Nelarabine, Pyrimidine analogues, Cytarabine, Fluorouracil, Tegafur, Carmofur, Gemcitabine, Capecitabine, *Vinca* alkaloids and analogues, Vinblastine, Vincristine, Vindesine, Vinorelbine, Podophyllotoxin derivatives, Etoposide, Teniposide, Colchicine derivatives, Demecolcine, Taxanes, Paclitaxel, Docetaxel, Other plant alkaloids and natural products, Trabectedin. Cytotoxic antibiotic and related active substances; Actinomycines, Dactinomycin, Anthracyclines and related substances, Doxorubicin, Daunorubicin, Epirubicin, Aclarubicin, Zorubicin, Idarubicin, Mitoxantrone, Pirarubicin, Valrubicin, Other cytotoxic antibiotics, Bleomycin, Plicamycin, Mitomycin, Ixabepilone. Antineoplastic active substances; Platinum compounds, Cisplatin, Carboplatin, Oxaliplatin, Methylhydrazines, Procarbazine, Monoclonal antibodies, Edrecolomab, Rituximab, Trastuzumab, Alemtuzumab, Gemtuzumab, Cetuximab, Bevacizumab, Panitumumab, Sensitizers used in photodynamic/radiation therapy, Porfimer sodium, Methyl aminolevulinate, Aminolevulinic acid, Temoporfin, Efaproxiral, Protein kinase inhibitors, Imatinib, Gefitinib, Erlotinib, Sunitinib, Sorafenib, Dasatinib, Lapatinib, Nilotinib, Other antineoplastic agents, Amsacrine, Asparaginase, Altretamine, Hydroxycarbamide, Lonidamine, Pentostatin, Miltefosine, Masoprocol, Estramustine, Tretinoin, Mitoguazone, Topotecan, Tiazofurine, Irinotecan, Alitretinoin, Mitotane, Pegaspargase, Bexarotene, Arsenic trioxide, Denileukin diftitox, Bortezomib, Celecoxib, Anagrelide, Oblimersen, Sitimagene ceradenovec, Combinations of antineoplastic agents. Endocrine active substances; Estrogens, Diethylstilbestrol, Polyestradiol phosphate, Ethinylestradiol, Fosfestrol, Progestogens, Megestrol, Medroxyprogesterone, Medroxyprogesterone, Gestonorone, Gonadotropin releasing hormone analogues, Buserelin, Leuprorelin, Goserelin, Triptorelin, hormones antagonists, Anti-estrogens, Tamoxifen, Toremifene, Fulvestrant, Anti-androgens, Flutamide, Nilutamide, Bicalutamide, Enzyme inhibitors, Aminogluthetimide, Formestane, Anastrozole, Letrozole, Vorozole, Exemestane, Abarelix. Immunostimulant active substances; Cytokines and immunomodulators, Colony stimulating factors, Filgrastim, Molgramostim, Sargramostim, Lenograstim, Ancestim, Pegfilgrastim, Interferons, Peginterferons, Interleukins, Aldesleukin, Oprelvekin, Lentinan, Roquinimex, BCG vaccine, Pegademase, Pidotimod, Poly I:C, Poly ICLC, Thymopentin, Immunocyanin, Tasonermin, Melanoma vaccine, Glatiramer acetate, Histamine dihydrochloride, Mifamurtide. Immunosuppressive active substances; Ciclosporin, Muromonab-CD3, Antilymphocyte immunoglobulin, Antithymocyte immunoglobulin, Tacrolimus, Mycophenolic acid, Daclizumab, Basiliximab, Sirolimus, Etanercept, Infliximab, Leflunomide, Anakinra, Alefacept, Afelimomab, Adalimumab, Everolimus, Gusperimus, Efalizumab, Abetimus, Natalizumab, Abatacept, Eculizumab, Certolizumab pegol, Other immunosuppressive agents, Azathioprine, Thalidomide, Methotrexate, Lenalidomide.

Antiinflammatory and antirheumatic active substances; Butylpyrazolidines, Phenylbutazone, Mofebutazone, Oxyphenbutazone, Clofezone, Kebuzone, Acetic acid derivatives and related substances, Indometacin, Sulindac, Tolmetin, Zomepirac, Diclofenac, Alclofenac, Bumadizone, Etodolac, Lonazolac, Fentiazac, Acemetacin, Difenpiramide, Oxametacin, Proglumetacin, Ketorolac, Aceclofenac, Bufexamac, Oxicams, Piroxicam, Tenoxicam, Droxicam, Lornoxicam, Meloxicam, Propionic acid derivatives, Ibuprofen, Naproxen, Ketoprofen, Fenoprofen, Fenbufen, Benoxaprofen, Suprofen, Pirprofen, Flurbiprofen, Indoprofen, Tiaprofenic acid, Oxaprozin, Ibuproxam, Dexibuprofen, Flunoxaprofen, Alminoprofen, Dexketoprofen, Fenamates, Mefenamic acid, Tolfenamic acid, Flufenamic acid, Meclofenamic acid, Coxibs, Celecoxib, Rofecoxib, Valdecoxib, Parecoxib, Etoricoxib, Lumiracoxib, Nabumetone, Niflumic acid, Azapropazone, Glucosamine, Benzydamine, Glucosaminoglycan polysulfate, Proquazone, Orgotein, Nimesulide, Feprazone, Diacerein, Morniflumate, Tenidap, Oxaceprol, Chondroitin sulfate, Feprazone, Dipyrocetyl, Acetylsalicylic acid, Quinolines, Oxycinchophen, Gold preparations, Sodium aurothiomalate, Sodium aurotiosulfate, Auranofin, Aurothioglucose, Aurotioprol, Penicillamine and similar agents, Bucillamine. Muscle relaxant active substances; Peripherally acting agents, Curare alkaloids, Alcuronium, Tubocurarine, Dimethyltubocurarine, Choline derivatives, Suxamethonium, Other quaternary ammonium compounds, Pancuronium, Gallamine, Vecuronium, Atracurium, Hexafluronium, Pipecuronium bromide, Doxacurium chloride, Fazadinium bromide, Rocuronium bromide, Mivacurium chloride, Cisatracurium, Botulinum toxin, Centrally acting agents, Carbamic acid esters, Phenprobamate, Carisoprodol, Methocarbamol, Styramate, Febarbamate, Oxazol, thiazine, and triazine derivatives, Chlormezanone, Chlorzoxazone, Ethers, chemically close to antihistamines, Orphenadrine, Other centrally acting agents, Baclofen, Tizanidine, Pridinol, Tolperisone, Thiocolchicoside, Mephenesin, Tetrazepam, Cyclobenzaprine, Fenyramidol, Directly acting agents, Dantrolene and derivatives. Antigout active substances; Preparations inhibiting uric acid production, Allopurinol, Tisopurine, Febuxostat, Preparations increasing uric acid excretion, Probenecid, Sulfinpyrazone, Benzbromarone, Isobromindione, Preparations with no effect on uric acid metabolism, Colchicine, Cinchophen, Other antigout preparations, Urate oxidase. Active substances affecting bone struture and mineralization; Bisphosphonates, Etidronic acid, Clodronic acid, Pamidronic acid, Alendronic acid, Tiludronic acid, Ibandronic acid, Risedronic acid, Zoledronic acid, Bone morphogenetic proteins, Dibotermin alfa, Eptotermin alfa, Other drugs affecting bone structure and mineralization, Ipriflavone, Aluminium chlorohydrate, Strontium ranelate, Quinine and derivatives, Hydroquinine, Enzymes, Chymopapain, Trypsin, Hyaluronic acid. Colecalciferol.

Analgesics; Opioids, Natural opium alkaloids, Morphine, Opium, Hydromorphone, Nicomorphine, Oxycodone, Dihydrocodeine, Diamorphine, Papaveretum, Codeine, Phenylpiperidine derivatives, Ketobemidone, Pethidine, Fentanyl, Diphenylpropylamine derivatives, Dextromoramide, Piritramide, Dextropropoxyphene, Bezitramide, Methadone, Benzomorphan derivatives, Pentazocine, Phenazocine, Oripavine derivatives, Buprenorphine, Morphinan derivatives, Butorphanol, Nalbuphine, Tilidine, Tramadol, Dezocine, Salicylic acid and derivatives, Acetylsalicylic acid, Aloxiprin, Choline salicylate, Sodium salicylate, Salicylamide, Salsalate, Ethenzamide, Morpholine salicylate, Dipyrocetyl, Benorilate, Diflunisal, Potassium salicylate, Guacetisal, Carbasalate calcium, Imidazole salicylate, Pyrazolones, Phenazone, Metamizole sodium, Aminophenazone, Propyphenazone, Nifenazone, Anilides, Paracetamol, Phenacetin, Bucetin, Propacetamol, Other analgesics and antipyretics, Rimazolium, Glafenine, Floctafenine, Viminol, Nefopam, Flupirtine, Ziconotide. Anesthetics; Ethers, Diethyl ether, Vinyl ether, Halogenated hydrocarbons, Halothane, Chloroform, Methoxyflurane, Enflurane, Trichloroethylene, Isoflurane, Desflurane, Sevoflurane, Barbiturates, Methohexital, Hexobarbital, Thiopental, Narcobarbital, Opioid anesthetics, Fentanyl, Alfentanil, Sufentanil, Phenoperidine, Anileridine, Remifentanil, Other general anesthetics, Droperidol, Ketamine, Propanidid, Alfaxalone, Etomidate, Propofol, Hydroxybutyric acid, Nitrous oxide, Esketamine, Xenon, Esters of aminobenzoic acid, Metabutethamine, Procaine, Tetracaine, Chloroprocaine, Benzocaine, Amides, Bupivacaine, Lidocaine, Mepivacaine, Prilocaine, Butanilicaine, Cinchocaine, Etidocaine, Articaine, Ropivacaine, Levobupivacaine, Esters of benzoic acid, Cocaine, Other local anesthetics, Ethyl chloride, Dyclonine, Phenol, Capsaicin. Antimigraine active substances; Ergot alkaloids, Dihydroergotamine, Ergotamine, Methysergide, Lisuride, Corticosteroid derivatives, Flumedroxone, Selective serotonin (5HT1) agonists, Sumatriptan, Naratriptan, Zolmitriptan, Rizatriptan, Almotriptan, Eletriptan, Frovatriptan, Other antimigraine preparations, Pizotifen, Clonidine, Iprazochrome, Dimetotiazine, Oxetorone. Antiepileptic active substances; Barbiturates and derivatives, Methylphenobarbital, Phenobarbital, Primidone, Barbexaclone, Metharbital, Hydantoin derivatives, Ethotoin, Phenytoin, Amino(diphenylhydantoin) valeric acid, Mephenytoin, Fosphenytoin, Oxazolidine derivatives, Paramethadione, Trimethadione, Ethadione, Succinimide derivatives, Ethosuximide, Phensuximide, Mesuximide, Benzodiazepine derivatives, Clonazepam, Carboxamide derivatives, Carbamazepine, Oxcarbazepine, Rufinamide, Fatty acid derivatives, Valproic acid, Valpromide, Aminobutyric acid, Vigabatrin, Progabide, Tiagabine, Other antiepileptics, Sultiame, Phenacemide, Lamotrigine, Felbamate, Topiramate, Gabapentin, Pheneturide, Levetiracetam, Zonisamide, Pregabalin, Stiripentol, Lacosamide, Beclamide. Anticholinergic active substances; Tertiary amines, Trihexyphenidyl, Biperiden, Metixene, Procyclidine, Profenamine, Dexetimide, Phenglutarimide, Mazaticol, Bornaprine, Tropatepine, Ethers chemically close to antihistamines, Etanautine, Orphenadrine (chloride), Ethers of tropine or tropine derivatives, Benzatropine, Etybenzatropine. Dopaminergic ative substances; Dopa and dopa derivatives, Levodopa, Melevodopa, Etilevodopa, Adamantane derivatives, Amantadine, Dopamine agonists, Bromocriptine, Pergolide, Dihydroergocryptine mesylate, Ropinirole, Pramipexole, Cabergoline, Apomorphine, Piribedil, Rotigotine, Monoamine, oxidase B inhibitors, Selegiline, Rasagiline, Other dopaminergic agents, Tolcapone, Entacapone, Budipine. Antipsychotic active substances; Phenothiazines with aliphatic side-chain, Chlorpromazine, Levomepromazine, Promazine, Acepromazine, Triflupromazine, Cyamemazine, Chlorproethazine, Phenothiazines with piperazine structure, Dixyrazine, Fluphenazine, Perphenazine, Prochlorperazine, Thiopropazate, Trifluoperazine, Acetophenazine, Thioproperazine, Butaperazine, Perazine, Phenothiazines with piperidine structure, Periciazine, Thioridazine, Mesoridazine, Pipotiazine, Butyrophenone derivatives, Haloperidol, Trifluperidol, Melperone, Moperone, Pipamperone, Bromperidol, Benperidol, Droperidol, Fluanisone, Indole derivatives, Oxypertine, Molindone, Sertindole, Ziprasidone, Thioxanthene derivatives, Flupentixol, Clopenthixol, Chlorprothixene, Tiotixene, Zuclopenthixol, Diphenylbutylpiperidine derivatives, Fluspirilene, Pimozide, Penfluridol, Diazepines, oxazepines and thiazepines, Loxapine, Clozapine, Olanzapine, Quetiapine, Neuroleptics, in tardive dyskinesia, Tetrabenazine, Benzamides, Sulpiride, Sultopride, Tiapride, Remoxipride, Amisulpride, Veralipride, Levosulpiride, Lithium, Other antipsychotics, Prothipendyl, Risperidone, Clotiapine, Mosapramine, Zotepine, Aripiprazole, Paliperidone. Anxiolytic active substances; Benzodiazepine derivatives, Diazepam, Chlordiazepoxide, Medazepam, Oxazepam, Potassium clorazepate, Lorazepam, Adinazolam, Bromazepam, Clobazam, Ketazolam, Prazepam, Alprazolam, Halazepam, Pinazepam, Camazepam, Nordazepam, Fludiazepam, Ethyl loflazepate, Etizolam, Clotiazepam, Cloxazolam, Tofisopam, Diphenylmethane derivatives, Hydroxyzine, Captodiame, Carbamates, Meprobamate, Emylcamate, Mebutamate, Dibenzo-bicyclo-octadiene derivatives, Benzoctamine, Azaspirodecanedione derivatives, Buspirone, Other anxiolytics, Mephenoxalone, Gedocarnil, Etifoxine. Hypnotic and sedative active substances; Barbiturates, Pentobarbital, Amobarbital, Butobarbital, Barbital, Aprobarbital, Secobarbital, Talbutal, Vinylbital, Vinbarbital, Cyclobarbital, Heptabarbital, Reposal, Methohexital, Hexobarbital, Thiopental, Etallobarbital, Allobarbital, Proxibarbal, Aldehydes and derivatives, Chloral hydrate, Chloralodol, Acetylglycinamide chloral hydrate, Dichloralphenazone, Paraldehyde, Benzodiazepineemepronium derivatives, Flurazepam, Nitrazepam, Flunitrazepam, Estazolam, Triazolam, Lormetazepam, Temazepam, Midazolam, Brotizolam, Quazepam, Loprazolam, Doxefazepam, Cinolazepam, Piperidinedione derivatives, Glutethimide, Methyprylon, Pyrithyldione, Benzodiazepine related drugs, Zopiclone, Zolpidem, Zaleplon, Ramelteon, Other hypnotics and sedatives, Methaqualone, Clomethiazole, Bromisoval, Carbromal, Scopolamine, Propiomazine, Triclofos, Ethchlorvynol, Valerian, Hexapropymate, Bromides, Apronal, Valnoctamide, Methylpentynol, Niaprazine, Melatonin, Dexmedetomidine, Dipiperonylaminoethanol. Antidepressant active substances; Non-selective monoamine reuptake inhibitors, Desipramine, Imipramine, Imipramine oxide, Clomipramine, Opipramol, Trimipramine, Lofepramine, Dibenzepin, Amitriptyline, Nortriptyline, Protriptyline, Doxepin, Iprindole, Melitracen, Butriptyline, Dosulepin, Amoxapine, Dimetacrine, Amineptine, Maprotiline, Quinupramine, Selective serotonin reuptake inhibitors, Zimeldine, Fluoxetine, Citalopram, Paroxetine, Sertraline, Alaproclate, Fluvoxamine, Etoperidone, Escitalopram, Monoamine oxidase inhibitors, non-selective, Isocarboxazid, Nialamide, Phenelzine, Tranylcypromine, Iproniazid, Iproclozide, Monoamine oxidase A inhibitors, Moclobemide, Toloxatone, Other antidepressants, Oxitriptan, Tryptophan, Mianserin, Nomifensine, Trazodone, Nefazodone, Minaprine, Bifemelane, Viloxazine, Oxaflozane, Mirtazapine, Medifoxamine, Tianeptine, Pivagabine, Venlafaxine, Milnacipran, Reboxetine, Gepirone, Duloxetine, Agomelatine, Desvenlafaxine, Centrally acting sympathomimetics, Amfetamine, Dexamfetamine, Metamfetamine, Methylphenidate, Pemoline, Fencamfamin, Modafinil, Fenozolone, Atomoxetine, Fenetylline, Xanthine derivatives, Caffeine, Propentofylline, Other psychostimulants and nootropics, Meclofenoxate, Pyritinol, Piracetam, Deanol, Fipexide, Citicoline, Oxiracetam, Pirisudanol, Linopirdine, Nizofenone, Aniracetam, Acetylcarnitine, Idebenone, Prolintane, Pipradrol, Pramiracetam, Adrafinil, Vinpocetine. Anti-dementia active subtances; Anticholinesterases, Tacrine, Donepezil, Rivastigmine, Galantamine, Other anti-dementia drugs, Memantine, *Ginkgo biloba*. Other nervous system active substances; Parasympathomimetics, Anticholinesterases, Neostigmine, Pyridostigmine, Distigmine, Ambenonium, Choline esters, Carbachol, Bethanechol, Other parasympathomimetics, Pilocarpine, Choline alfoscerate. Active substances used in addictive disorders; Drugs used in nicotine dependence, Nicotine, Bupropion, Varenicline, Drugs used in alcohol dependence, Disulfiram, Calcium carbimide, Acamprosate, Naltrexone, Drugs used in opioid dependence, Buprenorphine, Methadone, Levacetylmethadol, Lofexidine. Antivertigo active subtances; Betahistine, Cinnarizine, Flunarizine, Acetylleucine, other nervous system drugs, Gangliosides and ganglioside derivatives, Tirilazad, Riluzole, Xaliproden, Hydroxybutyric acid, Amifampridine.

Active substances against amoebiasis and other protozoal diseases; Hydroxyquinoline derivatives, Broxyquinoline, Clioquinol, Chlorquinaldol, Tilbroquinol, Nitroimidazole derivatives, Metronidazole, Tinidazole, Ornidazole, Azanidazole, Propenidazole, Nimorazole, Secnidazole, Dichloroacetamide derivatives, Diloxanide, Clefamide, Etofamide, Teclozan, Arsenic compounds, Arsthinol, Difetarsone, Glycobiarsol, Chiniofon, Emetine, Phanquinone, Mepacrine, Atovaquone, Trimetrexate, Tenonitrozole, Dihydroemetine, Fumagillin, Nitazoxanide. Antimalarial active substances; Aminoquinolines, Chloroquine, Hydroxychloroquine, Primaquine, Amodiaquine, Biguanides, Proguanil, Cycloguanil embonate, Methanolquinolines, Quinine, Mefloquine, Diaminopyrimidines, Pyrimethamine, Artemisinin and derivatives, Artemether, Artesunate, Artemotil, Artenimol, Halofantrine. Active substances against leishmaniasis and trypanosomiasis; Nitroimidazole derivatives, Benznidazole, Antimony compounds, Meglumine antimonate, Sodium stibogluconate, Nitrofuran derivatives, Nifurtimox, Nitrofural, Arsenic compounds, Melarsoprol, Acetarsol, Pentamidine isethionate, Suramin sodium, Eflornithine. Antitrematodal active substances; Quinoline derivatives and related substances, Praziquantel, Oxamniquine, Organophosphorous compounds, Metrifonate, Bithionol, Niridazole, Stibophen, Triclabendazole. Antinematodal active substances; Benzimidazole derivatives, Mebendazole, Tiabendazole, Albendazole, Ciclobendazole, Flubendazole, Fenbendazole, Piperazine and derivatives, Diethylcarbamazine, Tetrahydropyrimidine derivatives, Pyrantel, Oxantel, Imidazothiazole derivatives, Levamisole, Avermectines, Ivermectin, Pyrvinium, Bephenium, anticestodal active substance; Salicylic acid derivatives, Niclosamide, Desaspidin, Dichlorophen. Ectoparasiticide active substances; Sulfur containing products, Dixanthogen, Potassium polysulfide, Mesulfen, Disulfiram, Thiram, Chlorine containing products, Clofenotane, Lindane, Pyrethrines, incl. synthetic compounds, Pyrethrum, Bioallethrin, Phenothrin, Permethrin, Benzyl benzoate, Copper oleinate, Malathion, Quassia. Insecticide and repellent active substances; Pyrethrines, Cyfluthrin, Cypermethrin, Decamethrin, Tetramethrin, Diethyltoluaide, Dimethylphthalate, Dibutylphthalate, Dibutylsuccinate, Dimethylcarbate, Etohexadiol.

Decongestant active substances; Sympathomimetics, Cyclopentamine, Ephedrine, Phenylephrine, Oxymetazoline, Tetryzoline, Xylometazoline, Naphazoline, Tramazoline, Metizoline, Tuaminoheptane, Fenoxazoline, Tymazoline, Epinephrine, Cromoglicic acid, Levocabastine, Azelastine, Antazoline, Spaglumic acid, Thonzylamine, Nedocromil, Olopatadine, Corticosteroids, Beclometasone, Prednisolone, Dexamethasone, Flunisolide, Budesonide, Betamethasone, Tixocortol, Fluticasone, Mometasone, Triamcinolone, Fluticasone furoate, Hydrocortisone, Calcium hexamine thiocyanate, Retinol, Ipratropium bromide, Ritiometan, Mupirocin, Hexamidine, Framycetin, Phenylpropanolamine, Pseudoephedrine, Phenylephrine. Throat active substances; Antiseptics, Ambazone, Dequalinium, Dichlorobenzyl alcohol, Chlorhexidine, Cetylpyridinium, Benzethonium, Myristyl-benzalkonium, Chlorquinaldol, Hexylresorcinol, Acriflavinium chloride, Oxyquinoline, Povidoneiodine, Benzalkonium, Cetrimonium, Hexamidine, Phenol, Antibiotics, Neomycin, Tyrothricin, Fusafungine, Bacitracin, Gramicidin, Benzocaine, Lidocaine, Cocaine, Dyclonine. Active substances for obstructive airway diseases; Orciprenaline, Salbutamol, Terbutaline, Fenoterol, Rimiterol, Hexoprenaline, Isoetarine, Pirbuterol, Tretoquinol, Carbuterol, Tulobuterol, Salmeterol, Formoterol, Clenbuterol, Reproterol, Procaterol, Bitolterol, Glucocorticoids, Beclometasone, Budesonide, Flunisolide, Betamethasone, Fluticasone, Triamcinolone, Mometasone, Ciclesonide, Ipratropium bromide, Oxitropium bromide, Stramoni preparations, Tiotropium bromide, Cromoglicic acid, Nedocromil, Fenspiride, Methoxyphenamine, Bambuterol, Xanthines, Diprophylline, Choline theophyllinate, Proxyphylline, Theophylline, Aminophylline, Etamiphylline, Theobromine, Bamifylline, Acefylline piperazine, Bufylline, Doxofylline, Zafirlukast, Pranlukast, Montelukast, Ibudilast, Amlexanox, Eprozinol, Fenspiride, Omalizumab, Seratrodast, Roflumilast. Cough and cold active substances; Expectorants, Tyloxapol, Potassium iodide, Guaifenesin, *Ipecacuanha*, Althea root, Senega, Antimony pentasulfide, Creosote, Guaiacolsulfonate, Levoverbenone, Mucolytics, Acetylcysteine, Bromhexine, Carbocisteine, Eprazinone, Mesna, Ambroxol, Sobrerol, Domiodol, Letosteine, Stepronin, Tiopronin, Dornase alfa (desoxyribonuclease), Neltenexine, Erdosteine, Opium alkaloids and derivatives, Ethylmorphine, Hydrocodone, Codeine, Opium alkaloids with morphine, Normethadone, Noscapine, Pholcodine, Dextromethorphan, Thebacon, Dimemorfan, Acetyldihydrocodeine, Benzonatate, Benproperine, Clobutinol, Isoaminile, Pentoxyverine, Oxolamine, Oxeladin, Clofedanol, Pipazetate, Bibenzonium bromide, Butamirate, Fedrilate, Zipeprol, Dibunate, Droxypropine, Prenoxdiazine, Dropropizine, Cloperastine, Meprotixol, Piperidione, Tipepidine, Morclofone, Nepinalone, Levodropropizine, Dimethoxanate. Antihistamine active substances; Aminoalkyl ethers, Bromazine, Diphenhydramine, Clemastine, Chlorphenoxamine, Diphenylpyraline, Carbinoxamine, Doxylamine, Substituted alkylamines, Brompheniramine, Dexchlorpheniramine, Dimetindene, Chlorphenamine, Pheniramine, Dexbrompheniramine, Talastine, Substituted ethylene diamines, Mepyramine, Histapyrrodine, Chloropyramine, Tripelennamine, Methapyrilene, Thonzylamine, Phenothiazine derivatives, Alimemazine, Promethazine, Thiethylperazine, Methdilazine, Hydroxyethylpromethazine, Thiazinam, Mequitazine, Oxomemazine, Isothipendyl, Piperazine derivatives, Buclizine, Cyclizine, Chlorcyclizine, Meclozine, Oxatomide, Cetirizine, Levocetirizine, Bamipine, Cyproheptadine, Thenalidine, Phenindamine, Antazoline, Triprolidine, Pyrrobutamine, Azatadine, Astemizole, Terfenadine, Loratadine, Mebhydrolin, Deptropine, Ketotifen, Acrivastine, Azelastine, Tritoqualine, Ebastine, Pimethixene, Epinastine, Mizolastine, Fexofenadine, Desloratadine, Rupatadine, Other respiratory system active substances; Lung surfactants, Colfosceril palmitate, Natural phospholipids, Respiratory stimulants, Doxapram, Nikethamide, Pentetrazol, Etamivan, Bemegride, Prethcamide, Almitrine, Dimefline, Mepixanox, Nitric oxide.

Other active substances; Antidotes, *Ipecacuanha*, Nalorphine, Edetates, Pralidoxime, Prednisolone and promethazine, Thiosulfate, Sodium nitrite, Dimercaprol, Obidoxime, Protamine, Naloxone, Methylthioninium chloride, Potassium permanganate, Physostigmine, Copper sulfate, Potassium iodide, Amyl nitrite, Acetylcysteine, *Digitalis* antitoxin, Flumazenil, Methionine, 4-dimethylaminophenol, Cholinesterase, Prussian blue, Glutathione, Hydroxocobalamin, Fomepizole, Iron chelating agents, Deferoxamine, Deferiprone, Deferasirox, Polystyrene sulfonate, Sevelamer, Lanthanum carbonate, Mesna, Dexrazoxane, Calcium folinate, Calcium levofolinate, Amifostine, Sodium folinate, Rasburicase, Palifermin, Glucarpidase, Sodium cellulose phosphate, Diazoxide.

In specific embodiments, the active substance is for cardiac therapy including e.g. cardiac glycosides, antiarrhythmics, cardiac stimulants, vasodilators, antihypertensives, diuretics, vasoprotectives, beta blockers, calcium channel blockers, agents acting on the rennin-angiotensin system, lipid modifying agents.

In specific embodiments, the active substance is from the therapeutic classes including antiemetics, antinauseants, antiobesity and anabolic agents.

In specific embodiments, the active substance is from the therapeutic classes including antiinflammatory and antiinfective agents, corticosteroids, non-steroids anti-inflammatory and antirheumatic agents.

In specific embodiments, the active substance is from the therapeutic classes including decongestants, adrenergics, expectorants, cough suppressant and antihistamines.

In specific embodiments, the active substance is from the therapeutic classes including anesthetics, analgesics, opioids, antipyretics, antimigraine agents, antiepileptics, antiparkinson agents, dopaminergic agents, antipsychotics, anxiolytics, sedatives, antidepressants, psychostimulants agents used for ADHD and nootropics, agents used in addictive disorders.

In specific embodiments, the active substance is from the therapeutic classes including anaesthetics, centrally-acting analgesics, sedative-hypnotics, anxiolytics; appetite suppressants, decongestants, antitussives, antihistamines, antiemetics, antidiarrheals, and drugs used to treat narcolepsy and attention deficit hyperactivity disorder.

In specific embodiments, the active substance is associated with abuse syndromes include opioids, CNS depressants, CNS stimulants, cannabinoids, nicotine-like compounds, glutamate antagonists and N-methyl-D-aspartate (NMDA) antagonists.

In specific embodiments, the active substance is buprenorphine, codeine, dextromoramide, dihydrocodeine, fentanyl, hydrocodone, hydromorphone, morphine, pentazocine, oxycodeine, oxycodone, oxymorphone and tramadol.

The active substance can be in various forms, such as uncharged or charged molecules, molecular complexes, crystalline forms, amorphous form, polyamorphous form, polymorphous form, complexes, solvates, anhydrates, if relevant isomers, enantiomers, racemic mixtures and pharmacologically acceptable salts such as e.g. hydrochloride, hydrobromide, sulfate, laurylate, palmitate, phosphate, nitrite, nitrate, citrate, borate, acetate, maleate, tartrate, oleate, and salicylate. For acidic active substance, salts of metals e.g. alkali metal salts such as, e.g., sodium or potassium salts, alkaline earth metal salts such as, e.g., calcium and magnesium salts, amines amino acids or organic cations, quaternary ammoniums, can be used. Derivatives of active substances such as esters, ethers and amides which have solubility characteristics suitable for use herein can be used alone or mixed with other drugs. After release of the derivative from the drug delivery system it may be converted by enzymes, hydrolysed by body pH or other metabolic processes to the parent drug or to another biologically active form.

A pharmaceutical composition of the invention may in addition be suitable for the delivery of peptides, polypeptides or proteins, for example hormones, enzymes such as lipases, proteases, carbohydrates, amylases, lactoferrin, lactoperoxidases, lysozymes, nanoparticles, etc., and antibodies. The composition may also be employed for the delivery of microorganisms, either living, attenuated or dead, for example bacteria, e.g. gastrointestinal bacteria such as streptococci, e.g. *S. faecium, Bacillus* spp. such as *B. subtilis* and *B. licheniformis*, lactobacteria, *Aspergillus* spp., bifidogenic factors, or viruses such as indigenous vira, enterovira, bacteriophages, e.g. as vaccines, and fungi such as baker's yeast, *Saccharomyces cerevisiae* and fungi imperfecti.

In an embodiment of the invention, the active substance is a pharmaceutically active powder. The powder typically has a particle size of from about 0.1 μm to about 500 μm, typically from about 0.5 μm to about 300 μm, more typically from about 1 μm to about 200 μm, especially from about 5 μm to about 100 μm.

In an embodiment of the invention, the active substance is a pharmaceutically active crystal. The crystal typically has a particle size of from about 0.1 μm to about 1000 μm such as, e.g., about 0.1 μm to about 750 μm, about 0.1 μm to about 500 μm, typically from about 0.5 μm to about 500 μm, more typically from about 1 μm to about 500 μm, especially from about 5 μm to about 500 μm.

In another embodiment of the invention, a composition comprises active substance that at least partially is present in amorphous form with a mean particle size of at least about 0.01 μm such as, e.g., from about 0.01 μm to about 500 μm, from about 0.05 μm to about 500 μm, from about 0.1 μm to about 500 μm, from about 0.5 μm to about 500 μm, about 1 μm to about 500 μm, typically from about 0.5 μm to about 300 μm, more typically from about 1 μm to about 200 μm, especially from about 1 μm to about 100 μm.

The at least one therapeutically, prophylactically and/or diagnostically and/or biologically active substance will suitably be present in an amount of up to about 80%, typically up to about 70%, up to about 60% or up to about 50%, such as, e.g., from 0.1% to 80%, such as from 0.25% to 75%, such as from 0.5% to 60%, such as from 0.75% to 50%, such as from 1% to 40%, such as from 1.5% to 35%, such as from 1.75% to 30% by weight of the composition or layer. With respect to situations where one or more active substances are contained in one of the layers or coat, a content of about 60-80% w/w is contemplated to be the maximum content, which still allows for a sufficient content of the polymer and, when relevant, a pharmaceutically acceptable excipient in the composition. The active substance may, on the other hand, be present in the composition in much smaller amounts, depending on the nature and potency of the active substance in question.

A composition according to the invention containing a drug substance is typically for oral administration. Due to the possibility of controlling the release rate of the active substance the composition may be adapted for oral administration 1-6 times a day, normally 1-4 times daily such as 1-3 times, 1-2 times or 1 times daily. The technology may also provide compositions for administration only once or twice daily. In the present context the term "once daily" is intended to mean that it is only necessary to administer the pharmaceutical composition once a day in order to obtain a suitable therapeutic and/or prophylactic response; however, any administration may comprise co-administration of more than one dosage unit, such as, e.g. 2-4 dosage units if the amount of active substance required may not be formulated in only one composition or if a composition of a smaller size is preferred.

The dosage of the active substance depends on the particular substance, the age, weight condition etc. of the human or animal that will be treated with the composition etc. All such factors are well known to a person skilled in the art.

Stability

With respect to the fixed-dosed combination formulation stability is employed to encompass one or more of the following;
  1) Stability with respect to the physical stability of the composition (appearance, color, strength, etc.)
  2) Stability with respect to in vitro dissolution behavior of the active substance from the composition Stability of the Individual Components;
  3) Stability with respect to the chemical stability of the active substance (degradation of the active substance to other—normally—unwanted products)
  4) Stability with respect to the form the active substance has in the composition; if the active substance is dissolved (molecularly dispersed) in the polymer as a solid dispersion. In such cases precipitation or otherwise formation of crystals of the active substance in the composition is an indication of a stability problem.
  5) Physical and chemical stability of the pharmaceutically acceptable polymer and excipients employed In particular, the active substance or substances maybe stabilized in the dosage form in its amorphous form. The amorphous state and/or the solid dispersion is stabilized either by a very careful choice of the concentration of the active substance in the composition and/or by addition of suitable stabilizing agents acting by stabilizing one or more of the conditions mentioned above under items 1) to 5).

In regards to condition 4) the stability may be retrieved by several mechanisms of which the most important are
  a) Physical stabilization by decreasing the molecular mobility of the components, i.e. suitable excipients and the active substance of the formulation
  b) Chemical stabilization by increasing the apparent solubility of the active substance in the matrix formulation.

Thus a stabilizing agent may serve more than one purpose, it may stabilize the amorphous state of the active substance in the composition in order to avoid, reduce or delay any recrystallization, it may stabilize the active substance or other ingredients towards proteolytic or oxidative degradation or it may have an anti-plasticizing effect.

A stabilizing agent may also contribute to an improved solubility of the active substance. Without being bound to any theory it may be assumed that the stabilizing agent together with the polyethylene glycol and/or polyethylene oxide represent the dispersion medium wherein the solubility of the active substance may be higher than in the polyethylene glycol and/or polyethylene oxide alone. The same may apply with respect to the stability of the amorphous form of the active substance.

Pharmaceutically Acceptable Excipients

The composition may also contain other excipients as well, e.g. in order to improve the technical properties of the composition so that it may be easier to produce or in order to improve the properties of the composition such as release rate of the active substance, stability of the active substance or of the composition itself etc.

A suitable pharmaceutically acceptable excipient for use in a composition of the invention may be selected from the group consisting of fillers, diluents, disintegrants, glidants, pH-adjusting agents, viscosity adjusting agents, solubility increasing or decreasing agents, osmotically active agents and solvents.

Suitable excipients include conventional tablet or capsule excipients. These excipients may be, for example, diluents such as dicalcium phosphate, calcium sulfate, lactose or sucrose or other disaccharides, cellulose, cellulose derivatives, kaolin, mannitol, dry starch, glucose or other monosaccharides, dextrin or other polysaccharides, sorbitol, inositol or mixtures thereof; binders such as alginic acid, calcium alginate, sodium alginate, starch, gelatin, saccharides (including glucose, sucrose, dextrose and lactose), molasses, panwar gum, ghatti gum, mucilage of isapol husk, carboxymethylcellulose, methylcellulose, veegum, larch arabolactan, polyethylene glycols, ethylcellulose, water, alcohols, waxes, polyvinylpyrrolidone such as, e.g., PVP K90 or mixtures thereof; lubricants such as talc, silicium dioxide, magnesium stearate, calcium stearate, stearic acid, hydrogenated vegetable oils, sodium benzoate, sodium chloride, leucine, carbowax 4000, magnesium lauryl sulfate, Sodium laurilsulfate, Stearyl alcohol, Polysorbate 20, Polysorbate 60, Polysorbate 80, Macrogol stearate, Macrogol lauryl ether, Stearoyl macrogolglycerides, Sorbitan stearate, Sorbitan laurate, Macrogol glycerol hydroxystearat, colloidal silicon dioxide and mixtures thereof, disintegrants such as starches, clays, cellulose derivatives including microcrystalline cellulose, methycellulose, carboxymethycellulose calcium, carboxymethylcellulose sodium, cellulose, crosscarmellose sodium, gums, aligns, various combinations of hydrogencarbonates with weak acids (e.g. sodium hydrogencarbonate/tartaric acid or citric acid) crosprovidone, sodium starch glycolate, agar, alginic acid, calcium alginate, sodium alginate, chitosan, colloidal silicon dioxide, docusate sodium, guar gum, low-substituted hydroxypropyl cellulose, hydroxypropyl starch, magnesium aluminium silicate, polacrilin potassium, povidone, sodium starch glycolate, pregelatinized starch, cation exchange resins, citrus pulp, veegum, glycollate, natural sponge, bentonite, sucralfate, calcium hydroxyl-apatite or mixtures thereof, effervescent agents (carbonate release) such as citric acid, anhydrous, citric acid, monohydrate, dextrates, fumaric acid, potassium bicarbonate, sodium bicarbonate, sodium citrate, dehydrate, tartaric acid or mixtures thereof.

Furthermore, the composition may comprise one or more agents selected from the group consisting of sweetening agents, flavouring agents and colouring agents, in order to provide an elegant and palatable preparation. Examples are maltol, citric acid, water soluble FD&C dyes and mixtures thereof with corresponding lakes and direct compression sugars such as Di-Pac from Amstar. In addition, coloured dye migration inhibitors such as tragacanth, *acacia* or attapulgite talc may be added. Specific examples include Calcium carbonate, 1,3,5-trihydroxybenzene, Chromium-cobalt-aluminium oxide, ferric ferrocyanide, Ferric oxide, Iron ammonium citrate, Iron (III) oxide hydrated, Iron oxides, Carmine red, Magnesium carbonate and Titanium dioxide.

Plasticizer may be incorporated in the composition. A suitable plasticizer is selected from such as e.g. mono- and di-acetylated monoglycerides, diacetylated monoglycerides, acetylated hydrogenated cottonseed glyceride, glyceryl cocoate, Polyethylene glycols or polyethylene oxides (e.g. with a molecular weight of about 1,000-500,000 daltons), dipropylene glycol salicylate glycerin, fatty acids and esters, phthalate esters, phosphate esters, amides, diocyl phthalate, phthalyl glycolate, mineral oils, hydrogenated vegetable oils, vegetable oils, acetylated hydrogenated soybean oil glycerides, Castor oil, acetyl tributyl citrate, acetyl triethyl citrate, methyl abietate, nitrobenzene, carbon disulfide, β-naphtyl salicylate, sorbitol, sorbitol glyceryl tricitrate, fatty alcohols, cetostearyl alcohol, cetyl alcohol, stearyl alcohol, oleyl alcohol, myristyl alcohol, sucrose octaacetate, alfa-tocopheryl polyethylene glycol succinate (TPGS), tocopheryl derivative, diacetylated monoglycerides, diethylene glycol monostearate, ethylene glycol monostearate, glyceryl monooleate, glyceryl monostearate, propylene glycol monostearate, macrogol esters, macrogol stearate 400, macrogol stearate 2000, polyoxyethylene 50 stearate, macrogol ethers, cetomacrogol 1000, lauromacrogols, nonoxinols, octocinols, tyloxapol, poloxamers, polyvinyl alcohols, polysorbate 20, polysorbate 40, polysorbate 60, polysorbate 65, polysorbate 80, polysorbate 85, sorbitan monolaurate, sorbitan monooleate, sorbitan monopalmitate, sorbitan monostearate, sorbitan sesquioleate, sorbitan trioleate, sorbitan tristearate and sucrose esters, amyl oleate, butyl oleate, butyl stearate, diethylene glycol monolaurate, glycerol tributyrate, Cumar W-1, Cumar MH-1, Cumar V-1, Flexol B-400, monomeric polyethylene ester, Piccolastic A-5, Piccalastic A-25, Beckolin, Clorafin 40, acetyl tributyl citrate, acetyl triethyl citrate, benzyl benzoate, butoxyethyl stearate, butyl and glycol esters of fatty acids, butyl diglycol carbonate, butyl ricinoleate, butyl phthalyl butyl glycolate, camphor, dibutyl sebacate, dibutyl tartrate, diphenyl oxide, glycerine, HB-40, hydrogenated methyl ester of rosin, methoxyethyl oleate, monoamylphthalate, Nevillac 10, Paracril 26, technical hydroabietyl alcohol, triethylene glycol dipelargonate, solid aliphatic alcohols, nitrobenzene, carbon disulfide, β-naphtyl salicylate, phthalyl glycolate, dioctyl phthalate. and mixtures thereof. Other suitable plasticizers appear from EP-B-0 746 310 to which reference is made.

The use of a plasticizer will often be desirable in order to improve the processibility of the coating. The plasticizer may also be a non-ionic surfactant, e.g. a non-ionic surfactant as the one mentioned above.

Preferred stabilizers (chemical) include TPG e.g. in the form of TPGS due to surfactant properties, BHA, BHT, t-butyl hydroquinone, calcium ascorbate, gallic acid, hydroquinone, maltol, octyl gallate, sodium bisulfite, sodium metabisulfite, tocopherol and derivates thereof, citric acid, tartaric acid, and ascorbic acid. Other stabilisers include trivalent phosphorous like e.g. phosphite, phenolic antioxidants, hydroxylamines, lactones such as substituted benzofuranones. Hindered phenols, thiosynergists and/or hindered amines, acids (ascorbic acid, erythorbic acid, etidronic acid, hypophosphorous acid, nordihydroguaiaretic acid, propionic acid etc.), phenols, dodecyl gallate, octyl gallate, 1,3,5-trihydroxybenzene, organic and inorganic salts (calcium ascorbate, sodium ascorbate, sodium bisulphite, sodium metabisulfite, sodium sulfite, potassium bisulphite, potassium metabisulphite), esters (calcium ascorbate, dilauryl thiodipropionate, dimyristyl thiodipropionate, distearyl thiodipropionate), pyranon (maltol), and vitamin E (tocopherol, D-α-tocopherol, DL-α-tocopherol, tocopheryl acetate, d-α-tocopheryl acetate, dl-α-tocopheryl acetate. However, other anti-oxidative agents known in the art may be used according to the present invention. Other suitable stabilizer is selected from such as e.g. sorbitol glyceryl tricitrate, sucrose octaacetate.

Modifier may be incorporated in the composition. A suitable modifier is selected from such as e.g. fatty acids and esters, fatty alcohols, cetyl alcohol, stearyl alcohol, mineral oils, hydrogenated vegetable oils, vegetable oils, acetylated hydrogenated soybean oil glycerides, Castor oil, phosphate esters, amides, phthalate esters, glyceryl cocoate oleyl alcohol, myristyl alcohol, sucrose octaacetate, diacetylated monoglycerides, diethylene glycol monostearate, ethylene glycol monostearate, glyceryl monooleate, glyceryl monostearate, propylene glycol monostearate, macrogol esters, macrogol stearate 400, macrogol stearate 2000, polyoxyethylene 50 stearate, macrogol ethers, cetomacrogol 1000, lauromacrogols, poloxamers, polyvinyl alcohols, sorbitan monolaurate, sorbitan monooleate, sorbitan monopalmitate, sorbitan monostearate, sorbitan sesquioleate, sorbitan trioleate, sorbitan tristearate, ethylcellulose, cellulose acetate, cellulose propionate, cellulose nitrate, cellulose derivative selected from the group consisting of methylcellulose, carboxymethylcellulose and salts thereof, cellulose acetate phthalate, microcrystalline cellulose, ethylhydroxyethylcellulose, ethylmethylcellulose, hydroxyethylcellulose, hydroxyethylmethylcellulose, hydroxypropylcellulose, hydroxypropylmethylcellulose, hydroxymethylcellulose and hydroxymethylpropylcellulose, cellulose acetate, polylactic acid or polyglycolic acid and copolymers thereof, methacrylates, a co-polymer of methacrylate-galactomannan etc., Polyvinyl alcohols, glycerinated gelatin, cocoa butter Other suitable modifier may be selected from the group consisting of inorganic acids, inorganic bases, inorganic salts, organic acids or bases and pharmaceutically acceptable salts thereof, saccharides, oligosaccharides, polysaccharides, polyethylene glycol derivatives and cellulose and cellulose derivatives.

Alternatively or additionally, a suitable pharmaceutically acceptable excipient is a mono-, di-, oligo, polycarboxylic acid or amino acids such as, e.g. acetic acid, succinic acid, citric acid, tartaric acid, acrylic acid, benzoic acid, malic acid, maleic acid, sorbic acid etc., aspartic acid, glutamic acid etc.

Examples of suitable organic acids include acetic acid/ ethanoic acid, adipic acid, angelic acid, ascorbic acid/vitamin C, carbamic acid, cinnamic acid, citramalic acid, formic acid, fumaric acid, gallic acid, gentisic acid, glutaconic acid, glutaric acid, glyceric acid, glycolic acid, glyoxylic acid, lactic acid, levulinic acid, malonic acid, mandelic acid, oxalic acid, oxamic acid, pimelic acid, and pyruvic acid.

Examples of suitable inorganic acids include pyrophosphoric, glycerophosphoric, phosphoric such as ortho and meta phosphoric, boric acid, hydrochloric acid, and sulfuric acid.

Examples of suitable inorganic compounds include aluminium.

Examples of organic bases are p-nitrophenol, succinimide, benzenesulfonamide, 2-hydroxy-2cyclohexenone, imidazole, pyrrole, diethanolamine, ethyleneamine, tris(hydroxymethyl) aminomethane, hydroxylamine and derivates of amines, sodium citrate, aniline, hydrazine.

Examples of inorganic bases include aluminium oxide such as, e.g., aluminium oxide trihydrate, alumina, sodium hydroxide, potassium hydroxide, calcium carbonate, ammonium carbonate, ammonium hydroxide, KOH and the like.

Suitable pharmaceutically acceptable salts of an organic acid is e.g. an alkali metal salt or an alkaline earth metal salt such as, e.g. sodium phosphate, sodium dihydrogenphosphate, disodium hydrogenphosphate etc., potassium phosphate, potassium dihydrogenphosphate, potassium hydrogenphosphate etc., calcium phosphate, dicalcium phosphate etc., sodium sulfate, potassium sulfate, calcium sulfate, sodium carbonate, sodium hydrogencarbonate, potassium carbonate, potassium hydrogencarbonate, calcium carbonate, magnesium carbonate etc., sodium acetate, potassium acetate, calcium acetate, sodium succinate, potassium succinate, calcium succinate, sodium citrate, potassium citrate, calcium citrate, sodium tartrate, potassium tartrate, calcium tartrate etc.

A suitable inorganic salt for use in a matrix composition of the invention is sodium chloride, potassium chloride, calcium chloride, magnesium chloride etc.

Saccharides such as glucose, ribose, arabinose, xylose, lyxose, xylol, allose, altrose, inosito, glucose, sorbitol, mannose, gulose, Glycerol, idose, galactose, talose, mannitol, erythritol, ribitol, xylitol, maltitol, isomalt, lactitol, sucrose, fructose, lactose, dextrin, dextran, amylose, xylan.

Polyethylene glycol derivatives such as e.g. polyethylene glycol di(2-ethyl hexoate), polyethylene glycols (200-600 daltons) or polyethylene oxides, e.g. with a molecular weight of about 800-500,000 daltons, typically about 1,000-100,000 daltons, more typically 1,000-50,000 daltons, especially about 1,000-10,000 daltons, in particular about 1,500-5,000 daltons, and mixtures thereof.

Cellulose and cellulose derivative selected from the group consisting of methylcellulose, carboxymethylcellulose and salts thereof, microcrystalline cellulose, ethylhydroxyethylcellulose, ethylcellulose, cellulose acetate, cellulose proprionate, cellulose nitrate, cellulose acetate phthalate, ethylmethylcellulose, hydroxyethylcellulose, hydroxyethylmethylcellulose, hydroxypropylcellulose, hydroxypropylmethylcellulose, hydroxymethylcellulose and hydroxymethylpropylcellulose.

Preparation of a Composition of the Present Invention

A composition of the invention may be produced by various methods which are either known per se in the pharmaceutical industry or which, for example, are used in the production of polymer-based materials, depending upon the desired embodiment and the materials employed in the composition in question. One advantage of the composition according to the invention is that it may be produced by methods, which are relatively simple and inexpensive.

Suitable preparation methods for compositions according to the invention include extrusion, injection moulding, tabletting, capsule filling, thermoforming, spray coating, micro encapsulation and other methods suitable for preparation of controlled release compositions. Compositions according to the invention may be prepared in numerous ways giving rise to different release mechanisms. Particularly the composition may be prepared by 1, 2 or multiple component injection mouldings, by conventional tablet compression, by tablet compression and afterward temperature curing, by micro encapsulation, by 1, 2 or multiple component extrusions, by capsule filling or by thermoforming. In cases were a preparation is needed in order to make the controlled release properties before/after the above mentions preparation steps, the preparation may also comprise separate steps as for example wet granulation, dry granulation, melt granulation, pelletizing, roller compaction, spray coating, electrostatic coating or other forms of controlled release preparation methods.

In a particular example the composition is prepared by two/three component injection moulding of a matrix and a coat partly covering the matrix and exposing two ends of the composition for erosion governed release.

During the injection moulding process it is possible to place separately prepared components and include these in the final product by insert-moulding or similar methods. Further separately prepared components from injection moulding or other processes e.g. tablets, pellets etc. can be assembled in a separate, automated assembly process.

A composition may also be produced by, for example, injection moulding, co-extrusion of the coating with the matrix composition and the active substance, extrusion and dip coating, injection moulding and dip coating, or by extrusion or injection moulding and solvent coating by spraying or dipping, electrostatic coating. Multiple component injection moulding, or a combination of these methods.

The injection moulding technique have the advantage of simultaneous mixing and heating the components during increased pressure in a one step procedure without exposure to air and moisture because the injection moulding is performed in a single closed compartment from the time the blend has entered the machine to the final pharmaceutical units are ejected ready for packaging.

In a further aspect of the invention, the blending process may be followed by an extrusion step for obtaining pellets suitable for feeding of the injection moulding machines. The extruding step may secure a more intimate blending and thereby higher reproducibility of the final pharmaceutical product.

It should also be mentioned that the present technology also can be applied when it is desired to have an amorphous form of the active substance in the composition, because the most convenient process for the preparation of a composition of the invention involves heating of the polymer together with the active substance and the conversion from the crystalline state to the amorphous state requires addition of energy (heating).

Normally, when preparing a composition according to the invention heating is employed for e.g. an injection moulding process. During heating it has been observed that PEO in various qualities forms free radicals that results in the formation of inter alia formaldehyde and formic acid. These products may often lead to further degradation e.g. of the active substance present in the composition and it is therefore necessary to take the necessary precautions in this respect. Oxidative free radicals degradation by hydroperoxides can be catalysed by certain transition metal ions, especially those of copper, cobalt and manganese. Thus, employment of PEO qualities devoid of or only containing a very small amount of such transition metal ions may improve stability. Another possibility is to use component in a quality that ensures that free radicals formed, if any, do not significantly increase the degradation of the active substance in the composition. Such a quality could e.g. be a quality containing an antioxidant that functions by preventing the formation of free radical during heating or by scavenging any free radicals formed. Another possibility is to add such antioxidant to the formulation before any heating takes place.

A composition according to the invention may therefore further comprise one or more antioxidants that inhibits the formation of peroxides and/or inactivates any peroxides present.

Suitable antioxidants for use includes beta-caroten (a vitamin A precursor), ascorbic acid, ascorbyl palmitate, butylated hydroxyanisole, butylated hydroxytoluene, hypophosphorous acid, monothioglycerol, potassium metabisulfite, sodium metabisulfite, propyl gallate, sodium formaldehyde sulfoxylate, sodium thiosulfate, sulfur dioxide, tocopherol, tocopherol acetate, tocopherol hemisuccinate, TPGS or other tocopherol derivatives, sulfides, phosphine etc. Other suitable antioxidants are described herein.

It is believed that the amorphous state of the active substance is furthermore favoured by the processing procedures of the preparation of the product according to the present invention, which in a preferred embodiment involves injection moulding of the pharmaceutical units.

For further details reference is made to the experimental section herein.

Other Specific Embodiments of the Invention

In the following is described various embodiments of the present invention. These embodiments illustrate the flexibility of the technology to obtain different release patterns and the flexibility with respect to including two or more, the same or different, active substances in a composition of the invention in order to obtain a composition that releases the active substance in a different manner dependent on in which layer the active substance is present. Accordingly, a composition of the present invention can be designed to have release properties including burst release (very fast release of substantially the whole content in that part of the composition), controlled release (typically prolonged or extended release), delayed release (i.e. release only after a certain lag time) and immediate release (relatively fast release). Thus, the following types can be obtained:

If only one active substance is present in the composition:
Delayed release—immediate release
Delayed release—controlled release
Burst release—delayed release—immediate release
Burst release—delayed release—controlled release
Burst release—immediate release
Burst release—controlled release
Controlled release—Immediate release
Controlled release—controlled release If e.g. two different active substances (S1 and S2) are present, the following can be designed:
Delayed release for S1, but controlled release for S2—immediate release for S1
Delayed release for S1, but controlled release for S2—controlled release for S1
Burst release for S1 and/or S2—delayed release for S1, but controlled release for S2—immediate release S1
Burst release for S1 and/or S2—delayed release for S1, but controlled release for S2—controlled release for S1.
Burst release for S1 and/or S2—immediate release for S1 and/or S2
Burst release for S1 and/or S2—controlled release for S1 and/or S2 from multiple units
Controlled release for S1 and/or S2—Immediate release for S1 and/or S2
Controlled release for S1 and/or S2—controlled release for S1 and/or S2 from multiple units A person skilled in the art will know how to obtain other combinations in view of the guidelines given herein.

In a specific embodiment, the present invention provides a composition for controlled delivery of at least one active substance. It is possible to include two or more different active substances in the composition of the invention, adapted to enable release at different concentrations, intervals and/or release rates.

Apart from the content of an active substance in the inner layer, the same and/or a different active substance (second active substance) can be substantially homogeneously dispersed in the outer layer (the polymer matrix), in which case a substantially zero order release of the second active substance is obtained. Alternatively or in addition, a burst release of the same or a different active substance may be obtained in a composition of the invention which comprises alternating layers. In a composition comprising alternating layers, the alternating layers may comprise, respectively, none, one, two or more different active substances.

As described in detail above, an inner layer comprises a quick release function obtained by e.g. fast disintegration, exploding and/or effervescent effects.

The first fraction comprises
a) a disintegration agent, an exploding agent, an effervescent agent or a mixture thereof
b) optionally, an active substance
c) optionally, multiple units comprising an active substance and,
d) optionally, one or more pharmaceutically acceptable excipients The outer layers (matrix compositions) comprise
a) a polymer or a mixture of polymers,
b) optionally, an active substance and,
c) optionally, multiple units comprising an active substance and,
d) optionally, one or more pharmaceutically acceptable excipients.

A third component may also be present comprising
a) a polymer or a mixture of polymers,
b) optionally, one or more pharmaceutically acceptable excipients.

Due to the nature of the composition of the invention, it is possible to obtain a substantially controlled pulsatile/burst release, optionally in combination with a constant rate of release of the active substance over a specific period of time. The amount of drug release corresponds to the dosage necessary for the treatment in question, so that adherence to a strict dosage regimen, e.g. requiring administration of a drug at set intervals up to several times a day, may be dispensed with. It is possible to combine two or more active substances each following and independent release pattern however the release pattern of such substances may also be identical.

The matrix of the outer layer of a pharmaceutical composition of the invention may be designed to release an active substance, if any, in a controlled manner such as by a zero order release mechanism. Accordingly, the composition is also suitable for controlled release of an active substance, i.e. first a controlled release of an active substance (from the matrix, layer B) and then a relatively fast release of the same or different active substance (from the Layer A) or other suitable release combinations. In the present context the term "controlled release" is used to designate a release a desired rate during a predetermined release period. Terms like "modified", "delayed", "sustained", "prolonged", "extended" etc. release are in the present context synonyms to the term "controlled release". Normally, the term relates to compositions that have a slower release of the active ingredient than that of a plain tablet or a tablet designed for immediate release. A person skilled in the art knows of these terms.

In order to more detailed explain the invention; reference is made to (EP 0406315, EP 0493513, WO 2006/128471) herein although the invention is not limited to this type and shape of the composition. However, the general idea is to have a layered composition, wherein the layers are separate layers.

However, a person skilled in the art will understand that other forms may fulfil the same objective. The most simplified versions of the pharmaceutical composition according to the invention are either a sphere or an oval shaped first fraction surrounded by a sphere or an oval shaped second fraction, reference is made to (EP 0406315, EP 0493513, WO 2006/128471).

In one embodiment of the invention a double burst unit is presented by having a layered composition placed inside an immediate release tablet matrix in such a way that the outer matrix is eroded or disintegrated, exposing the layered composition, as shown in FIG. 1.

In one embodiment of the invention, the inner layer of a composition according to the invention comprises an active substance. The release of the active substance is delayed because the outer layer must erode before the first fraction is exposed to the gastrointestinal fluids after oral administration.

In one embodiment of the invention it is possible to obtain a substantially controlled burst release, optionally in combination with a constant rate of release over a specific period of time. It is possible to combine two or more active substances each following and independent release pattern however the release pattern of such substances may also be identical. It may in certain cases be desirable to incorporate a mixture of two active substances into the matrix in order to release both active substances in the matrix with the same release rate. In other cases it is desirable to have different release rates of the two active substances. In such cases the composition may be composed of two different matrixes, each with different release characteristics. In yet another case the release of the active substances may be sequential, such that during the initial dissolution phase one active substance S1 is released and then the other S2. In this case the second release is onset after a lag defined by the first release.

More specifically, without limiting the invention thereto, the invention is illustrated by the embodiments mentioned below. Various different formulations of layers A) and B) are given and any combination of layers A) and B) is contemplated (i.e. any of the layer B) of 1, 2, 5-9 may be combined with any of layer A) 3, 4, 10-14, and the multiple unit formulations 15 or 16 may be part of either layer A) or B), and the coat formulations 17 or 18 may be applied to any of the combined formulations):

1. A Burst Release Layer B) or Multiple Units:

| Ingredient | | % w/w |
|---|---|---|
| Homopolymer (e.g. PEO) | 20,000-100,000 daltons | 5-70 |
| Co-polymer (e.g. Poloxamer) | 1,000-16,000 daltons | 5-70 |
| Active substance | | 0.1-80 |
| Filler | | Up to 100% |

2. A Controlled Release Layer B) or Multiple Units:

| Ingredient | | % w/w |
|---|---|---|
| Homopolymer (e.g. PEO) | 100,000-700,000 daltons | 5-70 |
| Co-polymer (e.g. Poloxamer) | 1,000-30,000 daltons | 5-70 |
| Active substance | | 0.1-80 |
| Filler | | Up to 100% |

3. A Burst Release Inner Layer A):

| Ingredient | | % w/w |
|---|---|---|
| Homopolymer (e.g. PEO) | 1,000-16,000 daltons | 5-70 |
| Co-polymer (e.g. Poloxamer) | 2,000-30,000 daltons | 5-70 |
| Swelling agent | | 5-80% |
| Active substance | | 0.1-80 |
| Filler | | Up to 100% |

4. A Burst Release Inner Layer A):

| Ingredient | | % w/w |
|---|---|---|
| Homopolymer (e.g. PEO) | 1,000-16,000 daltons | 5-70 |
| Co-polymer (e.g. Poloxamer) | 2,000-30,000 daltons | 5-70 |
| Effervescent agent | | 5-80% |
| Active substance | | 0.1-80 |
| Filler | | Up to 100% |

5. A Burst Release Layer B):

| Ingredient | % w/w |
|---|---|
| PEO 100 000 | 5 |
| Poloxamer 188 | 5 |
| Maltitol | 15 |
| Active substance | 75 |

6. A Controlled Release Layer B):

| Ingredient | % w/w |
|---|---|
| PEO 200 000 | 25 |
| Poloxamer 338 | 25 |
| Xylitol | 10 |
| Active substance | 40 |

7. A Controlled Release Layer B):

| Ingredient | % w/w |
|---|---|
| PEO 500 000 | 20 |
| Poloxamer 407 | 50 |
| Mannitol | 2 |
| Active substance | 28 |

8. A Controlled Release Layer B):

| Ingredient | % w/w |
|---|---|
| PEO 700 000 | 20 |
| Poloxamer 407 | 50 |
| Sorbitol | 2 |
| Active substance | 28 |

9. A Controlled Release Layer B):

| Ingredient | % w/w |
|---|---|
| PEO 100 000 | 52 |
| PoloXamer188 | 10 |

-continued

| Ingredient | % w/w |
|---|---|
| Eudragit RL | 10 |
| Active substance | 28 |

10. A Burst Release Inner Layer A):

| Ingredient | % w/w |
|---|---|
| Croscarmellose | 20 |
| Lactose | 20 |
| PEO 100 000 | 5 |
| Poloxamer 188 | 5 |
| Active substance | 50 |

11. A Burst Release Inner Layer A):

| Ingredient | % w/w |
|---|---|
| Starch | 20 |
| Lactose | 20 |
| PEG 1500 | 5 |
| Poloxamer 188 | 5 |
| Active substance | 50 |

12. A Burst Release Inner Layer A):

| Ingredient | % w/w |
|---|---|
| PEO 100 000 | 5 |
| Poloxamer 188 | 5 |
| Citric Acid | 10 |
| $NaHCO_3$ | 10 |
| Active substance | 70 |

13. A Burst Release Inner Layer A):

| Ingredient | % w/w |
|---|---|
| PEO 100 000 | 5 |
| Poloxamer 188 | 5 |
| Povidone | 2 |
| Citric Acid | 10 |
| $NaHCO_3$ | 10 |
| Active substance | 68 |

14. A Burst Release Inner Layer A):

| Ingredient | % w/w |
|---|---|
| PEO 100 000 | 5 |
| Poloxamer 188 | 5 |
| Povidone | 2 |
| Citric Acid | 10 |
| $NaHCO_3$ | 10 |
| Active substance | 68 |

15. Burst Release Multiple Units:

| Ingredient | % w/w |
|---|---|
| PEO 100 000 | 5 |
| Poloxamer 188 | 5 |

-continued

| Ingredient | % w/w |
| --- | --- |
| Povidone | 20 |
| Active substance | 70 |

16. Controlled Release Multiple Units:

| Ingredient | % w/w |
| --- | --- |
| PEO 100 000 | 5 |
| Poloxamer 407 | 15 |
| Ethylcellulose | 70 |
| Active substance | 10 |

17. Controlled Release Multiple Units Coated with Eudragit RL 30D/RS 30D:

| Ingredient | % w/w |
| --- | --- |
| PEO 100 000 | 5 |
| Poloxamer 188 | 5 |
| Povidone | 20 |
| Active substance | 70 |

18. Coat with a Solid Content of 20%

| Ingredient | % w/w |
| --- | --- |
| Eudragit RL 30D | 3.9 |
| Eudragit RS 30D | 35.3 |
| Talc | 5.9 |
| Triethyl citrate | 2.33 |
| Water | 52.5 |

In the appended FIGS. 15-24 are given release profiles obtainable by compositions of the present invention.

Other specific embodiments are listed in the following:
1. A layered pharmaceutical composition comprising A) a solid inner layer comprising
i) a substantially water soluble and/or crystalline polymer or a mixture of substantially water soluble and/or crystalline polymers, the polymer being a polyglycol in the from of one of a) a homopolymer having a MW of at the most about 16,000 daltons, and b) a copolymer having a MW of at the most about 30,000 daltons, and
ii) an active substance,
the solid inner core being sandwiched between two outer layers B1 and B2), each outer layer comprising
iii) a substantially water soluble and/or crystalline polymer or a mixture of substantially water soluble and/or crystalline polymers, the polymer being a polyglycol in the from of one of c) a homopolymer having a MW of at least about 100,000 daltons, and d) a copolymer having a MW of at least about 2,000 daltons,
and i) of layer A being different from iii) of layer B,
the layered composition being coated with a coating C) that has at least one opening exposing at least one surface of said outer layer, the coating being substantially insoluble in and impermeable to fluids and comprising a polymer.
2. A composition according to item 1, wherein A) further comprises one or more disintegration/exploding agents, one of more effervescent agents or a mixture thereof
3. A composition according to item 2, wherein the disintegrant/exploding is Sodium starch glycolate, Povidone, Sodium alginate, Alginic acid, Calcium alginate, Carboxymethylcellulose calcium, Carboxymethylcellulose sodium, Powdered cellulose, Chitosan, Croscarmellose sodium, Crospovidone, Hydroxypropyl starch, Hydroxypropyl cellulose low-substituted, Magnesium aluminium silicate, Methylcellulose, Microcrystalline cellulose, pregelatinized starch, Docusae sodium, Guar gum, Polacrilin potassium or the like.
4. A composition according to item 2, wherein the effervescent agent is Effer-Soda, Citric acid, Citric acid, monohydrate, Dextrates, Fumaric acid, Potassium bicarbonate, Sodium bicarbonate, Sodium citrate dehydrate, Tartaric acid or the like.
5. A composition according to any of the preceding items, wherein the outer layer B1 and/or B2 when exposed to an aqueous medium erodes at a substantially constant rate.
6. A composition according to any of the preceding items, wherein the active substance in A) is subject to release after a lag time corresponding to the erosion time of the layer B1 and/or B2.
7. A composition according to any of the preceding items, wherein the inner layer A) without B) and C) disintegrates within at the most 60 min such as, e.g., at the most about 30 min or at the most about 15 min, when subjected to a disintegration test according to Ph. Eur.
8. A composition according to any of the preceding items having a cylindrical shape optionally with one or more tapered ends.
9. A composition according to any of the preceding items, wherein the coating C) appears as a substantially intact empty shell when the composition has been subjected to a dissolution test according to Ph. Eur. by which the outer layer B) erodes and the inner layer A) disappears from the composition optionally by means of one or more disintegration agents, explosion agents, effervescent agents or a mixture thereof.
10. A composition according to any of the preceding items, wherein the polymers i) and iii), and the polymer contained in the coating C) are thermoplastic.

Inner Layer
11. A composition according to any of the preceding items, wherein polymer i) comprises a homopolymer having a MW of at least about 1,000 daltons such as, e.g., a homopolymer having a MW in a range from about 1,000 to about 15,000 daltons, from about 1,000 to about 12,000 daltons, from about 1,500 to about 10,000 daltons, from about 1,500 to about 8,000 daltons.
12. A composition according to any of the preceding items, wherein polymer i) comprises a copolymer having a MW of at the most about 25,000 daltons such as, e.g., at the most about 20,000 daltons, at the most about 15,000 daltons, at the most about 10,000 daltons, at the most about 5,000 daltons, at the most about 2,000 daltons.
13. A composition according to any of the preceding items, wherein the active substance in A) is present at least partly in solid or dissolved form.
14. A composition according to any of the preceding items, wherein the active substance in A) is present in form of pellets, beads, flakes, mini-tablets, granules, microspheres, nanoparticle, crystals or the like.
15. A composition according to claim 14, wherein the active substance containing pellets, beads, flakes, mini-tablets, granules, microspheres, nanoparticles, crystal or the like are dispersed in the polymer i).
16. A composition according to any of the preceding items, wherein the concentration of the polymer i) in inner layer A) is from about 5% w/w to about 100% w/w.

17. A composition according to any of the preceding items 2-16, wherein the concentration of the one or more disintegration/exploding agent, if present, is from about 5% w/w to about 80% w/w such as, e.g., from about 10% w/w to about 70% w/w, from about 15% w/w to about 60% w/w or from about 20% w/w to about 50% w/w.
18. A composition according to any of the preceding items, wherein the concentration of the one or more effervescent agent, if present, is from about 5% w/w to about 80% w/w such as, e.g., from about 10% w/w to about 70% w/w, from about 15% w/w to about 60% w/w or from about 20% w/w to about 50% w/w.

Outer Layer

19. A composition according to any of the preceding items, wherein polymer iii) comprises one or more of a polyethylene glycol, a polyethylene oxide and/or a copolymer of ethylene oxide and propylene oxide including poly(ethylene-glycol-b-(DL-lactic acid-co-glycolic acid)-b-ethylene glycol (PEG-PLGA PEG), poly((DL-lactic acid-co-glycolic acid)-g-ethylene glycol) (PLGA-g-PEG), and polyethylene oxide-polypropylene oxide (PEO-PPO).
20. A composition according to item 19, wherein the polyethylene glycol or a polyethylene oxide has a molecular weight from about 100,000 to about 700,000.
21. A composition according to item 19, wherein the copolymer of ethylene oxide and propylene oxide comprises up to about 30% w/w of the propylene oxide based block, and has a molecular weight of from about 5,000 to about 15,000 daltons.
22. A composition according to any of the preceding items, wherein the concentration of polymer iii) in layer B) is from about 5% w/w to about 100% w/w.
23. A composition according to any of the preceding items, wherein layer B1) and/or B2) contain a second active substance.
24. A composition according to item 23, wherein the release of the second active substance follows a zero order release pattern at least up to 80% w/w release of the total content of second active substance in layer B).

Coating

25. A composition according to any of the preceding items, wherein the polymer comprised in the coating is selected from the group consisting of ethylcellulose, cellulose acetate, cellulose propionate, cellulose nitrate, polyamide, polyethylene, polyethylene terephtalate, polypropylene, polyurethane, polyvinyl acetate, polyvinyl chloride, silicone rubber, latex, polyhydroxybutyrate, polyhydroxyvalerate, teflon, polylactic acid or polyglycolic acid and copolymers thereof, copolymers including ethylene vinyl acetate, styrene-butadienstyrene and styrene-isoprene-styrene.
26. A composition according to any of the preceding items, wherein the coating does not completely crumble or erode before the layer B) has completely eroded and the layer A) is released.

The invention is further illustrated in the following non-limiting examples.

EXAMPLES

Dissolution Method for Testing Dosage Units According to the Invention

Dissolution testing is performed according to USP 30, NF 25 (711), and apparatus 2 (paddle method). The dissolution medium may consist of 0.1 M HCl or phosphate buffer e.g. pH 6.8, pH 6.8 & 40% ethanol or pH 7.2. The volume of dissolution medium is typically 900 ml or 1000 ml and the paddle speed is 50 rpm. Samples are withdrawn at suitable time points and analysed for content of active substance by means of on-line UV detection or HPLC with UV detection.

Methods

A general method for preparation dosage unit is described below.

Preparation of a Matrix Composition

An accurate amount of the polymer is loaded into a MTI mixer followed by an accurate amount of the active substance and of the pharmaceutically acceptable excipients(s), if any. The mixing is performed at 900-2000 rpm and at a time period up to 20 min. At the start of the mixing the temperature is about 19-21° C. and the final temperature of the mixture is about 30-50° C. The mixture is then allowed to cool to room temperature and is ready to be fed into an injection moulding machine.

Preparation of the Coating Composition

The coating composition is prepared by first adding the Ethylcellulose then Cetostearyl alcohol, and finally the Titanium dioxide to an MTI-Mixer at a temperature about 19-21° C. Mixing rate is 1000 rpm. The mixer is stopped when the temperature reaches 40-50° C. and the adhered material is manually incorporated into the mixture. The mixture is left to cool for about 10 minutes. The mixing is then finalized with a short high-speed mix in order to minimize lumps formation. The mixture is then allowed to cool to room temperature, after which it has a suitable consistency for being fed into an injection moulding machine.

Example of a Coat Composition;

| Material | Batch: 58-014-01-013 %(w/w) | Batch: 08-0017-058 %(w/w) |
|---|---|---|
| Ethylcellulose | 79 | 86.5 |
| Cetostearyl alcohol | 20 | 12.5 |
| Titanium dioxide | 1 | 1 |

Small Scale Preparation

A mixture may be prepared by simple volumetric mixing of the components. 3 g of the mixture is then feeded into a table top injection molding machine (Haake MiniJet II, Thermo Electron, Karlsruhe, Germany) and molded directly into a pre-molden shell and/or matrix. Typical settings in the MiniJet are: Temperature 90-120° C. and pressure 600-800 bar.

Preparation of Dosage Unit

The final dosage units may be prepared according to two different methods. In one method, the coat and the matrix are moulded individually followed by a manually incorporation of the moulded matrix plug into the moulded coat. The injection moulding machine used is an Arburg Allrounder 220 S 250/60. In the second method, the coat and matrix are moulded in one process where the coat is moulded in a first step and the matrix is moulded directly into the coat in a second step (co-moulding or 2-component moulding). The injection moulding machine used is Arburg Allrounder 420 V 800-60/35.

Preparation 1

Pellets for the Inner Layer A of a Dosage Unit According to the Invention (PHH 0120-063)

Pellets were prepared by mixing Poloxamer 188 (48% w/w), Eudragit RL (24% w/w) and Hydrocortisone (28% w/w) in a beaker on a heat stage set at 150° C. The melt was applied to a punched plate (hole size 1 mm) and pellets of diameter 1 mm was formed. The pellets disintegrated in cold MQ water in less than 1 h.

Preparation 2

An Inner Layer a for a Dosage Unit According to the Invention Prepared by Direct Compression (PHH-0120-061-2)

Pellets (batch 108-009-05-001C) comprising Hydrocortison (55% w/w), PEG 8000 (40% w/w) and PVP C15 (5% w/w) was prepared by hot melt extrusion followed by grinding. The pellets were sieved to reach a final size of 1000 μm-1200 μm. 35-37 mg pellets were mixed with 206-230 mg filler material comprising Lactose (StarLac®). The material was placed in an IR-tablet preparing device and compressed at a pressure of 5 metric tons.

Dissolution shows that the tablet is completely disintegrated after 18 minutes leaving the pellets for slower dissolution. Upon testing with an USP 2 apparatus using 900 ml phosphate buffered media, pH 6.8 and 50 RPM the following release profile was obtained.

| Time (min) | Release (%) |
|---|---|
| 50 min | 50 |
| 245 min | 80 |
| 490 min | 90 |

Preparation 3

An Inner Layer A for a Dosage Unit According to the Invention Prepared by Direct Compression (PHH-0120-062-4)

Pellets (batch 108-009-05-001C) comprising Hydrocortison (55% w/w), PEG 8000 (40% w/w) and PVP C15 (5% w/w) was prepared by hot melt extrusion followed by grinding. The pellets were sieved to reach a final size of 1000 μm-1200 μm. 35-37 mg pellets were mixed with 165-336 mg filler material comprising Lactose (StarLac®):NaHCO$_3$:Citric Acid (1497:333:272% w/w). The material was placed in an IR-tablet preparing device and compressed at a pressure of 5 metric tons.

Dissolution shows that the tablet disintegrates immediately leaving the pellets for slower dissolution. Upon testing with an USP 2 apparatus using 900 ml phosphate buffered media, pH 6.8 and 50 RPM the following release profile was obtained.

| Time (min) | Release (%) |
|---|---|
| 40 min | 50 |
| 185 min | 80 |
| 435 min | 90 |

Preparation 4

Figure 2:
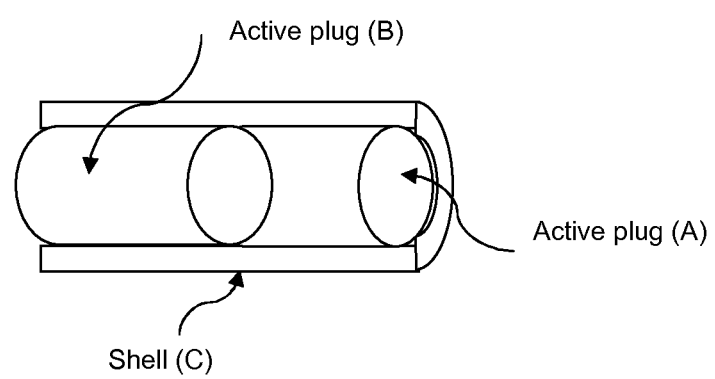
FIG. 2, illustrate simple combination formulation.

A dosage unit exhibiting Burst-controlled behaviour (MQV batch 1047-041, 1047-042 & 1047-044), see FIG. 2. As both Morphine and Hydrocodone absorb at the same wave length, it has been necessary to conduct two parallel experiments—each experiment applying a dosage unit with active substance combined with placebo. The dosage units consisted of two plugs, one containing the active substance, one being a placebo-formulation. Finally the results from the two experiments were pooled, thereby simulating one dosage unit consisting of the two active substances, one plug which exhibits burst release of Hydrocodone and the other controlled release of Morphine.

The shell was produced by injection moulding. The plugs were injection moulded using the mini jet at applying a temperature 110° C., a pressure of 800 bar and a cycle time of 20 s. The thickness and the diameter of the plug was 4.5 mm diameter. The exposed area of the matrix (i.e. two ends) is 35.04 mm$^2$ and the length of the dosage unit is 9 mm.

Preparation of a Controlled Release Plug:

The active plug comprised: PoloXamer 188, PEO 300 000, Morphine Sulphate pentahydrate and Mannitol, which were mixed. Afterwards the powder mixture fed to the injection moulding machine.

The inactive (placebo) plug comprised: PoloXamer 407, PEO 300 000, which were mixed. Then the powder mixture was fed to the injection moulding machine.

Preparation of a Burst Release Plug:

The active plug comprised: Hydrocodone bitartarte, PEG 3350S, Sodium hydrogen carbonate and Citric acid, which were mixed. Afterwards the powder mixture fed to the injection moulding machine.

The inactive (placebo) plug comprised: PEG 3350S, Sodium hydrogen carbonate and Citric acid, which were mixed. Then the powder mixture was fed to the injection moulding machine.

The Controlled Release Plug has the Composition:

| | Content % (w/w) |
|---|---|
| Active plug | |
| Morphine sulphate pentahydrate | 53 |
| Mannitol | 3 |
| PEO 300 000 | 35 |
| PoloXamer 188 | 9 |
| Inactive (placebo) plug | |
| PEO 300 000 | 85 |
| PoloXamer 407 | 15 |

The Burst Release Plug has the Composition:

| | Content % (w/w) |
|---|---|
| Active plug | |
| Hydrocodone bitartrate | 53 |
| PEG 3350S | 41 |
| Sodium hydrogen carbonate | 3 |
| Citric acid | 3 |
| Inactive (placebo) plug | |
| PEG 3350S | 94 |
| Sodium hydrogen carbonate | 3 |
| Citric acid | 3 |
| Shell | |
| Ethylcellulose | 86.5 |
| Cetostearyl alcohol | 12.5 |
| Titanium dioxide | 1.0 |

Figure 3:
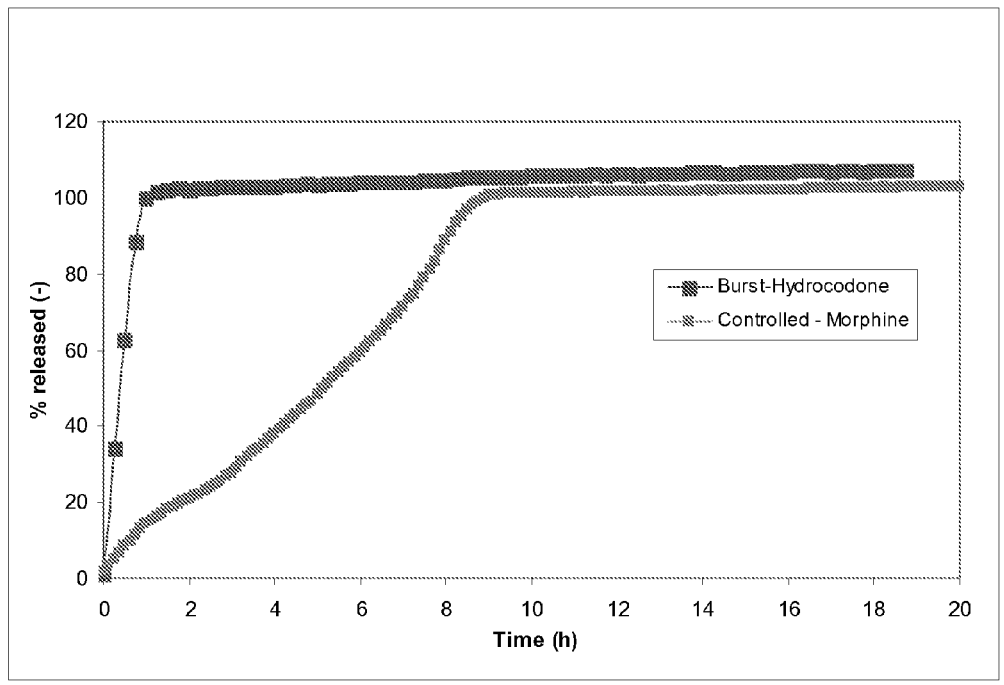
FIG. 3, releases of Hydrocodone and Morphine with burst-controlled release behaviour see preparation 4.

The dissolution behaviour as tested by USP 2 apparatus, (pH 6.8, 900 ml phosphate buffered media, 50 RPM), see FIG. 3.

Preparation 5

A dosage unit exhibiting Controlled-controlled behaviour (MQV batch 1047-041), see FIG. 2. As both active substances Morphine and Oxycodone absorb at the same wave length, it has been necessary to conduct two parallel experiments—each experiment applying a dosage unit with active substance combined with placebo. The dosage units consisted of two plugs, one containing the active substances, one being a placebo-formulation. Finally the results from the two experiments were pooled, thereby simulating one dosage unit consisting of Morphine and Oxycodone, both exhibiting controlled release beheveour.

The shell was produced by injection moulding. The plugs were injection moulded using the mini jet at applying a temperature 110° C., a pressure of 800 bar and a cycle time of 20 s. The thickness and the diameter of the plug was 4.5 mm diameter. The exposed area of the matrix (i.e. two ends) is 35.04 mm$^2$ and the length of the dosage unit is 9 mm.

Preparation of Plug (for Controlled Release of Morphine):

The active plug comprised: PoloXamer 188, PEO 300 000, Morphine Sulphate pentahydrate and Mannitol, which were mixed. Afterwards the powder mixture fed to the injection moulding machine.

Preparation of Plug (for Controlled Release of Oxycodone):

The active plug comprised: Oxycodone hydrochloride, PEO 200 000, Mannitol, PoloXamer 407, which were mixed. Afterwards the powder mixture fed to the injection moulding machine.

In both cases the inactive (placebo) plug comprised: PoloXamer 407, PEO 300 000, which were mixed. Then the powder mixture was fed to the injection moulding machine.

The dosage form (controlled release) consists of an active plug and a placebo plug, the composition is given below:

|  | Content % (w/w) |
| --- | --- |
| Active plug | |
| Morphine sulphate pentahydrate | 53 |
| Mannitol | 3 |
| PEO 300 000 | 35 |
| PoloXamer 188 | 9 |
| Active plug | |
| Oxycodone hydrochloride | 53 |
| Mannitol | 5 |
| PEO 200 000 | 17 |
| PoloXamer 407 | 25 |
| Placebo plug | |
| PEO 300 000 | 85 |
| PoloXamer 407 | 15 |
| Shell | |
| Ethylcellulose | 86.5 |
| Cetostearyl alcohol | 12.5 |
| Titanium dioxide | 1.0 |

Figure 4:
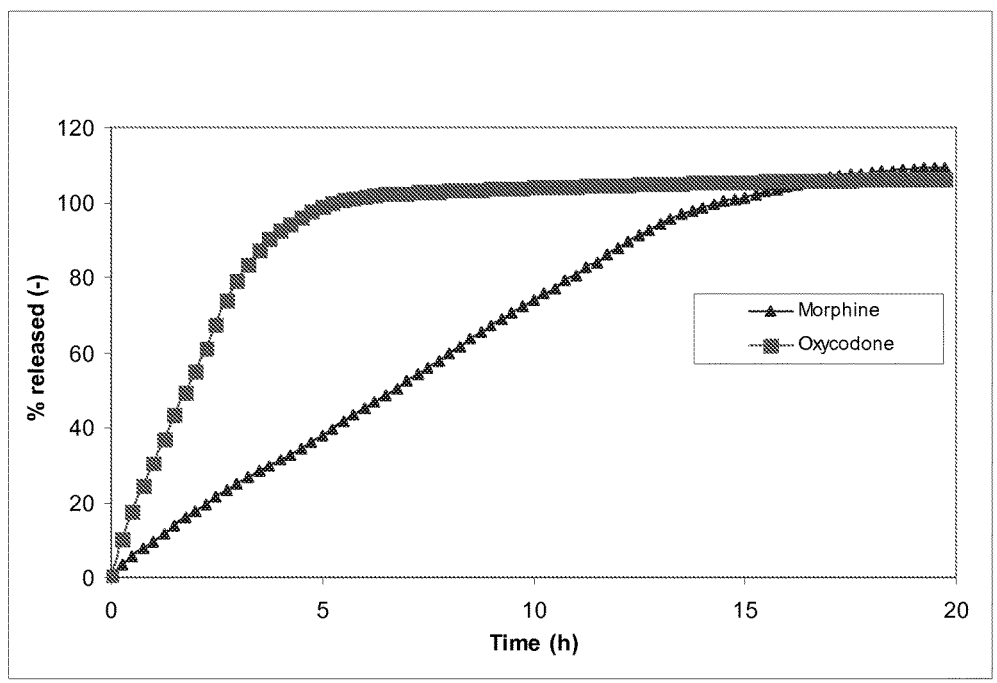
FIG. 4, releases of Oxycodone and Morphine with controlled-controlled release behaviour see preparation 5.

The dissolution behaviour as tested by USP 2 apparatus, (pH 6.8, 900 ml phosphate buffered media, 50 RPM), see FIG. 4.

Example 1

Dissolution of Non-compressed Inner Layer A for a Dosage Unit According to the Invention (PHH-0120-067).

Units were prepared by the following procedure: Pellets comprising Hydrocortison (55% w/w), PEG 8000 (40% w/w) and PVP C15 (5% w/w) was prepared by hot melt extrusion followed by grinding. The pellets were sieved to reach a uniform size. 36-38 mg pellets were mixed with 170-175 mg filler material comprising lactose (StarLac®), NaHCO$_3$ and Citric Acid (18500:825:675% w/w). Shell comprising Ethyl cellulose (89% w/w), Cetostearyl alcohol (10% w/w) and Titanium dioxide (1% w/w) (batch 06-0010-058) was prepared by injection moulding. The dosage unit was hand assembled first with a 2 mm thick delay plug comprising PEO 200 000, the pellet/filler blend was added and then another 2 mm thick delay plug comprising PEO 200 000. The exposed area of the matrix is 77 mm$^2$ and the length of the shell is 22.7 mm.

Dissolution analysis using USP 2 apparatus, pH 6.8, 900 ml phosphate buffered media at 50 RPM showed a delay for more than 4 hours followed by the immediate release of the un-dissolved pellets from the unit into the dissolution media. From the pellets 50% release of Hydrocortison was reached within 4 h from time of onset (end of delay).

Example 2

Figure 5:
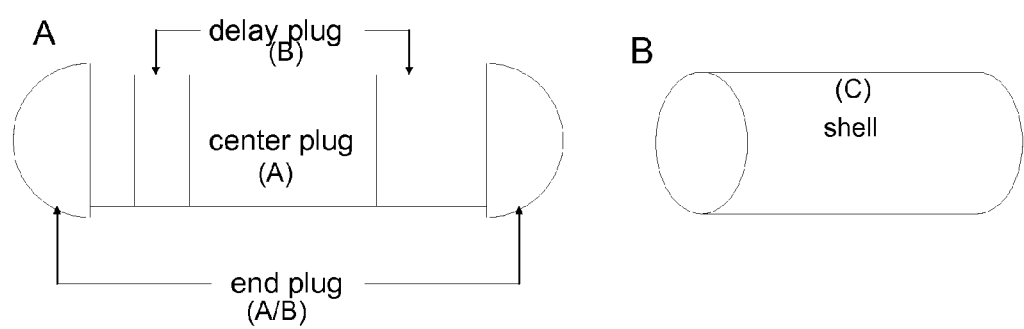
FIG. 5, illustrate double burst unit, with a delay between the two bursts.

Dosage Unit According to the Invention Exhibiting Double Burst Behaviours (Batch 05-0126-110/05-0134-110), See FIG. 5.

Shell, end plugs (layer B), delay plugs and centre plug (inner layer A) were prepared by injection moulding and hand assembled. The procedure was as follows:
1 Locate the shell with injection side upward
2 Place the first delay plug with the injection side down word at the top of the shell
3 Gently push the delay plug a few mm into the shell
4 Place the inner plug at the delay plug and push it into the shell also moving the delay plug
5 Place the second delay plug with the injection side upward at the inner plug and push it into the shell
6 One end plug is placed at each end of the shell The Dosage Form has the Composition:

|  | Content % (w/w) |
| --- | --- |
| End plug | |
| Paracetamol | 80 |
| Peg 8000 | 10 |
| Hard fat | 4 |
| Sodium bicarbonate | 3.3 |
| Citric acid, monohydrate | 2.7 |
| Delay plug | |
| PEO 200 000 | 99.5 |
| BHT | 0.5 |
| Centre plug | |
| Paracetamol | 75.2 |
| Peg 8000 | 9.4 |
| Hard fat | 3.8 |
| Sodium bicarbonate | 9.1 |
| Citric acid, monohydrate | 2.5 |
| Shell | |
| Ethylcellulose | 79 |
| Cetostearoyl | 20 |
| Titanium dioxide | 1 |

The exposed area of the matrix is 77 mm$^2$ (i.e. sum of surface area of the two ends) and the length of the shell is 22.7 mm.

Figure 6:
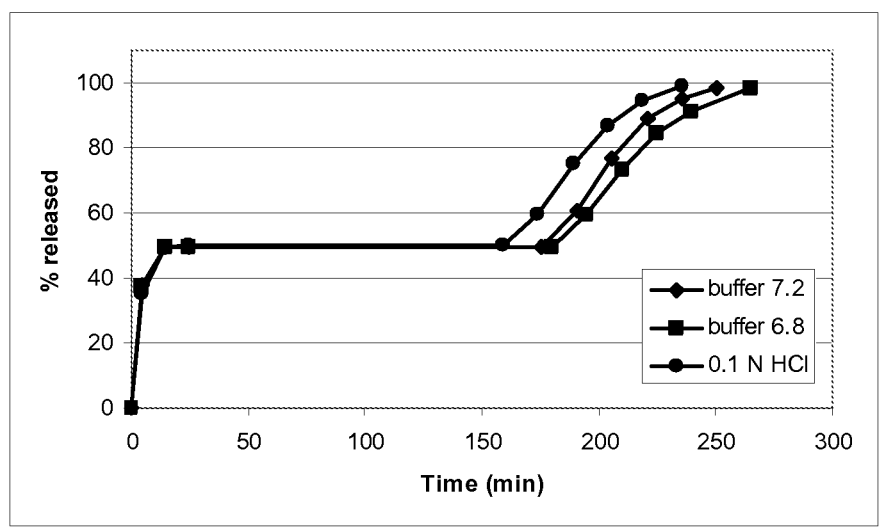
FIG. 6, release of Paracetamol with double burst release behaviour see example 2.

The dissolution behaviour as tested by USP 2 apparatus, (pH 6.8, 1000 ml phosphate buffered media, 50 RPM) was as follows (see FIG. 6):

| Time (min) | Release (%) |
| --- | --- |
| 15 | 49 |
| 155 | 50 |
| 211 | 70 |
| 218 | 75 |

| Time (min) | Release (%) |
| --- | --- |
| 241 | 92 |
| 250 | 94 |

Example 3

Figure 7:
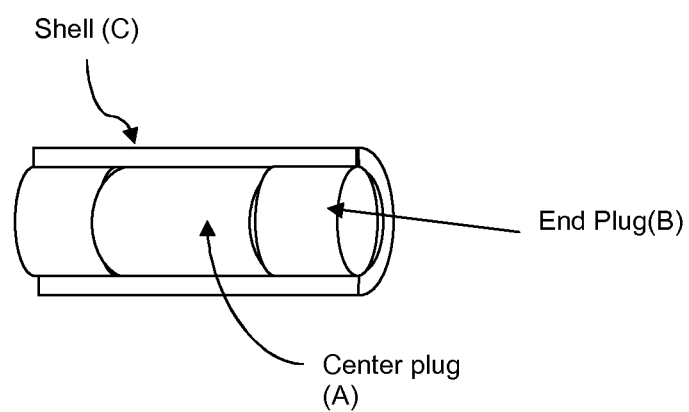
FIG. 7, illustrate unit exhibiting controlled-burst or burst-burst release behaviour.

A Dosage Unit According to the Invention Exhibiting Controlled-burst Behaviour (MQV Batch 1047-040), See FIG. 7.

The shell was produced by injection moulding. The injection moulding machine used is a Haake Minijet II. End plugs and centre plug were prepared by hand and hand assembled. Each plug had a thickness of 3 mm.

Preparation of End Plugs (for Controlled Release):

PoloXamer 338, PEO 200 000, Morphine Sulphate pentahydrate and Mannitol were mixed. Afterwards the powder mixture was heated to approximately 110° C. The melt was moulded into a 3 mm thick, and a 4.5 mm diameter, hole metal filter to attain the plugs.

Preparation of Centre Plug (for Burst Release):

Explotab, Sodium Starch Glycolate & Sodium Carboxymethyl Starch, Maize starch and Morphine Sulphate pentahydrate were mixed. Then the powder mixture was compressed to a plug (tablet) by direct compression. Centre plugs of 3 mm thickness and a diameter of 4.5 mm were prepared.

The Procedure was as Follows:

1 Locate the shell with injection side upward
2 Place the first end plug with the injection side down word at the top of the shell
3 Gently push the centre plug into the shell
4 The last end plug is placed at the end of the shell The Dosage Form has the Composition:

| | Content % (w/w) |
| --- | --- |
| End plug | |
| Morphine sulphate pentahydrate | 16 |
| Mannitol | 10 |
| PEO 200 000 | 34 |
| PoloXamer 338 | 40 |
| Centre plug | |
| Morphine sulphate pentahydrate | 32 |
| Explotab | 50 |
| Maize starch | 18 |
| Shell | |
| Ethylcellulose | 86.5 |
| Cetostearyl alcohol | 12.5 |
| Titanium dioxide | 1.0 |

The exposed area of the matrix is 34.72 mm² (i.e. two ends) and the length of the dosage unit is 9 mm.

Figure 8:
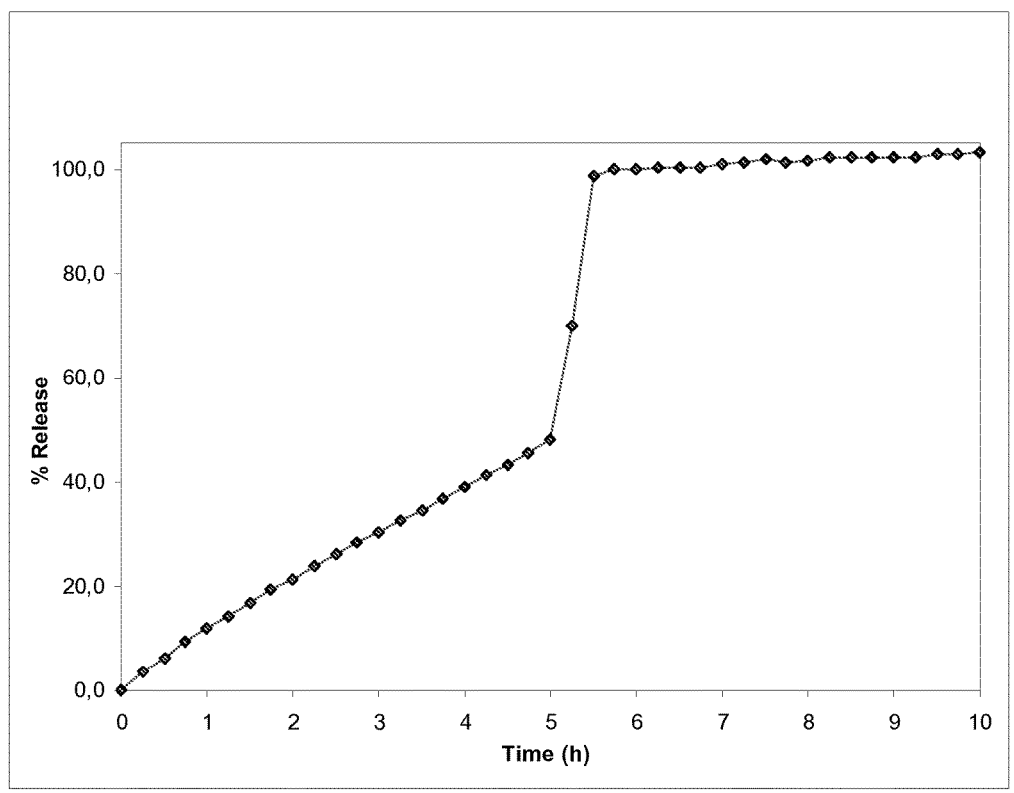
FIG. 8, release of Morphine with controlled-burst release behaviour see example 3.

The dissolution behaviour as tested by USP 2 apparatus, (pH 6.8, 900 ml phosphate buffered media, 50 RPM), see FIG. 8.

Example 4

A Dosage Unit According to the Invention Exhibiting Controlled-burst Behaviour (MQV Batch 1047-045), See FIG. 7.

The shell was produced by injection moulding. The injection moulding machine used is a Haake Minijet II. End plugs and centre plug were prepared by hand and hand assembled. Each plug had a thickness of 3 mm.

Preparation of End Plugs (for Controlled Release):

PoloXamer 338, PEO 200 000, Morphine Sulphate pentahydrate and Mannitol were mixed. Afterwards the powder mixture was heated to approximately 110° C. The melt was moulded into a 3 mm thick, and a 4.5 mm diameter, hole metal filter to attain the plugs.

Preparation of Centre Plug (for Burst Release):

Sodium hydrogen carbonate, Citric acid and Morphine Sulphate pentahydrate were mixed. Then the powder mixture was compressed to a plug (tablet) by direct compression. Centre plugs of 3 mm thickness and a diameter of 4.5 mm were prepared.

The Procedure was as Follows:

1 Locate the shell with injection side upward
2 Place the first end plug with the injection side down word at the top of the shell
3 Gently push the centre plug into the shell
4 The last end plug is placed at the end of the shell The Dosage Form has the Composition:

| | Content % (w/w) |
| --- | --- |
| End plug | |
| Morphine sulphate pentahydrate | 16 |
| Mannitol | 10 |
| PEO 200 000 | 34 |
| PoloXamer 338 | 40 |
| Centre plug | |
| Morphine sulphate pentahydrate | 32 |
| Citric acid | 34 |
| Sodium hydrogen carbonate | 34 |
| Shell | |
| Ethylcellulose | 86.5 |
| Cetostearyl alcohol | 12.5 |
| Titanium dioxide | 1.0 |

The exposed area of the matrix (i.e. two ends) is 34.72 mm² and the length of the dosage unit is 9 mm.

Figure 9:
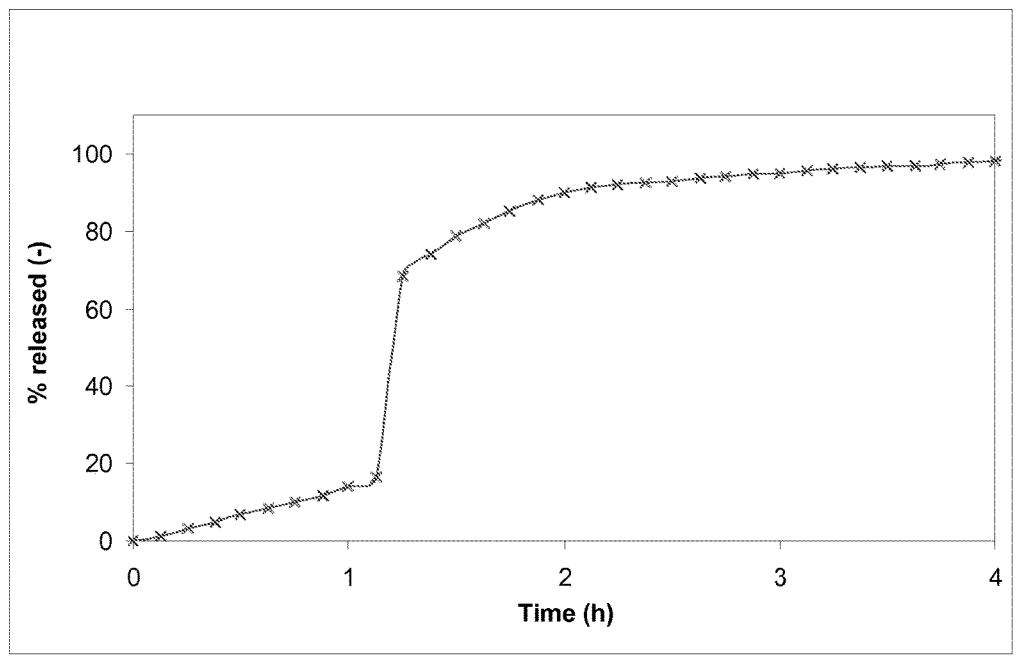
FIG. 9, release of Morphine with controlled-burst release behaviour see example 4.

The dissolution behaviour as tested by USP 2 apparatus, (pH 6.8, 900 ml phosphate buffered media, 50 RPM), see FIG. 9.

Example 5

Figure 10:
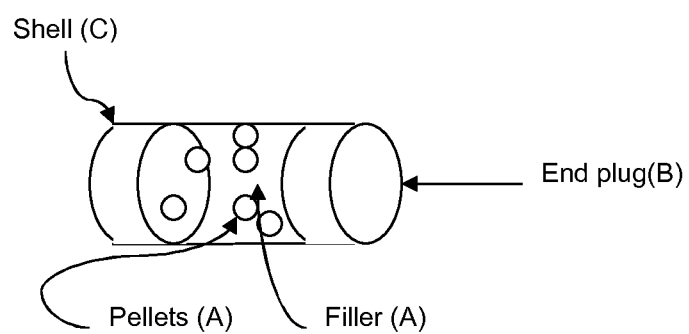
FIG. 10, illustrate unit exhibiting controlled-controlled or burst-controlled release behaviour.

A Dosage Unit According to the Invention Exhibiting Controlled-controlled Behaviour (MQV Batch 1047-043), See FIG. 10.

The shell was produced by injection moulding. End plugs and centre plug, comprising pellets, were prepared by hand and hand assembled. Each plug had a thickness of 3 mm.

Preparation of End Plugs (for Controlled Release):

PoloXamer 188, PEO 300 000, Mannitol and Morphine sulphate pentahydrate were mixed. The material was melted to approximately 110° C., and the melt was moulded into a 3 mm thick, and a 4.5 mm diameter, hole metal filter to attain the plugs.

Preparation of Centre Plug (for Controlled Release):

PoloXamer 188, PEO 300 000, Mannitol and Morphine sulphate pentahydrate were mixed and processed on a melt extruder. The extruded strings were cooled and cut into pellets. The pellets were sieved to reach a uniform size. Pellets were mixed with CrosPovidone to attain a centre plug of approximately 3 mm thickness and a 4.5 mm diameter.

The Procedure was as Follows:

1 Locate the shell with injection side upward
2 Place the first end plug with the injection side down word at the top of the shell
3 Pellets and CrosPovidone were added into the shell
4 The last end plug is placed at the end of the shell The Dosage Form has the Composition:

|  | Content % (w/w) |
| --- | --- |
| End plug | |
| Morphine sulphate pentahydrate | 53 |
| Mannitol | 3 |
| PEO 300 000 | 35 |
| PoloXamer 188 | 9 |
| Pellets | |
| Morphine sulphate pentahydrate | 53 |
| Mannitol | 3 |
| PEO 300 000 | 35 |
| PoloXamer 188 | 9 |
| Centre plug | |
| Pellets and 25% CrossPovidone were added | |
| Shell | |
| Ethylcellulose | 86.5 |
| Cetostearyl alcohol | 12.5 |
| Titanium dioxide | 1.0 |

The exposed area of the matrix (i.e. two ends) is 34.72 $mm^2$ and the length of the dosage unit is 9 mm.

Figure 11:
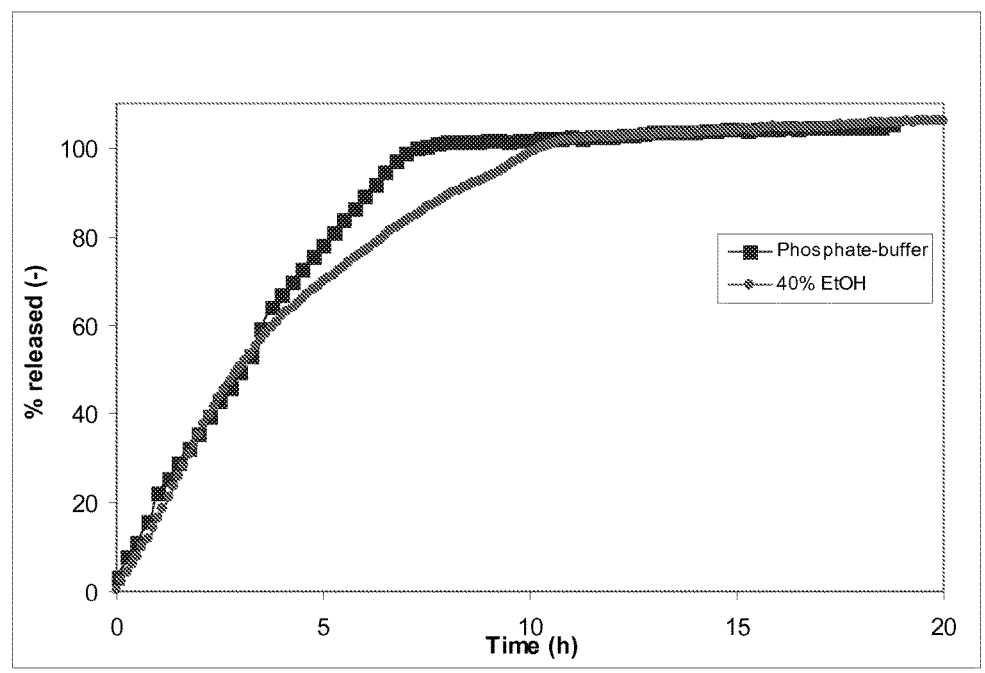
FIG. 11, release of Morphine with controlled-controlled release behaviour see example 5.
Figure 12:
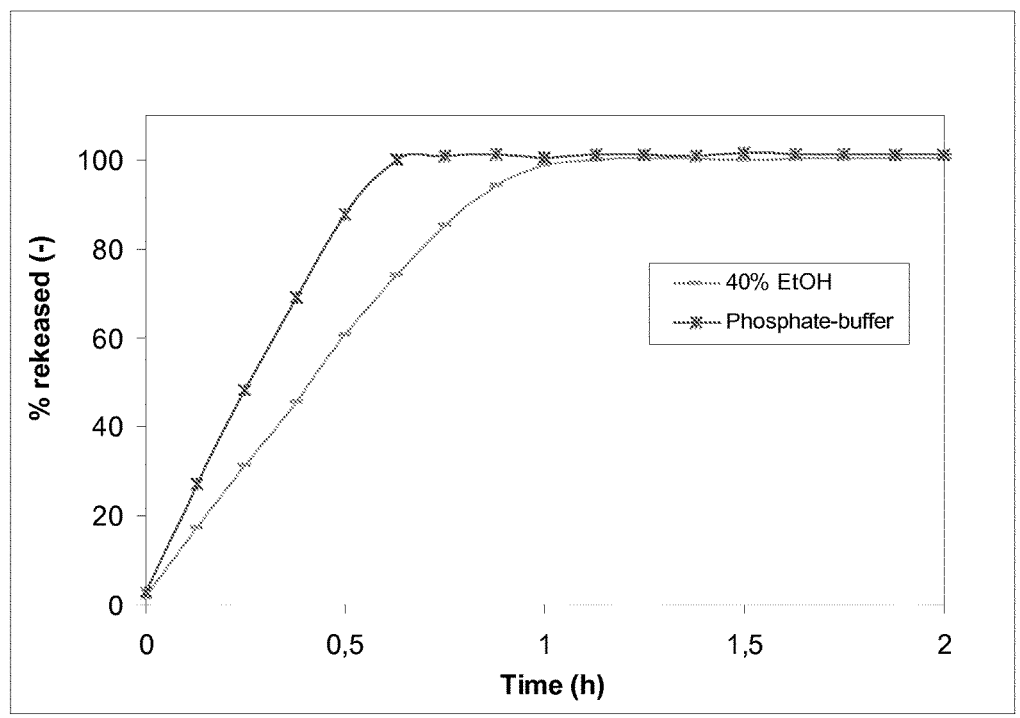
FIG. 12, release of Morphine pellets see example 5.

The dissolution behaviours as tested by USP 2 apparatus, (pH 6.8 and pH 6.8/40% ethanol, 900 ml phosphate buffered media, 50 RPM), see FIG. 11. Furthermore, it is demonstrated that these pellets are abuse resistant as the dissolution rate is significantly lower in alcohol-containing media, see FIG. 12.

Example 6

A Dosage Unit According to the Invention Exhibiting Controlled-controlled Behaviour (MQV Batch 1047-047, See FIG. 10.

The shell was produced by injection moulding. End plugs and centre plug, comprising pellets, were prepared by hand and hand assembled. Each plug had a thickness of 3 mm.

Preparation of End Plugs (for Controlled Release):

Morphine, PEO and PoloXamer 407 were mixed thoroughly and melted to approximately 110° C., and the melt was moulded into a 2 mm thick, and a 4.5 mm diameter, hole metal filter to attain the plugs.

Preparation of Centre Plug (for Controlled Release):

PoloXamer 188, PEO 300 000, Mannitol and Morphine sulphate pentahydrate were mixed and processed on a melt extruder. The extruded strings were cooled and cut into pellets. The pellets were sieved to reach a uniform size. Pellets were mixed with CrosPovidone to attain a centre plug of approximately 3 mm thickness and a 4.5 mm diameter.

The Procedure was as Follows:

1 Locate the shell with injection side upward
2 Place the first end plug with the injection side down word at the top of the shell
3 Pellets and CrosPovidone were added into the shell
4 The last end plug is placed at the end of the shell The Dosage form has the Composition:

|  | Content % (w/w) |
| --- | --- |
| End plug | |
| Morphine sulphate pentahydrate | 20 |
| PEO | 45 |
| PoloXamer 407 | 35 |
| Pellets | |
| Morphine sulphate pentahydrate | 53 |
| Mannitol | 3 |
| PEO 300 000 | 35 |
| PoloXamer 188 | 9 |
| Centre plug | |
| Pellets and 25% CrossPovidone were added | |
| Shell | |
| Ethylcellulose | 86.5 |
| Cetostearyl alcohol | 12.5 |
| Titanium dioxide | 1.0 |

The exposed area of the matrix (i.e. two ends) is 34.72 $mm^2$ and the length of the dosage unit is 9 mm.

Figure 13:
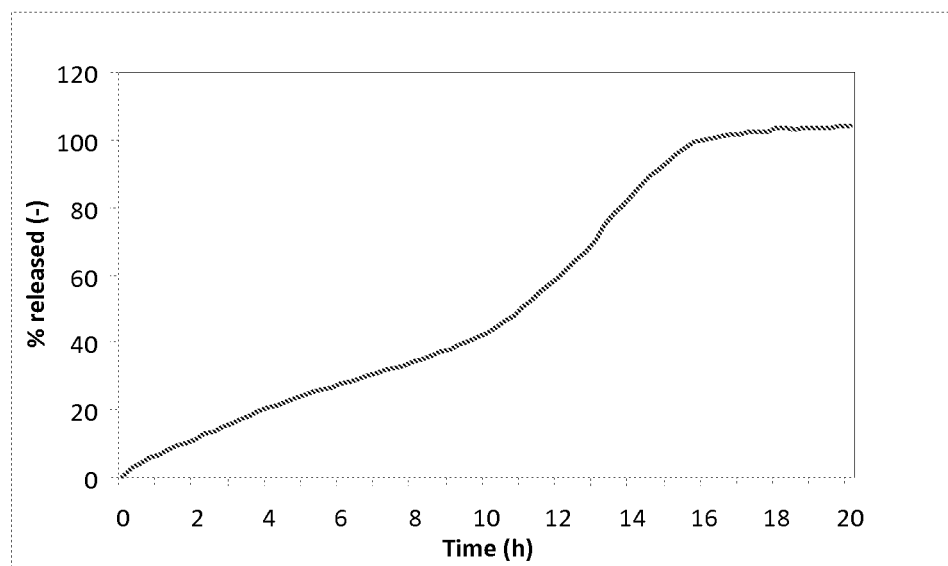
FIG. 13, release of Morphine with controlled-controlled release behaviour see example 6.

The dissolution behaviour as tested by USP 2 apparatus, (pH 6.8, 900 ml phosphate buffered media, 50 RPM, see FIG. 13.

Example 7

A Dosage Unit According to the Invention Exhibiting Burst-controlled Behaviour (MQV Batch 1047-046), See FIG. 10.

The shell was produced by injection moulding. End plugs and centre plug, comprising pellets, were prepared by hand and hand assembled. Each plug had a thickness of 3 mm.

Preparation of End Plugs (for Burst Release):

Morphine sulphate pentahydrate, PEG 3350S, Sodium hydrogen carbonate and Citric acid were mixed and melted to approximately 110° C., and the melt was moulded into a 3 mm thick, and a 4.5 mm diameter, hole metal filter to attain the plugs.

Preparation of Centre Plug (for Controlled Release):

PoloXamer 188, PEO 300 000, Mannitol and Morphine sulphate pentahydrate were mixed and processed on a melt extruder. The extruded strings were cooled and cut into pellets. The pellets were sieved to reach a uniform size. Pellets were mixed with CrosPovidone to attain a centre plug of approximately 3 mm thickness and a 4.5 mm diameter.

The Procedure was as Follows:

1 Locate the shell with injection side upward
2 Place the first end plug with the injection side down word at the top of the shell
3 Pellets and CrosPovidone were added into the shell
4 The last end plug is placed at the end of the shell The Dosage Form has the Composition:

|  | Content % (w/w) |
|---|---|
| End plugs | |
| Morphine sulphate pentahydrate | 25 |
| PEG 3350S | 65 |
| Sodium hydrogen carbonate | 5 |
| Citric acid | 5 |
| Pellets | |
| Morphine sulphate pentahydrate | 53 |
| Mannitol | 3 |
| PEO 300 000 | 35 |
| PoloXamer 188 | 9 |
| Centre plug | |
| Pellets and 25% CrossPovidone were added | |
| Shell | |
| Ethylcellulose | 86.5 |
| Cetostearyl alcohol | 12.5 |
| Titanium dioxide | 1.0 |

The exposed area of the matrix (i.e. two ends) is 34.72 mm$^2$ and the length of the dosage unit is 9 mm.

Figure 14:
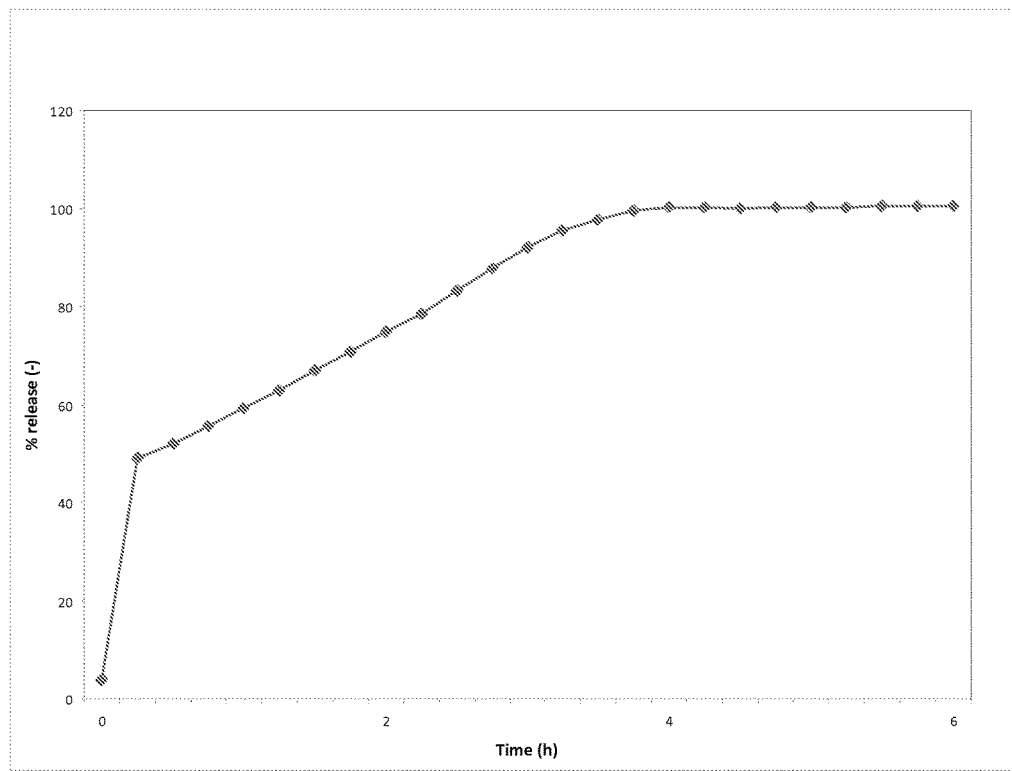
FIG. 14, release of Morphine with burst-controlled release behaviour see example 7.
Figure 15:
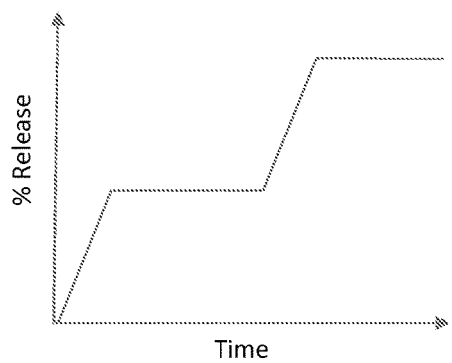
FIG. 15, illustrate burst-lag-burst release characteristics.
Figure 16:
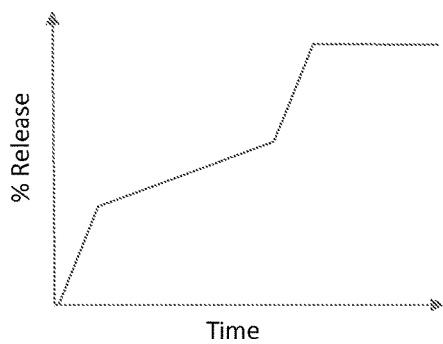
FIG. 16, illustrate burst-controlled-burst release characteristics.
Figure 17:
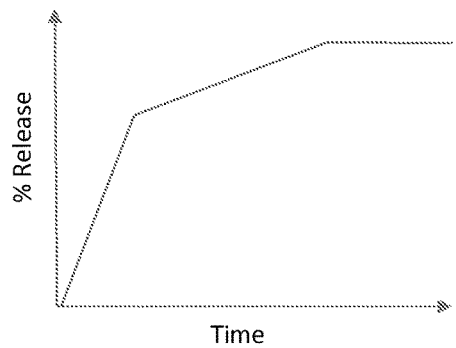
FIG. 17, illustrate burst-controlled release characteristics.
Figure 18:
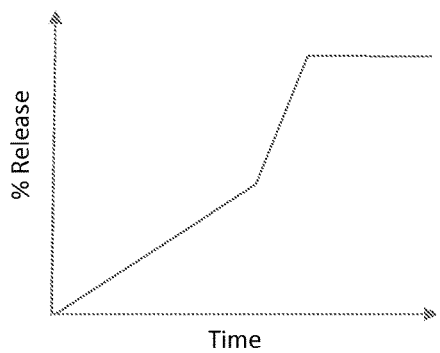
FIG. 18, illustrate controlled-burst release characteristics.
Figure 19:
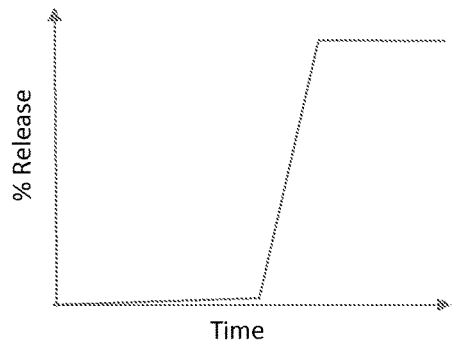
FIG. 19, illustrate lag-burst release characteristics.
Figure 20:
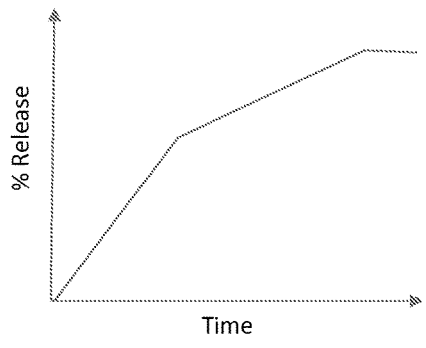
FIG. 20, illustrate controlled-controlled release characteristic.
Figure 21:
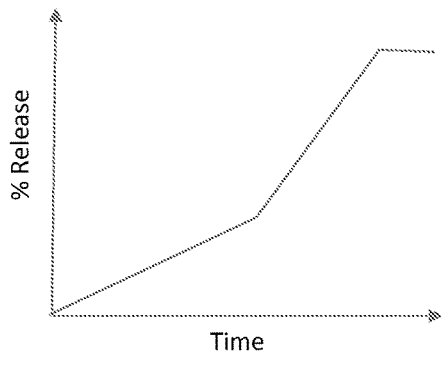
FIG. 21, illustrate controlled-controlled release characteristic.
Figure 22:
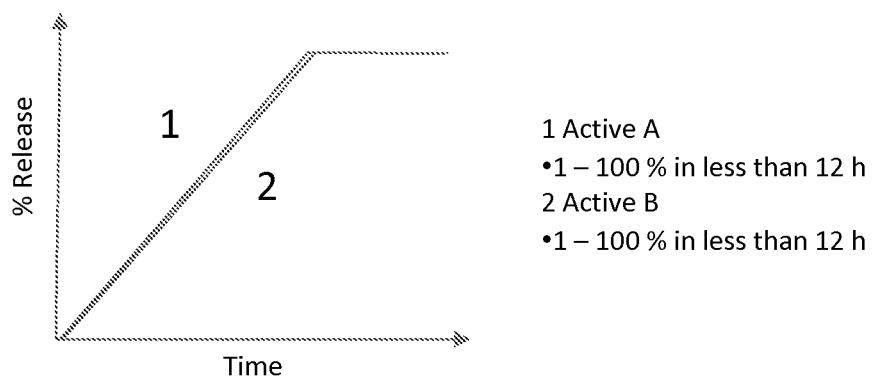
FIG. 22, illustrate releases of two active substances with the same release characteristics.
Figure 23:
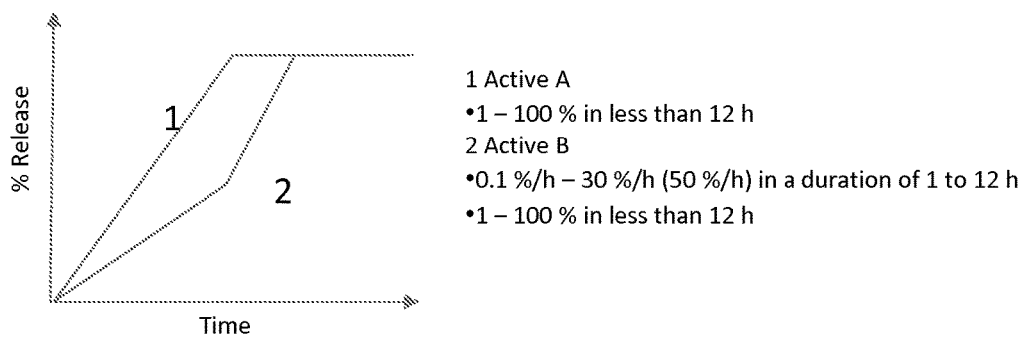
FIG. 23, illustrate releases of two active substances with different release characteristics.
Figure 24:
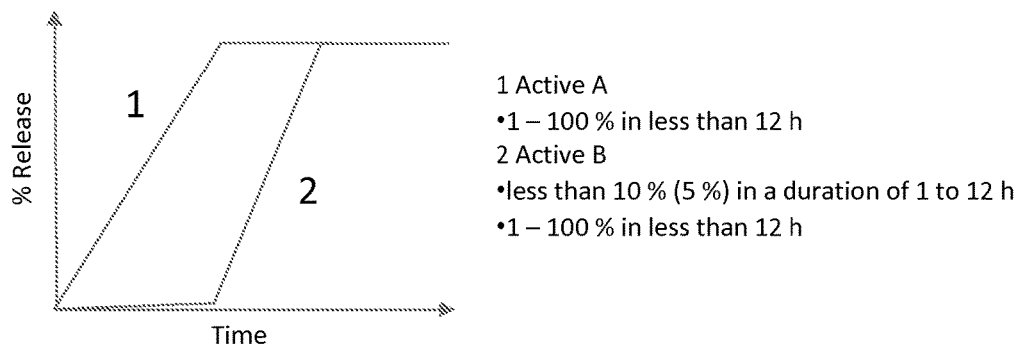
FIG. 24, illustrate releases of two active substances with sequential release characteristics.

The dissolution behaviour as tested by USP 2 apparatus, (pH 6.8, 900 ml phosphate buffered media, 50 RPM) see FIG. 14.

The invention claimed is:

1. A layered pharmaceutical composition for controlled release of an active substance, comprising:
   a solid inner layer (A) comprising the active substance and a disintegrant, the solid inner layer (A) being positioned between two outer layers (B1) and (B2),
   each outer layer (B1) and (B2) comprising one or more substantially water soluble or crystalline polyethylene oxides (PEOs) having a molecular weight (MW) of about 100,000 daltons or greater, wherein the average molecular weight of the PEO present in each outer layer is about 100,000 daltons or greater, wherein each outer layer is free of the disintegrant, and wherein at least one of the outer layers (B1) and (B2) comprises the active substance, and
   a coating (C) forming a shell covering the solid inner layer (A) and partially covering outer layers (B1) and (B2) with two openings exposing a surface of each outer layer (B1) and (B2), wherein the coating (C) comprises a polymer and is substantially insoluble in and impermeable to gastrointestinal fluids;
   wherein the solid inner layer (A), without the outer layers (B1) and (B2) and the coating (C), disintegrates within 60 minutes when subjected to a disintegrating test according to the Eur. Ph; and
   wherein the release of the active substance contained in at least one of the outer layers (B1) and (B2) follows a zero order release pattern for at least 80% w/w release of the total content of the active substance in the outer layers (B1) and (B2).

2. The pharmaceutical composition of claim 1, wherein the active substance in the solid inner layer (A) is present in the form of a multiple unit formulation.

3. The pharmaceutical composition of claim 2, wherein the multiple unit formulation is a controlled release multiple unit formulation.

4. The pharmaceutical composition of claim 2, wherein the active substance of the solid inner layer (A) is present in a form selected from pellets, beads, flakes, mini-tablets, granules, microspheres, nanoparticles, crystals, and combinations thereof.

5. The pharmaceutical composition of claim 2, wherein the multiple unit formulation of solid inner layer (A) comprises a polymer selected from the group consisting of (i) substantially water soluble or crystalline polyglycol homopolymers having a MW of about 100,000 daltons or greater and (ii) substantially water soluble or crystalline polyglycol copolymers having a MW of about 2,000 daltons or greater.

6. The pharmaceutical composition of claim 1, wherein solid inner layer (A) further comprises a filler.

7. The pharmaceutical composition of claim 1, wherein solid inner layer (A) further comprises a polymer selected from the group consisting of (i) substantially water soluble or crystalline polyglycol homopolymers having a MW of about 16,000 daltons or less and (ii) substantially water soluble or crystalline polyglycol copolymers having a MW of about 30,000 daltons or less.

8. The pharmaceutical composition of claim 7, wherein the polymer of solid inner layer (A) is a substantially water soluble or crystalline polyglycol homopolymer having a MW of between about 1,000 daltons and about 16,000 daltons.

9. The pharmaceutical composition of claim 7, wherein the polymer of the solid inner layer (A) is a substantially water soluble or crystalline polyglycol copolymer having a MW of about 25,000 daltons or less.

10. The pharmaceutical composition of claim 1, wherein the concentration of the disintegrant in the solid inner layer (A) is from about 5% w/w to about 80% w/w.

11. The pharmaceutical composition of claim 1, wherein each of the two outer layers (B1) and (B2) further comprises one or more block copolymers of ethylene oxide and propylene oxide.

12. The pharmaceutical composition of claim 1, wherein the average molecular weight of the PEO present in each outer layer is from about 100,000 daltons to about 700,000 daltons.

13. The pharmaceutical composition of claim 11, wherein the block copolymers of ethylene oxide and propylene oxide have a MW of from about 4,000 daltons to about 15,000 daltons.

14. The pharmaceutical composition of claim 1, wherein the concentration of the polymer in each of the two outer layers (B1) and (B2) is from about 5% w/w to about 100% w/w.

15. The pharmaceutical composition of claim 1, wherein both of outer layers (B1) and (B2) comprise the active substance.

16. The pharmaceutical composition of claim 1, wherein at least one of outer layers (B1) and (B2) comprises a second active substance different from the active substance in the solid inner layer (A).

17. The pharmaceutical composition of claim 16, wherein both of outer layers (B1) and (B2) comprise the second active substance different from the active substance of solid inner layer (A).

18. The pharmaceutical composition of claim 16, wherein the composition exhibits zero order release of the second active substance present in outer layers layer(s) (B1) and/or (B2).

19. The pharmaceutical composition of claim 16, wherein the composition exhibits zero order release of at least 80% w/w of the second active substance present in outer layer(s) (B1) and/or (B2).

20. The pharmaceutical formulation of claim 1, wherein the polymer of the coating (C) is selected from the group consisting of ethylcellulose, cellulose acetate, cellulose propionate, cellulose nitrate, polyamide, polyethylene, polyethylene terephthalate, polypropylene, polyurethane, polyvinyl acetate, polyvinyl chloride, silicone rubber, latex, polyhydroxybutyrate, polyhydroxyvalerate, polytetrafluoroethylene, polylactic acid or polyglycolic acid and copolymers thereof, copolymers including ethylene vinyl acetate, styrene-butadienstyrene and styrene-isoprene-styrene, and combinations thereof.

21. The pharmaceutical formulation of claim 20, wherein the polymer of the coating (C) is polylactic acid.

22. The pharmaceutical formulation of claim 1, wherein, when the formulation is exposed to an aqueous medium, the coating (C) does not completely crumble or erode before at least one of the outer layers (B1) and (B2) has completely eroded and the solid inner layer (A) is exposed.

23. The pharmaceutical formulation of claim 1, wherein, when the formulation is exposed to an aqueous medium, at least one of the outer layers (B1) and (B2) erodes at a substantially constant rate.

24. The pharmaceutical formulation of claim 1, wherein, when the formulation is exposed to an aqueous medium, release of the active substance from the solid inner layer (A) is subject a lag time corresponding to the erosion time of at least one of the outer layers (B1) and (B2).

25. The pharmaceutical formulation of claim 1, wherein the coating (C) is a substantially intact empty shell after the composition has been subjected to dissolution testing according to USP 30, NF 25 (711), apparatus 2 (paddle method), in dissolution medium consisting of 0.1 M HCl or phosphate buffer (pH 6.8, pH 6.8 and 40% ethanol, or pH 7.2) in a dissolution medium volume of 900 ml or 1000 ml at a paddle speed of 50rpm.

26. The pharmaceutical formulation of claim 1, wherein the polymer of each of the two outer layers (B1) and (B2), and the polymer of the coating (C) are thermoplastic.

27. The pharmaceutical composition of claim 1, wherein the disintegrant is selected from the group consisting of sodium starch glycolate, povidone, sodium alginate, alginic acid, calcium alginate, carboxymethylcellulose calcium, carboxymethylcellulose sodium, powdered cellulose, chitosan, croscarmellose sodium, crospovidone, hydroxypropyl starch, hydroxypropyl cellulose low-substituted, magnesium aluminium silicate, methylcellulose, microcrystalline cellulose, pregelatinized starch, docusae sodium, guar gum, polacrilin potassium, and combinations thereof.

* * * * *